(12) United States Patent
Leonardi et al.

(10) Patent No.: US 11,904,070 B2
(45) Date of Patent: Feb. 20, 2024

(54) TISSUE SCAFFOLD AND SCAFFOLD COMPOSITION

(71) Applicant: Locate Therapeutics Limited, Nottingham (GB)

(72) Inventors: Antonio Leonardi, Nottingham (GB); Helen Celia Cox, Nottingham (GB); Robin Andrew Quirk, Nottingham (GB); Kevin Morris Shakesheff, Nottingham (GB)

(73) Assignee: LOCATE THEAPEUTICS LIMITED, Nottingham (GB)

( * ) Notice: Subject to any disclaimer, the term of this patent is extended or adjusted under 35 U.S.C. 154(b) by 589 days.

(21) Appl. No.: 16/485,882

(22) PCT Filed: Feb. 12, 2018

(86) PCT No.: PCT/GB2018/050381
§ 371 (c)(1),
(2) Date: Aug. 14, 2019

(87) PCT Pub. No.: WO2018/150166
PCT Pub. Date: Aug. 23, 2018

(65) Prior Publication Data
US 2020/0368387 A1    Nov. 26, 2020

(30) Foreign Application Priority Data
Feb. 15, 2017 (GB) ..................... 1702475

(51) Int. Cl.
| A61L 27/26 | (2006.01) |
| A61L 27/18 | (2006.01) |
| A61L 27/10 | (2006.01) |
| A61L 27/12 | (2006.01) |
| A61L 27/38 | (2006.01) |
| A61K 38/18 | (2006.01) |
| A61L 27/50 | (2006.01) |
| A61L 27/54 | (2006.01) |

(52) U.S. Cl.
CPC .......... *A61L 27/26* (2013.01); *A61K 38/1875* (2013.01); *A61L 27/10* (2013.01); *A61L 27/12* (2013.01); *A61L 27/18* (2013.01); *A61L 27/38* (2013.01); *A61L 27/502* (2013.01); *A61L 27/54* (2013.01); *A61L 2300/252* (2013.01); *A61L 2300/62* (2013.01); *A61L 2430/02* (2013.01); *A61L 2430/12* (2013.01); *A61L 2430/38* (2013.01)

(58) Field of Classification Search
CPC .............................. A61K 9/0024; A61L 27/26
See application file for complete search history.

(56) References Cited

U.S. PATENT DOCUMENTS

| 4,837,285 A | 6/1989 | Berg et al. |
| 9,592,362 B2 * | 3/2017 | Chen ............ B29C 55/22 |
| 2007/0254035 A1 * | 11/2007 | Hao ............ C08J 9/12 |
| | | 514/772.3 |
| 2012/0063997 A1 * | 3/2012 | Hunter ............ A61P 13/00 |
| | | 424/85.4 |

FOREIGN PATENT DOCUMENTS

| WO | WO2008/093094 A2 | 8/2008 |
| WO | WO2014/143871 A2 | 9/2014 |

OTHER PUBLICATIONS

International Search Report and Written Opinion dated May 15, 2018 in International Application No. PCT/GB2018/050381, 11 pages.

* cited by examiner

*Primary Examiner* — Kyle A Purdy
(74) *Attorney, Agent, or Firm* — Lee & Hayes P.C.

(57) ABSTRACT

The invention relates to a scaffold material composition for forming a solid tissue scaffold, the composition comprising a plurality of hollow polymer pellets, each pellet comprising an open hollow extending through the pellet, and wherein the plurality of hollow polymer pellets are capable of interlinking and setting into a solid scaffold. The invention further relates to associated compositions, uses, method of treatment and kits associated with such material.

35 Claims, 19 Drawing Sheets

Figure 1:
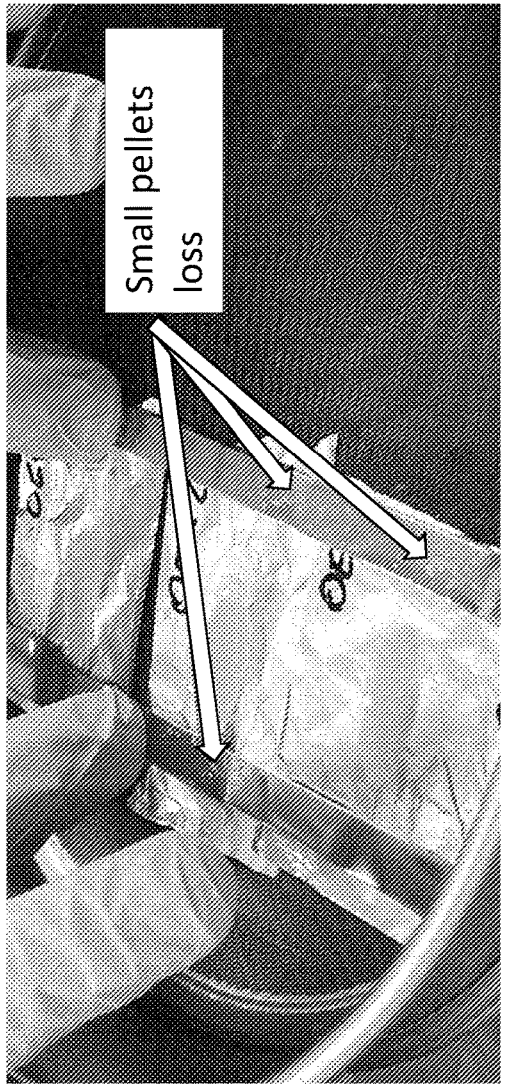

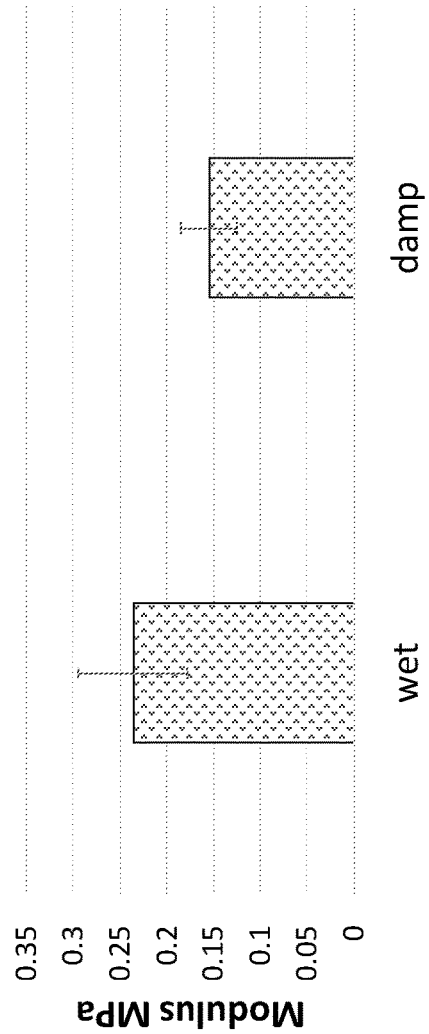
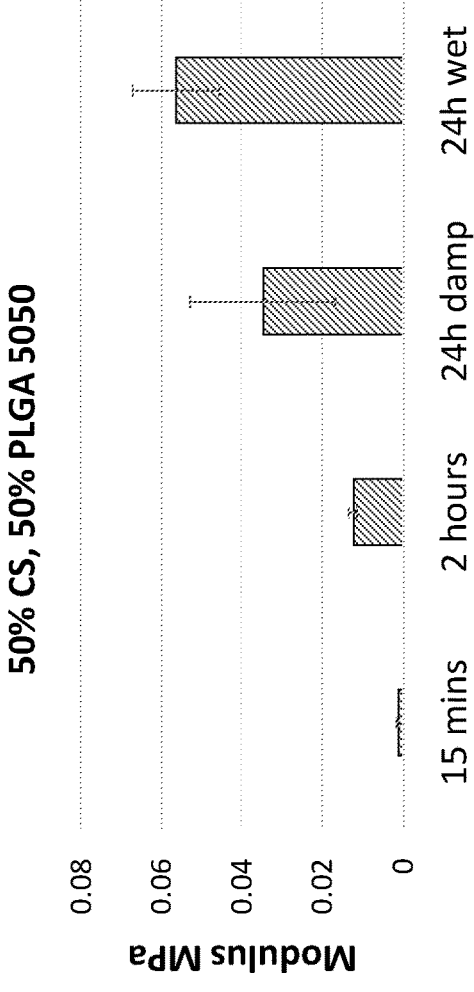

Figure 18
A- Wicking efficiency of 6x12mm scaffolds
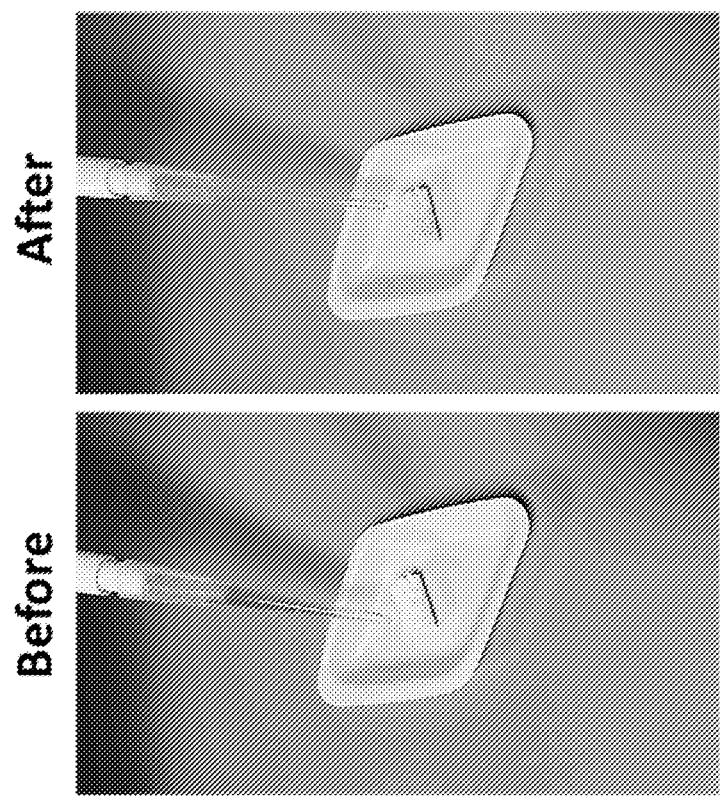
B- Draw-up efficiency of 6x12mm scaffolds
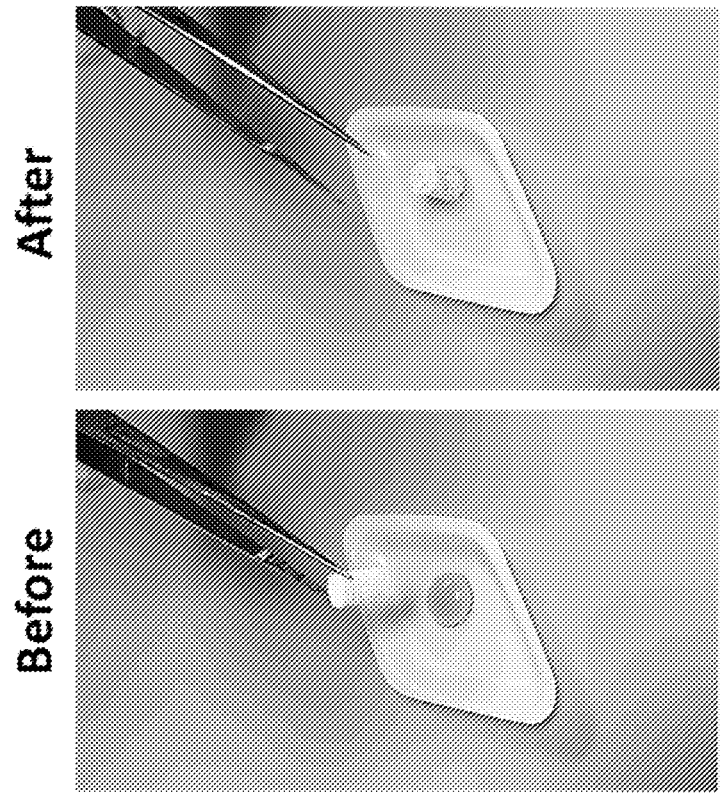

Figure 23
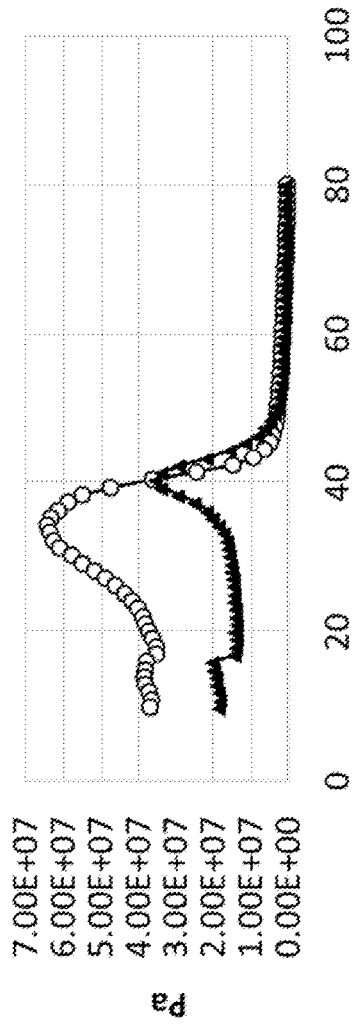
A
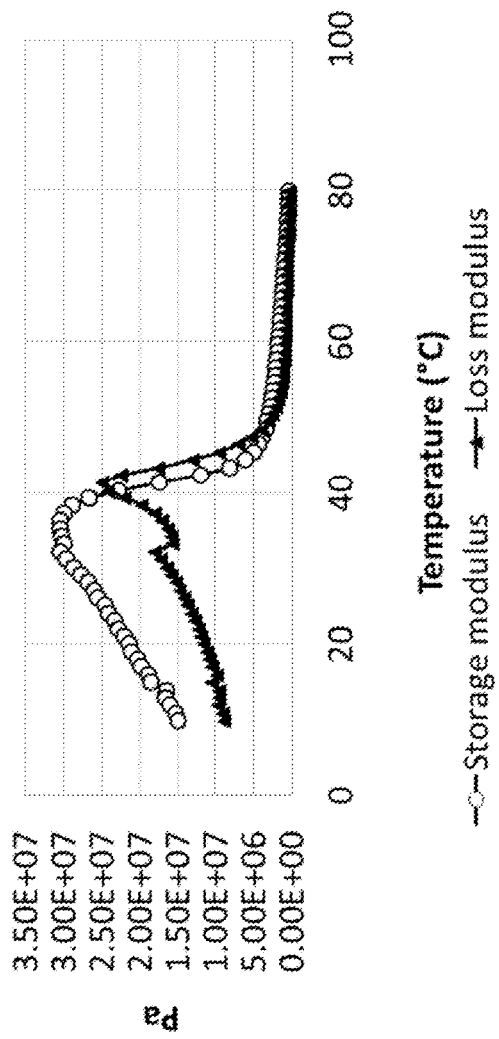
B

TISSUE SCAFFOLD AND SCAFFOLD COMPOSITION

CROSS REFERENCE TO RELATED APPLICATIONS

This Application is a U.S. National Phase Application of International Application No. PCT/GB2018/050381 filed Feb. 12, 2018, which claims priority to Great Britain Patent Application No. 1702475.3 filed Feb. 15, 2017, both of which are hereby incorporated by reference in their entirety herein.

The invention relates to scaffolds formed from polymer pellets, and to the use of such scaffolds in tissue and bone repair, and delivery systems to deliver an agent to a target site in a subject.

BACKGROUND

Within the field of regenerative medicine there are many opportunities for new clinical procedures that stimulate and support tissue repair. Examples of clinical opportunities include regeneration of cardiac muscle after an infarction, induction of bone growth in spinal fusion, healing of diabetic foot ulcers and limitation or, perhaps, reversal of damage due to stroke. Examples of tissues where treatment could facilitate healing are brain tissue, liver tissue and pancreatic tissue, amongst others.

One area where tissue healing is important is bone healing, for example for people with bone disorders. Bone healing is a physiological process in which the body facilitates the repair of the bone after an external injury, infection, surgical intervention or a disease. The physiological healing process can require very long periods and in many cases, it cannot re-establish the original bone properties. For this reason, therapies that accelerate and improve bone healing are of vital importance. Usually, these therapies present osteoconductive, osteoinductive, and osteogenic approaches. In the majority of osteoconductive approaches, a variety of substitutes like gold, stainless steel, titanium, natural/synthetic polymers and ceramics have been tried. The main concerns with the use of these materials for bone reconstruction were their poor ability to vascularise, integrate, and undergo remodelling. This may result in structural failure of the implant under load or pathological changes in the surrounding bone, as seen in stress shielding. The other issues are inflammatory scarring, neoproliferative reaction in the adjacent tissues and infection. Because of their high osteoinductive potential and remodelling characteristics, bioactive substitutes have been used with promising results. This led to the evolution of tissue engineering techniques (biologically enhanced allografts, cell-based therapies, and gene-based therapies) to treat bone disorders. Tissue engineering has been defined as the application of scientific principles to the design, construction, modification, and growth of living tissue using biomaterials, cells, and factors alone and in combination. It involves the use of osteoconductive biomaterial scaffolds, with osteogenic cell populations and osteoinductive bioactive factors. All these approaches have the potential to significantly increase our ability to treat diseases for which no effective treatment currently exists.

Scaffolds can provide an appropriate mechanical environment, architecture and surface chemistry for angiogenesis and tissue formation. The localisation of regenerative agents, such as growth factors, can also be achieved using scaffolds. The use of scaffolds as drug or cell delivery systems has great potential but is also very challenging due to the need to tailor the porosity, strength and degradation kinetics of the scaffolds to the tissue type whilst achieving the appropriate kinetics of release of agents, such as proteins that act as growth factors or cells. A further complication in the use of scaffolds as delivery systems for in vivo repair and/or regeneration is the issue of the route of administration. In many clinical examples the site of tissue requiring repair is either difficult to access (e.g. within the brain for stroke therapies or cardiac muscle for post infarction treatment) or of unknown size and shape. Therefore, there is a need for improved injectable scaffolds that can be administered via minimally invasive procedures.

In broad terms, a scaffold is typically either a pre-formed water-insoluble matrix, with large interconnected pores or a hydrogel. Such scaffolds are implanted into a patient for augmented in vivo tissue repair and/or regeneration. In terms of implantation, the pre-formed water-insoluble matrices must be shaped to fill a cavity within the body, requiring knowledge of the cavity dimensions and limiting the shape of cavity that can be filled. In addition, an invasive operation is required to deliver the scaffold. In contrast, a number of hydrogel materials have been designed that can be delivered directly into the body through a syringe. The gel forms within the body following a trigger signal, for example a temperature change or UV light exposure. Such systems have the advantage that they can fill cavities of any shape without prior knowledge of the cavity dimensions. However, such hydrogels lack large interconnected porous networks and, hence, release of an agent from the gel is limited by poor diffusion properties. Furthermore, the poor mechanical strength of hydrogels means they are often unable to withstand the compressive forces applied in use, furthermore this can result in undesirable delivery properties, as agents in the gels can be in effect squeezed out of the hydrogel.

Resorbable putty or resorbable pastes that solidify after body application, are promising approaches. This area has been widely researched both academically and industrially, with several products such as C-Graft Putty™, Grafton® already having been commercialised. The major obstacles in the success of such approaches are the successful delivery and retention of materials to the required site of action, as well as their malleability before the surgery. Other important obstacles include the ability to deliver additional bioactive therapeutics, to have tailored resorption rates, and to form structures with high level porosity and macropores.

WO2008093094 and WO2004084968 (both of which are incorporated herein by reference) describe compositions and methods for forming tissue scaffolds from polymer pellets, such as PLGA and PLGA/PEG polymer blends. Such scaffolds have been developed to be capable of moulding or injection prior to setting in situ at the site of tissue repair. The setting in situ can be achieved by, for example, exploiting and tuning the glass transition temperature of the pellets for interlinking/crosslinking of the pellets at body temperature. Interlinking events can also be facilitated by non-temperature related methods, such as by plasticisation by solvents. A porous structure is achieved by leaving gaps between the pellets and optionally further providing porous polymer pellets. The resulting scaffolds maintain a high compressive strength that is useful in tissue repair, especially for connective tissues such as bone, whilst also maintaining porosity useful for cell growth and agent delivery. However, an aim of the present invention is to provide improved compositions, methods and processes for forming scaffold material for use in tissue repair.

SUMMARY OF INVENTION

According to a first aspect of the present invention, there is provided a scaffold material composition for forming a solid tissue scaffold, the composition comprising a plurality of hollow polymer pellets, each pellet comprising an open hollow extending through the pellet, and
wherein the plurality of hollow polymer pellets are capable of interlinking and setting into a solid scaffold.

According to another aspect of the present invention, there is provided a solid scaffold for tissue repair or replacement comprising a plurality of hollow polymer pellets, the hollow polymer pellets comprising a polymer pellet having an open hollow extending through the polymer pellet, wherein the hollow polymer pellets are inter-linked with each other.

According to another aspect of the present invention, there is provided a method of forming a scaffold for tissue repair or replacement, the method comprising:
providing scaffold material comprising hollow polymer pellets, each pellet comprising an open hollow extending through the pellet; and
setting the scaffold material such that it sets into a solid scaffold of hollow polymer pellets.

According to another aspect of the present invention, there is provided a method of forming a scaffold material for controlled release of an agent in situ, the method comprising:
providing hollow polymer pellets;
providing an agent, wherein the agent is in a powder form;
mixing the hollow polymer pellets with the powder agent;
suspending the mixture in a liquid carrier to form a scaffold material that is a hollow polymer pellet suspension; and optionally
setting the scaffold material such that it sets into a solid scaffold of hollow polymer pellets, wherein the powder agent is encapsulated amongst the scaffold of hollow polymer pellets.

According to another aspect of the present invention, there is provided a method of forming a scaffold for controlled release of an agent in situ, the method comprising:
providing hollow polymer pellets;
providing an agent, wherein the agent is in a powder form;
mixing the hollow polymer pellets with the agent;
suspending the mixture in a liquid carrier to form a scaffold material that is a hollow polymer pellet suspension; and
setting the scaffold material such that it sets into a solid scaffold of hollow polymer pellets, wherein the powder agent is encapsulated amongst the scaffold of hollow polymer pellets.

According to another aspect of the present invention, there is provided a method of forming a scaffold material, the method comprising:
providing hollow polymer pellets;
suspending the hollow polymer pellets in a liquid carrier to form a scaffold material, which is a hollow polymer pellet suspension, wherein the liquid carrier comprises a plasticiser; and
optionally setting the hollow polymer pellet suspension such that it sets into a solid scaffold of hollow polymer pellets.

According to another aspect of the present invention, there is provided a method of forming a scaffold, the method comprising:
providing hollow polymer pellets;
suspending the hollow polymer pellets in a liquid carrier to form a scaffold material, which is a hollow polymer pellet suspension, wherein the liquid carrier comprises a plasticiser; and setting the scaffold material such that it sets into a solid scaffold of hollow polymer pellets.

According to another aspect of the invention, there is provided a method of forming a scaffold material, the method comprising:
providing hollow polymer pellets;
suspending the hollow polymer pellets in a liquid carrier to form a scaffold material, which is a hollow polymer pellet suspension, wherein the scaffold material comprises a first plasticiser in the hollow polymer pellets and/or the liquid carrier, and a second plasticiser in the liquid carrier,
wherein the first plasticiser is selected from any one of TEC (triethyl citrate), ethanol, benzoic acid, triacetin, NMP, DMSO and PEG; and the second plasticiser is selected from any one of PEG, DMSO, NMP, TEC (triethyl citrate), ethanol, benzoic acid, and triacetin (TA), wherein the first and second plasticisers are different; and
optionally setting the hollow polymer pellet suspension such that it sets into a solid scaffold of hollow polymer pellets.

According to another aspect of the invention, there is provided a method of forming a scaffold, the method comprising:
providing hollow polymer pellets;
suspending the hollow polymer pellets in a liquid carrier to form a scaffold material, which is a hollow polymer pellet suspension, wherein the scaffold material comprises a first plasticiser in the hollow polymer pellets and/or the liquid carrier, and a second plasticiser in the liquid carrier,
wherein, the first plasticiser is selected from any one of TEC (triethyl citrate), ethanol, benzoic acid, triacetin, NMP, DMSO and PEG; and the second plasticiser is selected from any one of PEG, DMSO, NMP, TEC (triethyl citrate), ethanol, benzoic acid, and triacetin (TA), wherein the first and second plasticisers are different; and
setting the scaffold material such that it sets into a solid scaffold of hollow polymer pellets.

According to another aspect of the present invention, there is provided a method of forming a scaffold material comprising hollow polymer pellets, the method comprising:
extruding a polymer through an extruder, wherein the extruder comprises a die to form a hollow in the polymer extrudate;
cutting the polymer extrudate into pellets to form hollow polymer pellets; and
optionally suspending the hollow polymer pellets in a liquid carrier to form a hollow polymer pellet suspension; and
further optionally forming a scaffold by setting the hollow polymer pellets, or suspension thereof, such that it sets into a solid scaffold of hollow polymer pellets.

According to another aspect of the present invention, there is provided a method of forming a scaffold material comprising a natural-polymer or non-polymer particle content, the method comprising:

blending a polymer with natural-polymer or non-polymer particles;

forming hollow polymer pellets from the blend, wherein the hollow polymer pellets have the natural-polymer or non-polymer particles encapsulated therein; and optionally suspending the hollow polymer pellets in a liquid carrier to form a hollow polymer pellet suspension; and further optionally setting the hollow polymer pellet suspension such that it sets into a solid scaffold of hollow polymer pellets.

According to another aspect of the present invention, there is provided a method of forming a scaffold comprising a natural-polymer or non-polymer particle content, the method comprising:

blending a polymer with natural-polymer or non-polymer particles;

forming scaffold material comprising hollow polymer pellets from the blend, wherein the hollow polymer pellets have the natural-polymer or non-polymer particles encapsulated therein; and setting the scaffold material such that it sets into a solid scaffold of hollow polymer pellets.

The method may further comprise suspending the hollow polymer pellets in a liquid carrier to form a scaffold material comprising a hollow polymer pellet suspension prior to setting.

According to another aspect of the present invention, there is provided a method of forming a scaffold material which is capable of setting in less than 5 minutes, wherein the scaffold material is provided in accordance with any of the methods of the invention herein, and wherein the plasticiser is provided in the carrier in a range of between about 4% and about 6% (w/v) of plasticiser.

According to another aspect of the present invention, there is provided a method of forming a scaffold material having a scaffold setting time of between about 5 and about 15 minutes, wherein the scaffold material is provided in accordance with any of the methods of the invention herein, and wherein the plasticiser is provided in the carrier in a range of between about 2.5% and about 3.5% (w/v) of plasticiser.

According to another aspect of the present invention, there is provided a method of forming a scaffold material having a scaffold setting time of greater than 60 minutes, wherein the scaffold material is provided in accordance with any of the methods of the invention herein, and wherein the plasticiser is TA or TEC and is provided in the carrier in the range of between about 0.5% and about 1% (w/v).

According to another aspect of the present invention, there is provided a method of forming a scaffold material having a scaffold setting temperature of less than 35 degrees C., wherein the scaffold material is provided in accordance with any of the methods of the invention herein, and wherein the plasticiser is TA or TEC and is provided in the carrier in a range of between about 3% and about 5% (w/v); or alternatively two plasticisers are provided, with at least one plasticiser in the carrier and the total plasticiser content may not exceed 4% or 5% (w/v), wherein one plasticiser is TA or TEC, optionally, wherein the TA or TEC are provided up to 2% of the carrier.

According to another aspect of the present invention, there is provided a method of forming a scaffold material having a scaffold setting temperature of greater than 35 degrees C., for example about 37 degrees C., wherein the scaffold material is provided in accordance with any of the methods of the invention herein, and wherein the plasticiser is TA or TEC and is provided in a range of between about 0.5% and about 1% (w/v).

According to another aspect of the invention, there is provided a system for selecting hollow polymer pellet scaffold formation properties comprising:

(a) selecting a desired scaffold setting temperature and carrying out a method of forming a scaffold material according to the invention herein, which is arranged to provide the appropriate scaffold setting temperature; or (b) selecting a desired scaffold setting time and carrying out a method of forming a scaffold material according to the invention herein, which is arranged to provide the appropriate scaffold setting time; or (c) selecting a desired scaffold material Young's modulus prior to setting of the scaffold, and carrying out a method of forming a scaffold material according to the invention herein, which is arranged to provide the appropriate scaffold material Young's modulus.

According to another aspect of the present invention, there is provided a method of forming a scaffold material suitable for forming a scaffold having a $1^{st}$ order agent release kinetic, wherein the scaffold material is provided in accordance with methods of the invention herein, and wherein the agent is provided as a powder prior to blending with polymer to form the hollow polymer pellets of the scaffold material.

According to a yet further aspect, the invention provides a scaffold material produced by any method of the invention.

According to a yet further aspect, the invention provides a scaffold produced by any method of the invention.

According to another aspect of the invention, there is provided scaffold material for forming a scaffold for controlled release of an agent, wherein the scaffold material comprises:

hollow polymer pellets;

an agent, wherein the agent is in a powder form and is encapsulated amongst and between the hollow polymer pellets; and a liquid carrier suspending the hollow polymer pellets.

According to another aspect of the invention, there is provided scaffold material for forming a scaffold, wherein the scaffold material comprises:

hollow polymer pellets;

natural-polymer particles and/or non-polymer particles (such as ceramic), wherein the natural-polymer particles and/or non-polymer particles are encapsulated within the hollow polymer pellets; and optionally a liquid carrier suspending the hollow polymer pellets.

According to another aspect of the invention, there is provided scaffold material for forming a scaffold, wherein the scaffold material comprises:

hollow polymer pellets;

a liquid carrier suspending the hollow polymer pellets, wherein the liquid carrier comprises a plasticiser; and optionally wherein a second plasticiser is provided in the carrier and/or the hollow polymer pellets.

According to another aspect of the invention, there is provided a scaffold for controlled release of an agent, wherein the scaffold comprises:

inter-linked hollow polymer pellets; and an agent, wherein the agent is in a powder form and is encapsulated amongst and between the hollow polymer pellets.

According to another aspect of the invention, there is provided a scaffold for bone repair, wherein the scaffold comprises:

inter-linked hollow polymer pellets; and natural-polymer particles and/or non-polymer particles (such as ceramic), wherein the natural-polymer particles and/or non-polymer particles are encapsulated within the hollow polymer pellets.

In a further aspect, the invention provides a method of delivering an agent to a subject comprising providing a scaffold material, wherein the agent is located within hollow polymer pellets within the scaffold material; administering the scaffold material to a subject; allowing the scaffold material to solidify/self-assemble in the subject to form a scaffold; and allowing the agent contained within the scaffold material to be released into the subject at the site of administration.

According to another aspect of the present invention there is provided a method of treatment comprising the administration of a scaffold or scaffold material according the invention.

According to another aspect, the invention provides a kit for use in delivering an agent to a target comprising:
hollow polymer pellets;
powdered agent; and
a carrier solution; and optionally
instructions to mix the hollow polymer pellets, powdered agent and carrier.

According to another aspect, the invention provides a kit for use in forming a scaffold comprising:
hollow polymer pellets;
natural-polymer particles and/or non-polymer particles; and
a carrier solution; and optionally
instructions to mix the hollow polymer pellets, natural-polymer particles and/or non-polymer particles and carrier.

According to another aspect, the invention provides a kit for use to form a scaffold comprising:
hollow polymer pellets; and
a carrier solution comprising a plasticiser; and optionally the hollow polymer pellets and/or the carrier comprise a second plasticiser; and further optionally
instructions to mix the hollow polymer pellets and carrier.

Advantageously, the use of hollow polymer pellets to form a scaffold structure provides a high porosity scaffold whilst also maintaining good compressive strength and/or Young's modulus. High porosity scaffolds have more surface area that gives more space to the cells for growth. Further advantageously, if the hollow polymer pellets are combined with cells, their high surface area allow a better cell loading when compared to the non-hollow polymer pellets. If the hollow polymer pellets are combined with cells, their holes protect the cells when shear forces occur. This can be particularly advantageous when mixing the cells and scaffold material where higher viability of the cells can be maintained. Therefore, the hollow polymer pellets provide a shielding effect for cells.

Additionally, the high surface area of the hollow polymer pellets gives another control mechanism for polymer degradation. A higher surface area provided by the hollow polymer pellet structure can result in a faster degradation profile. This can be useful for example in controlled release of active agent by degradation, for example release of surface-bound active or encapsulated active.

The hollow/lumen of the hollow polymer pellets can advantageously be used to influence the resultant pore size distribution of the entire scaffold. It provides a controlled and repeated dimension of pore size within an otherwise broad range of pellet sizes. This approach can be used to either increase the percentage of macropores within the scaffold (e.g. >100 microns or preferably over 250 microns) or microporosity (small lumens to increase percentage of <10 micron pores). Macropores are important for cell infiltration and tissue growth, and microporosity is important for mass transfer.

The provision of hollow polymer pellets can also help prevent the build-up of degradation products within the bulk of the polymer, which can be auto-catalytic or pro-inflammatory when released.

The current invention further advantageously describes resorbable scaffold material able to set at different times and at different temperatures. Such material may provide a scaffold support for tissue formation if used alone, or osteoinductive and osteogenic effects if used with drugs or bioactive substitutes, such as cells, de-cellularised matrix (DCM) and growth factors. The control of paste setting under different temperatures can be useful for injectable scaffold material. For example, if the setting occurs at body temperature (37° C.), said pastes can be handled with no rush at room temperature before injection. The control of paste setting under different times can be useful for making putties. In fact, a paste that sets after few minutes can form a putty that, depending on the needs, can be differently shaped and administered. The invention herein further provides the ability to control drug release by changing the formulation variables of particles size, agent loading method, polymer type, plasticiser type and concentration and blend composition.

FIGURES

The invention will be exemplified with the following accompanying figures, by way of example only.

FIG. 1—Experimental conditions for a cohesion test: sieve mesh/tray with immersed aluminium foils and pastes.

Figure 2:
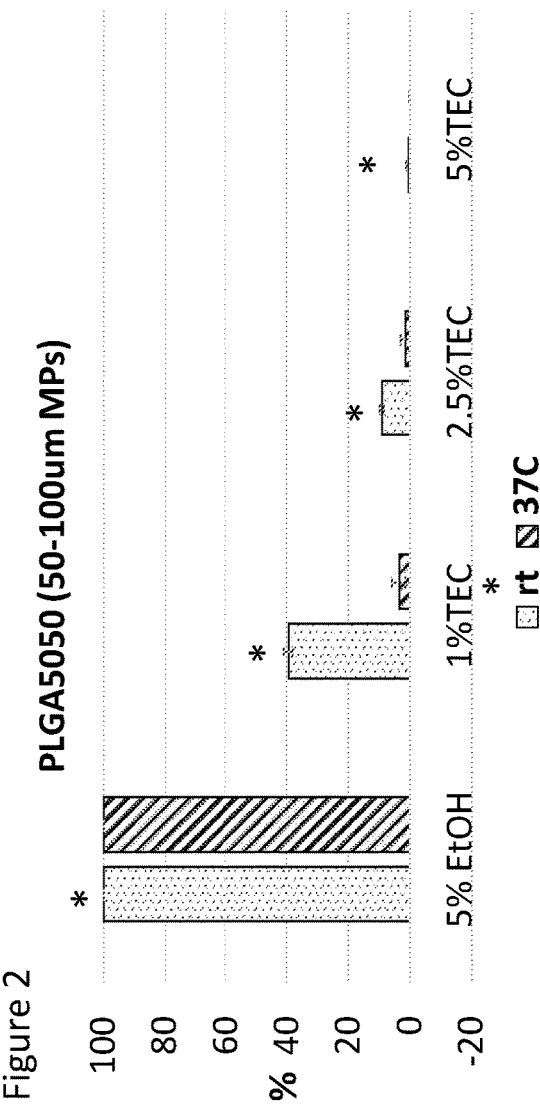

FIG. 2—PLGA 50:50 (50-100 µm pellets) mass loss after 15 min sintering at room temperature or 37° C.

Figure 3:
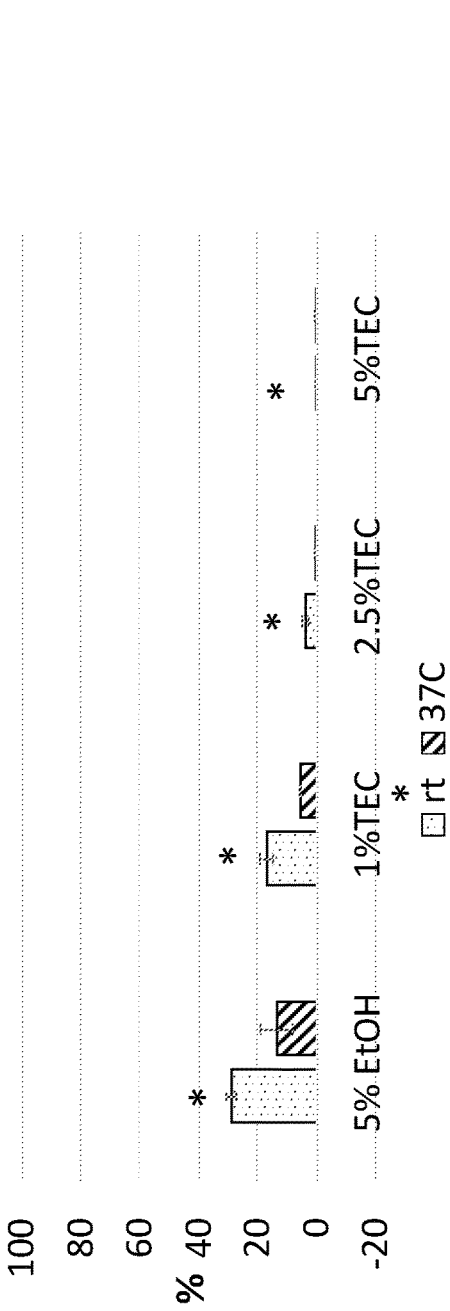
Figure 4:
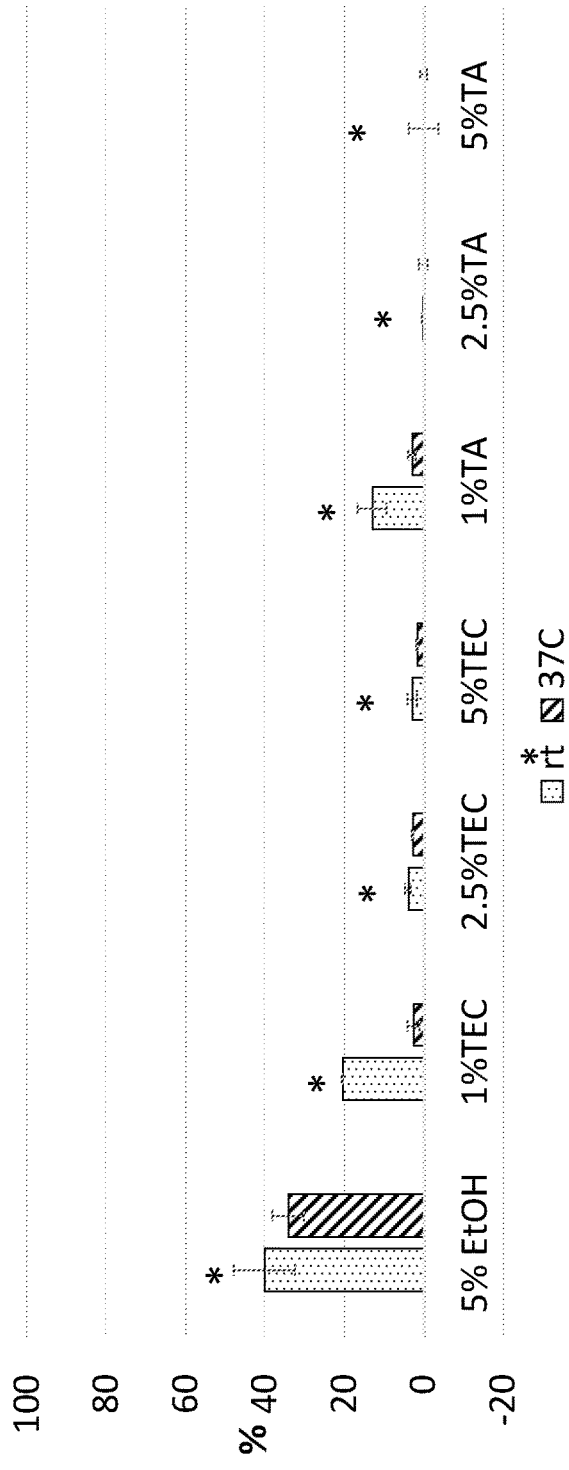
Figure 5:
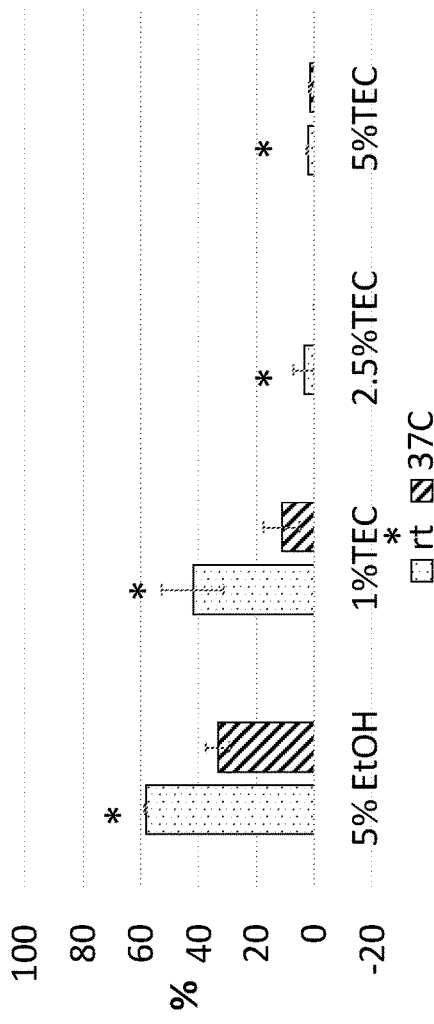

FIG. 3—74.8% w/w PLGA50:50, 5.2% w/w PEG400, 20% w/w SIM (300-400 µm HME pellets) mass loss after 15 min sintering at room temperature or 37° C.

FIGS. 4—46.75% w/w PLGA 95:5, 3.25% w/w PEG400, 50% w/w CS (300-400 µm HME pellets) mass loss after 15 sintering min at room temperature or 37° C.

FIGS. 5—46.75% w/w PLGA 95:5, 3.25% w/w PEG400, 50% w/w β-TCP (300-400 µm HME pellets) mass loss after 15 min sintering at room temperature or 37° C.

Figure 6:
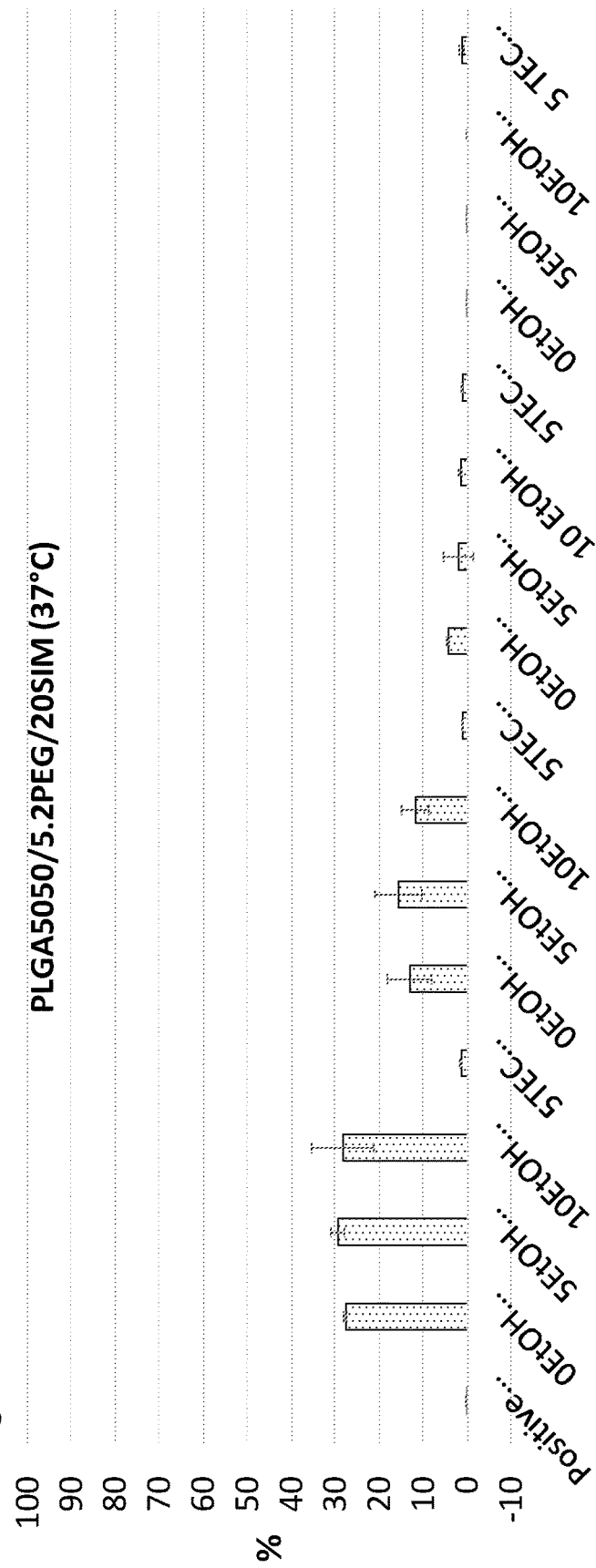

FIG. 6—74.8% w/w PLGA50:50, 5.2% w/w PEG400, 20% w/w SIM (300-400 µm HME pellets) mass loss after sintering at different time points.

Figure 7:

FIGS. 7—6×12 mm scaffolds

Figure 8:

FIG. 8—Mechanical properties of 6×12 cylindrical PLGA 50:50 (50-200 µm) scaffolds after 15 minutes and 2 hours sintering at either 32° C. or 37° C. N=3±1 SD FIG. 9—Mechanical properties of PLGA 50:50 (50-200 µm) scaffolds sintered with 3% TEC after 24 hours sintering at 37° C. in either wet (immersed in PBS) or damp (sealed in a humidified bag) conditions. N=3±1 SD FIG. 10—Young's modulus of PLGA/CS (50-200 µm) scaffolds over time at 37° C., with 24 hours values for damp sinter conditions (37° C., 90% humidity) and wet conditions (fully immersed in 37° C. Phosphate buffered saline, PBS)

Figure 11:
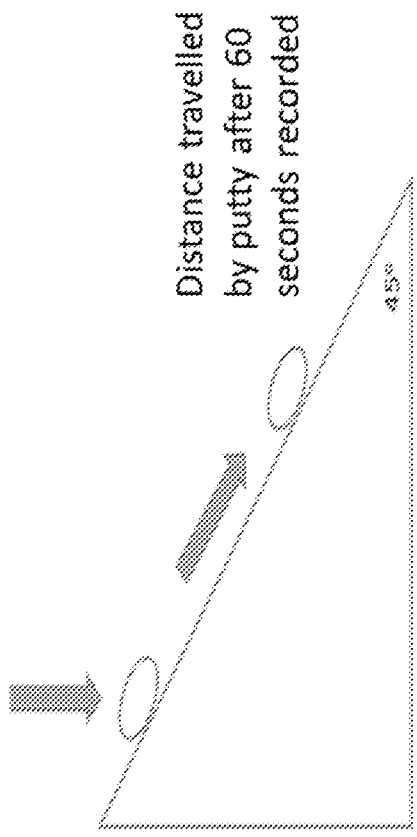

FIG. 11—Schematic of experimental set up for viscosity measurements.

Figure 12:
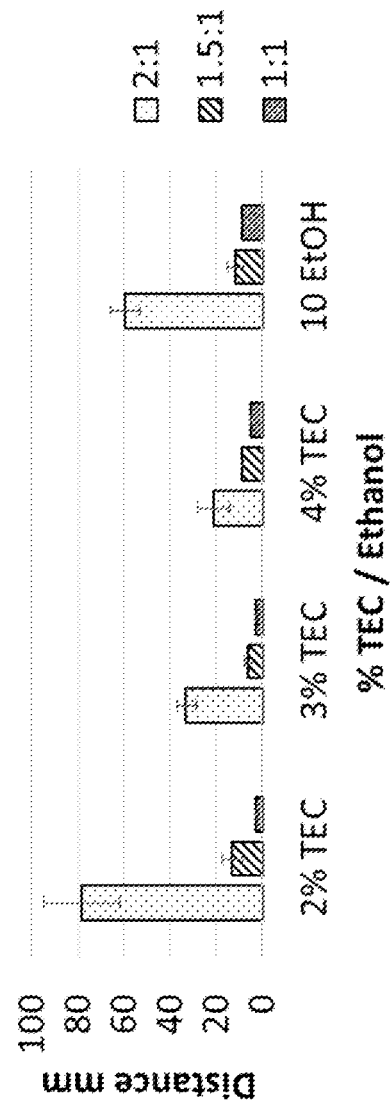

FIG. 12—Distance flowed by putty at 45° in 60 s at room temperature using different carrier:polymer ratios and varying concentrations of TEC or 10% ethanol.

Figure 13:
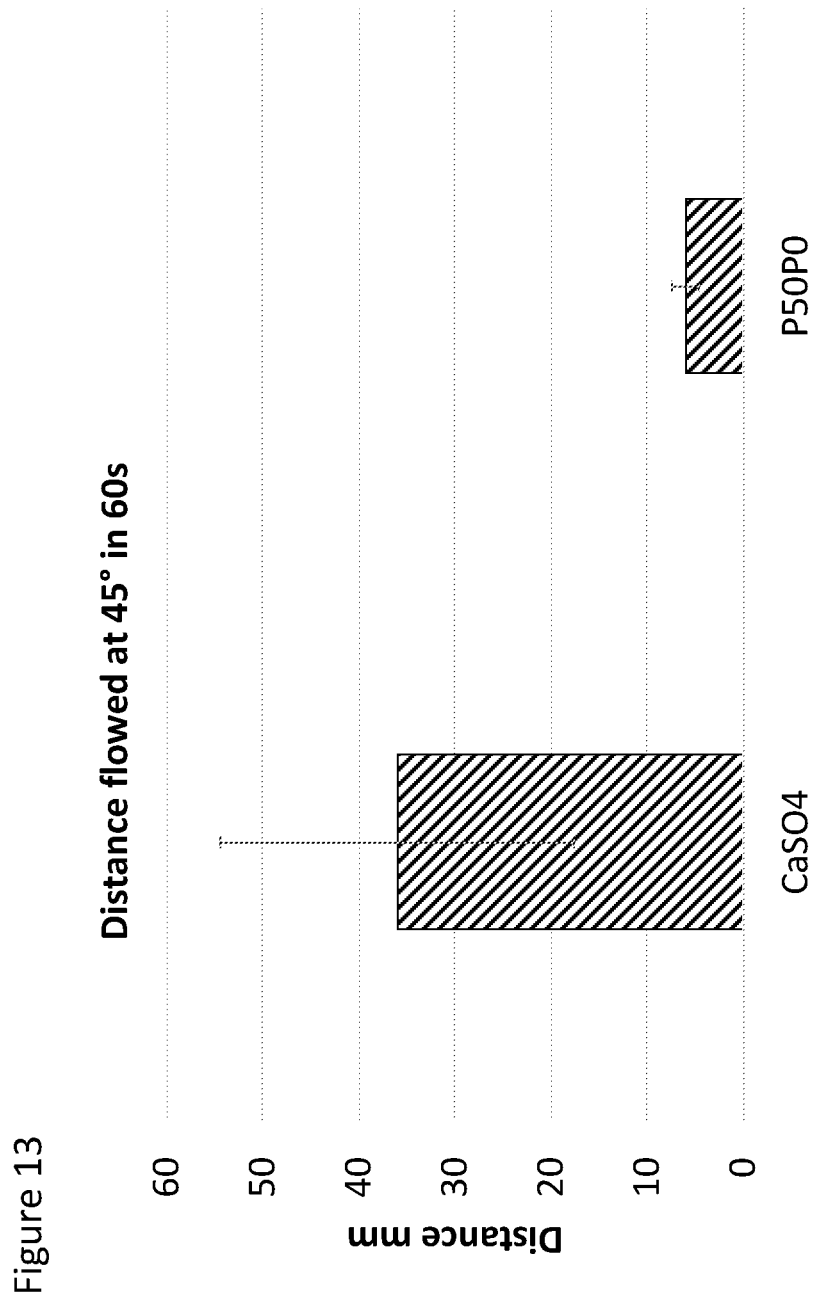
Figure 14:
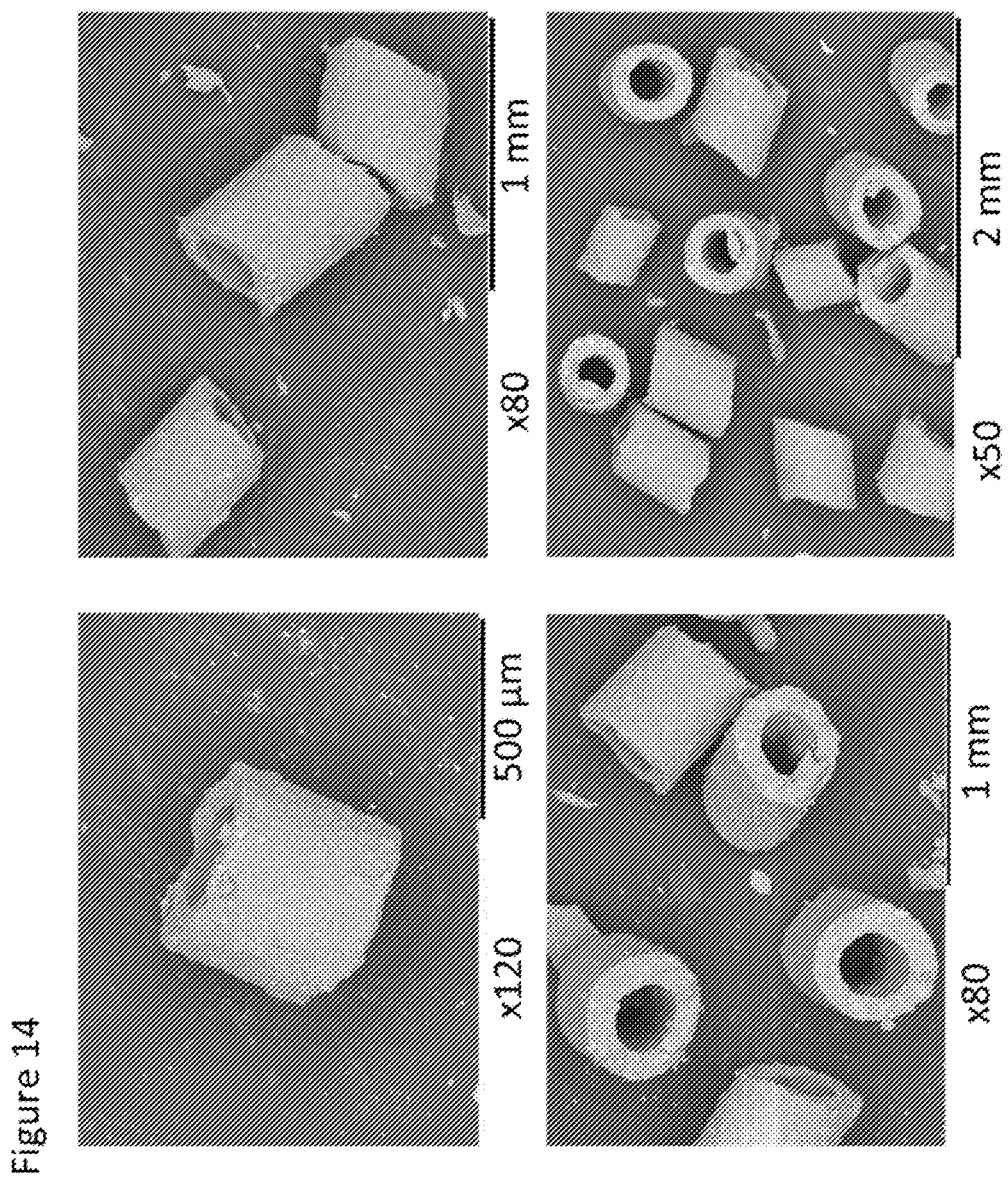

FIG. 13—Distance flowed by paste containing 50% CaSO4 and blank PLGA paste material at t=0 minutes at 45° in 60 seconds FIG. 14—SEM images of extruded hollow polymer pellets of PLGA-CS-PEG at various magnifications. The hollow polymer pellets comprise PLGA95:5=46.75%, PEG400=3.25%, CS=50%.

Figure 15:
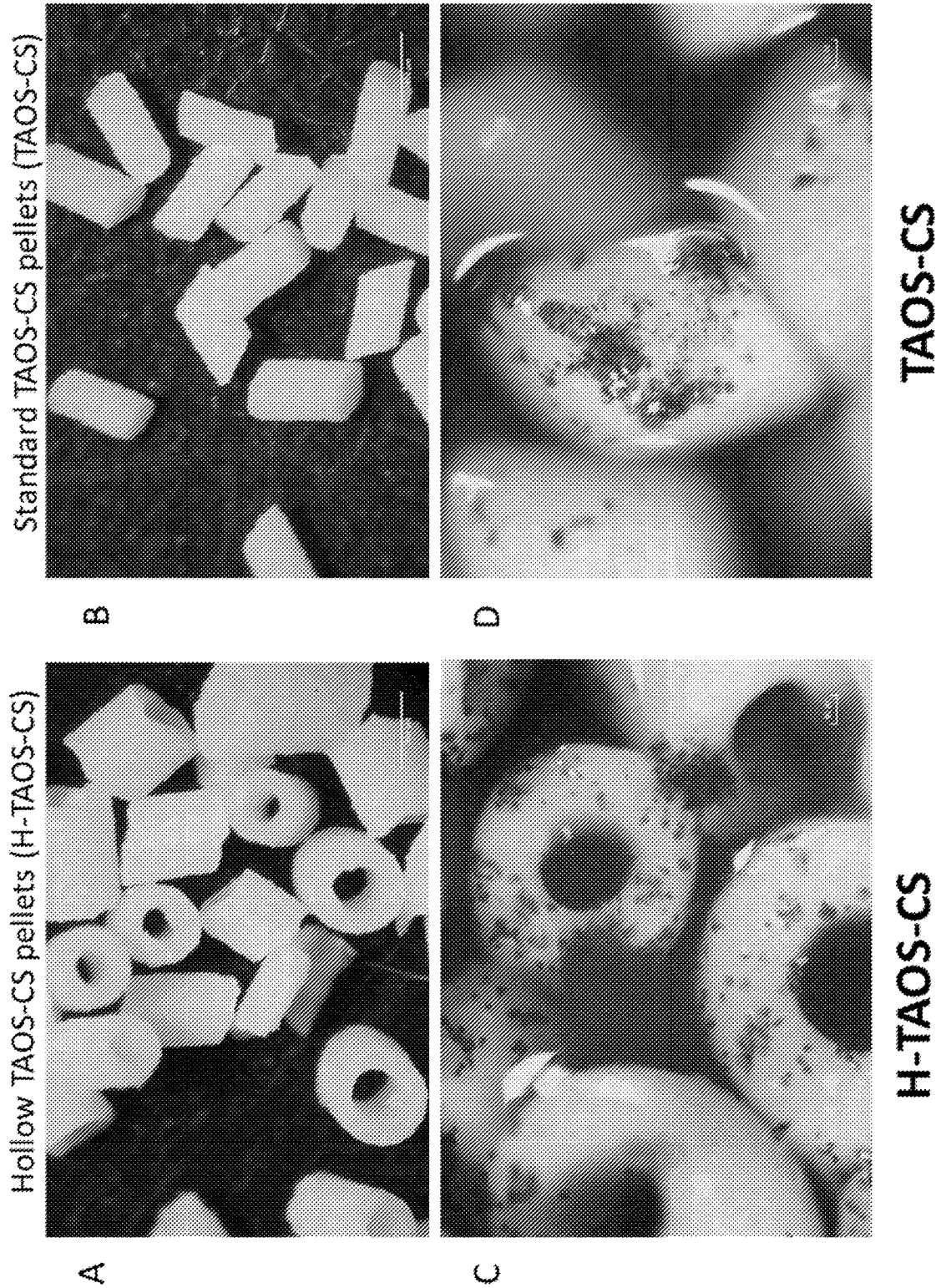

FIG. 15—Images of hollow polymer pellets versus standard polymer pellets with and without mesenchymal stem cells (MSCs). A: Hollow polymer pellets with ceramic content (H-TAOS-CS). B: Standard polymer pellets with ceramic content (TAOS-CS) having no hollow structure. C: Mesenchymal stem cell (MSC) attachment on Hollow polymer pellets with ceramic content (H-TAOS-CS). D: Mesenchymal stem cell (MSC) attachment on standard polymer pellets with ceramic content (TAOS-CS).

Figure 16:
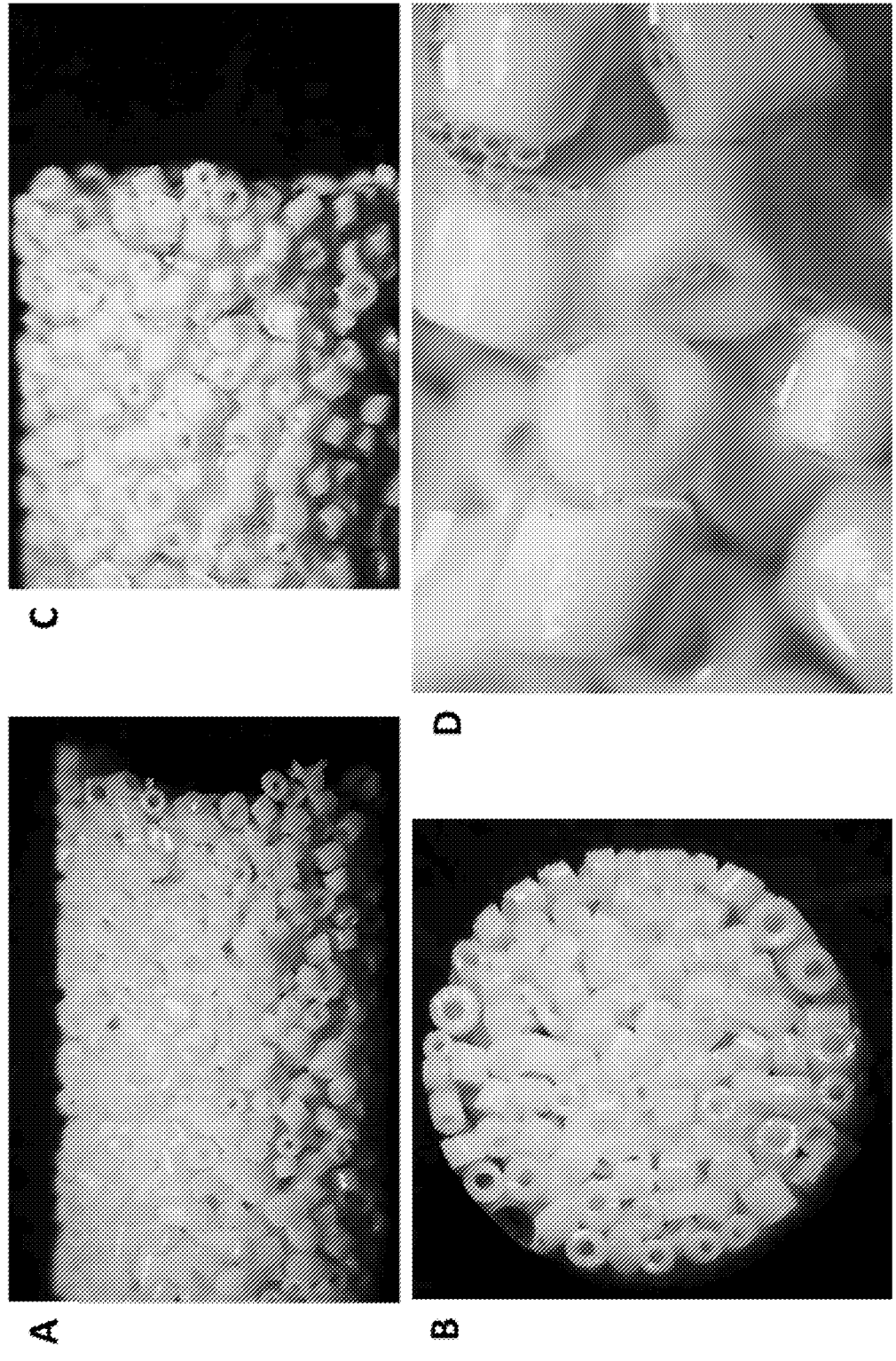

FIG. 16—Images of scaffold formed with hollow polymer pellets, with (C and D) and without media (A and B).

Figure 17:
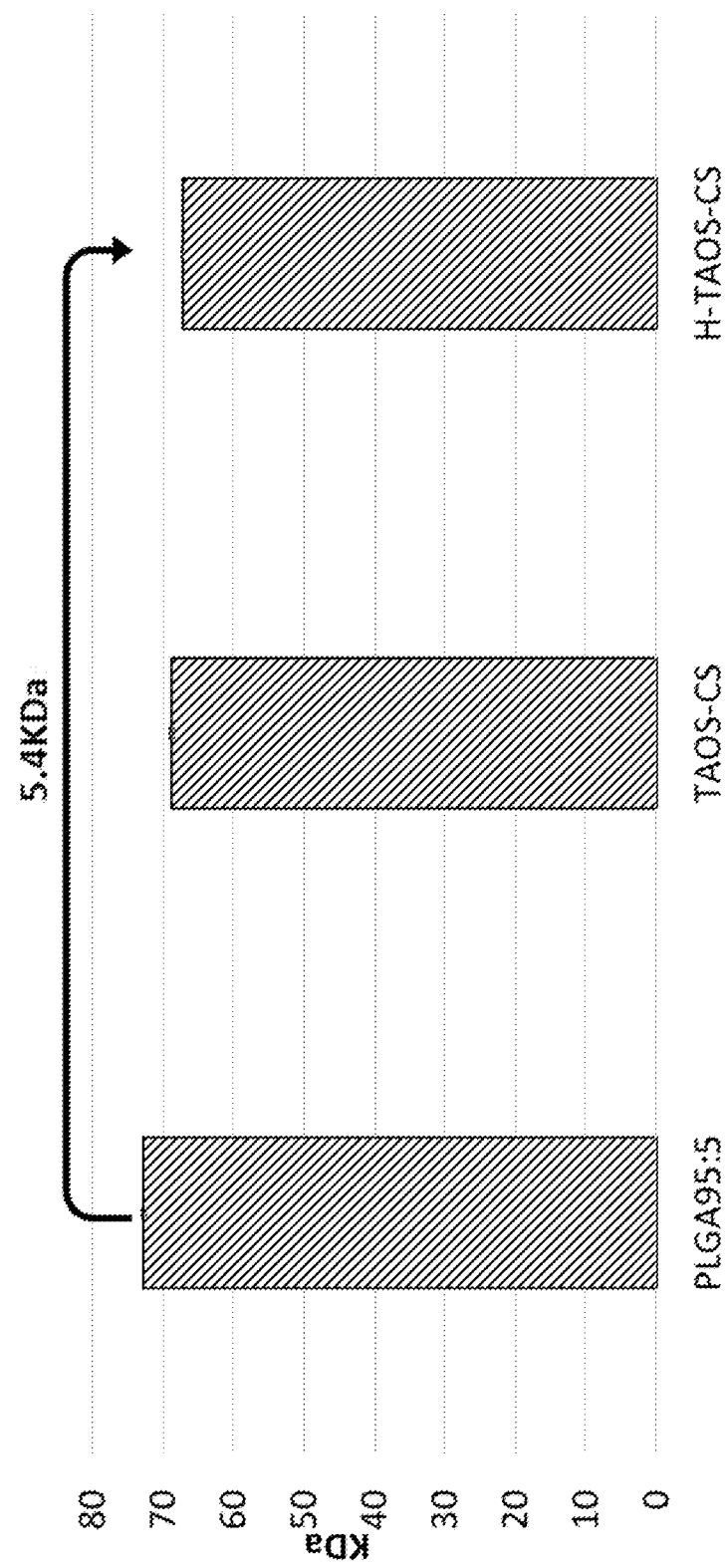

FIG. 17—Effect of manufacturing on PLGA molecular weight.

FIG. 18—Demonstration of wicking (A) and draw-up (B) efficiency using cell culture medium (DMEM).

Figure 19:
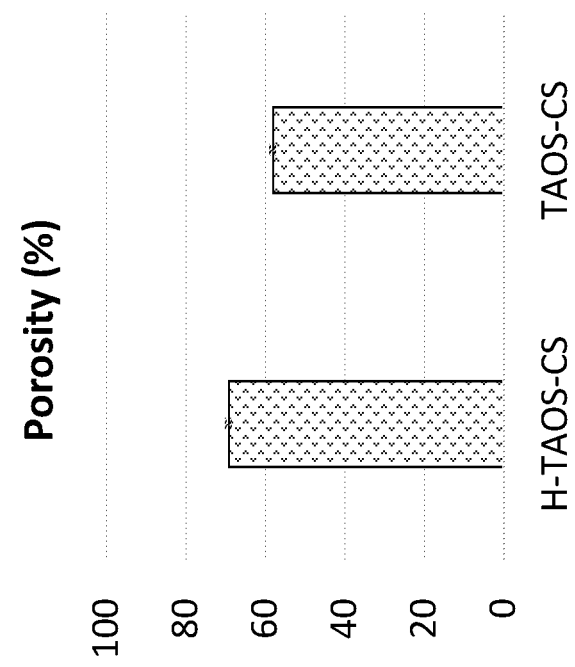

FIG. 19—Demonstration of bulk porosity of hollow polymer pellet scaffold ('H-TAOS-CS') versus standard pellet scaffold ('TAOS-CS') (for scaffolds of 6×12 mm dimension).

Figure 20:
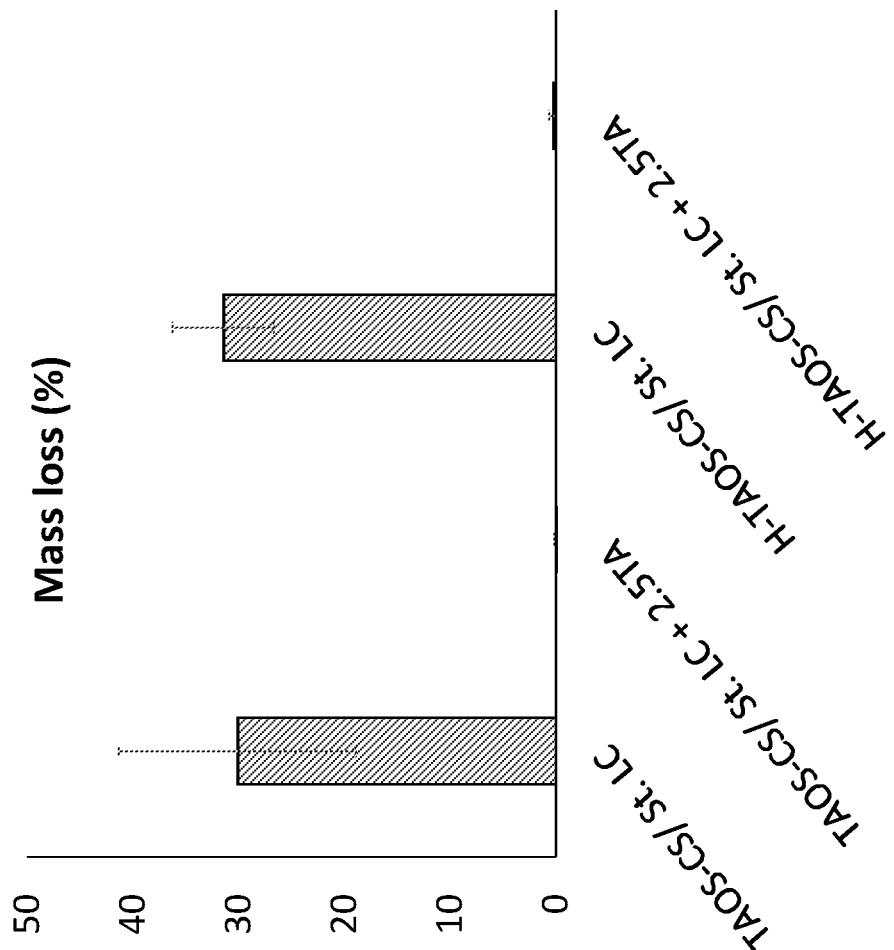

FIG. 20—TAOS' mass losses under the experimental conditions.

Figure 21:
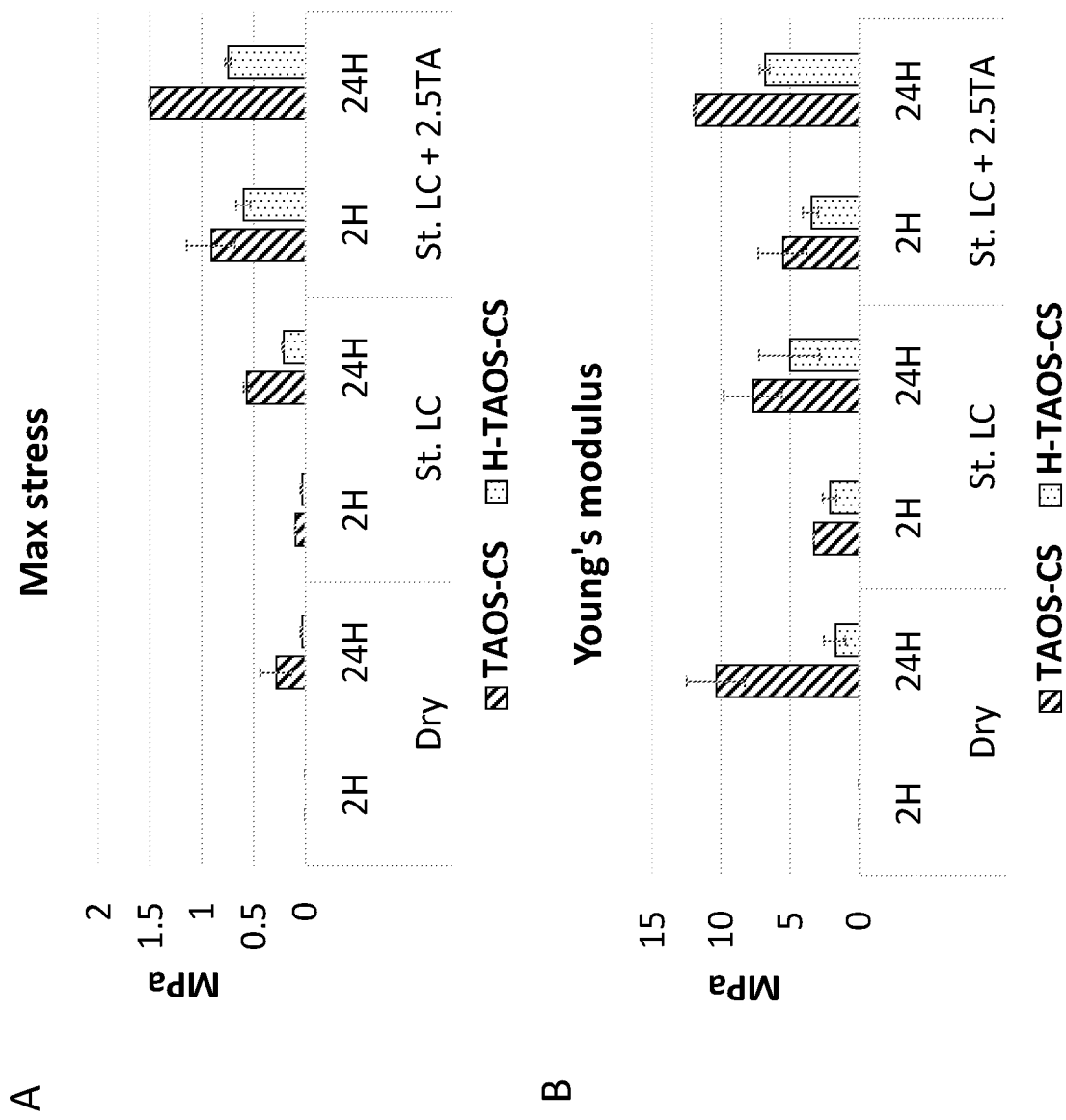

FIG. 21—Shows max stress (A) and young's modulus (B) over time for H-TAOS-CS scaffolds versus TAOS-CS scaffold.

Figure 22:
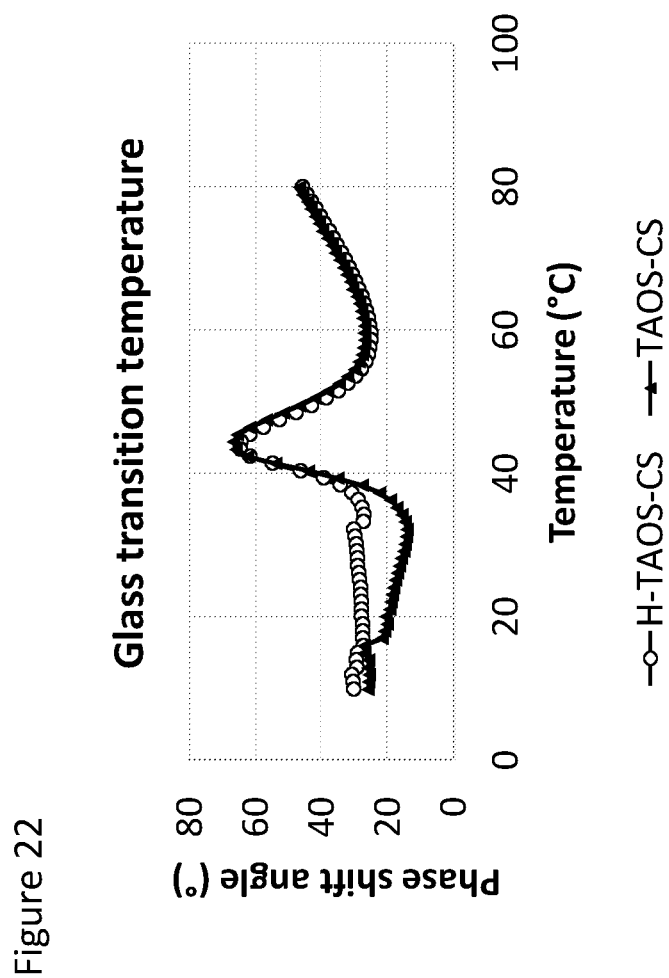

FIG. 22—Shows phase shift angle vs temperature traces for H-TAOS-CS scaffolds versus TAOS-CS scaffold.

FIG. 23—Storage and Loss modulus vs temperature traces TAOS-CS scaffolds (A) versus H-TAOS-CS scaffold (B).

Figure 24:
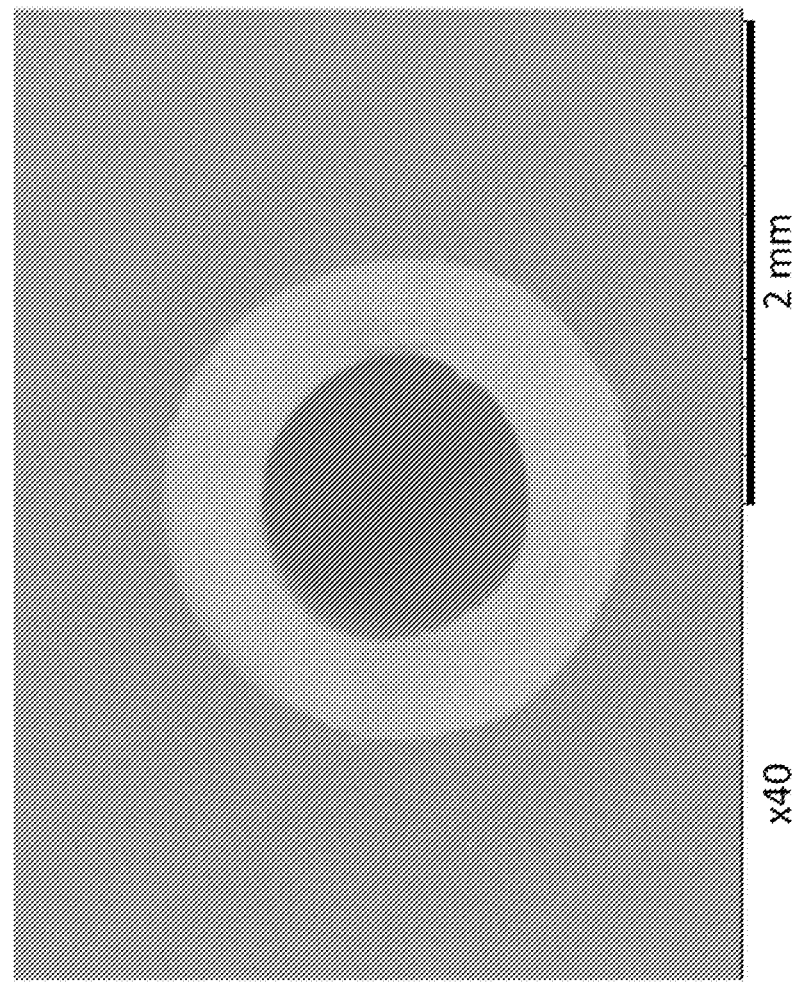

FIG. 24—Shows a SEM image of a hollow PLGA pellet (non-ceramic).

Figure 25:
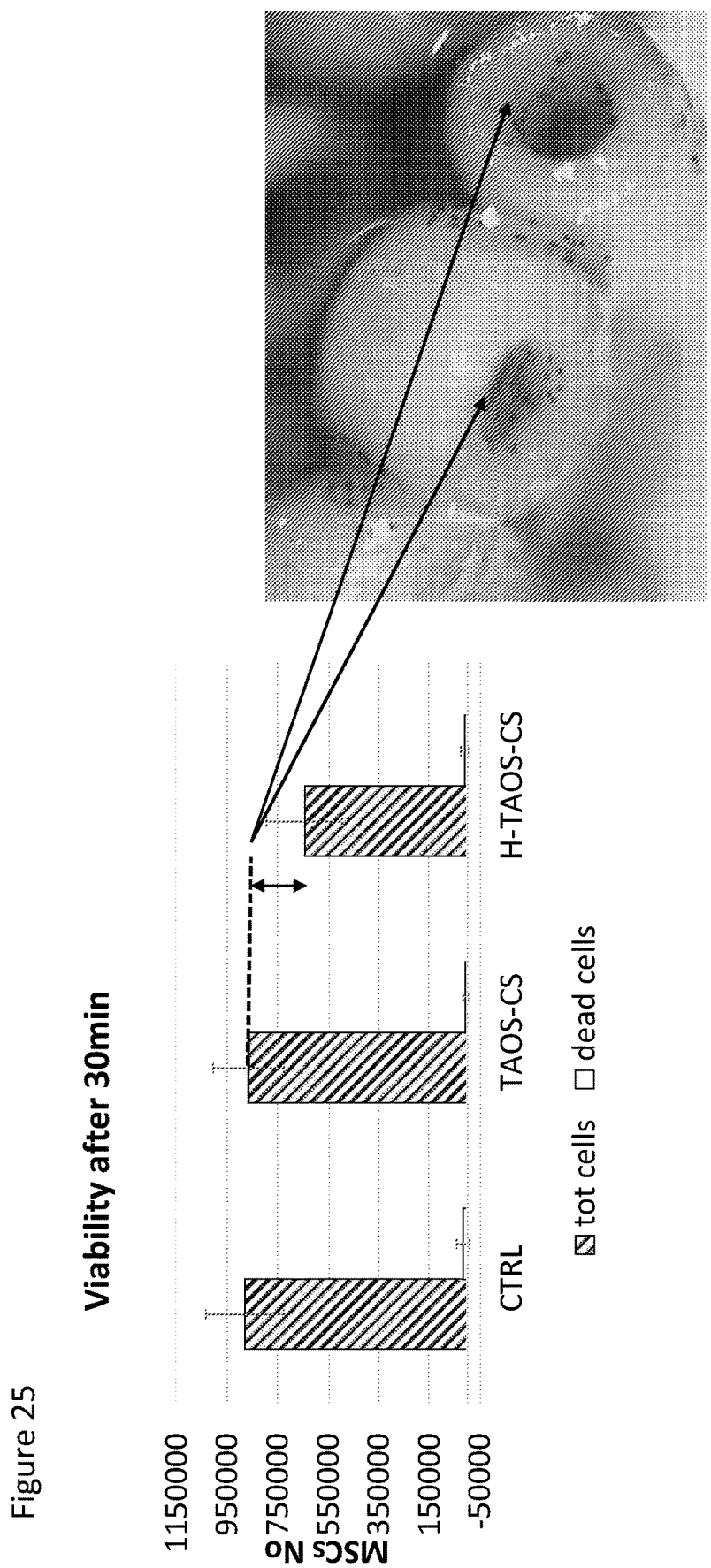

FIG. 25—Shows MSCs viability after 30 min with hollow TAOS-CS scaffolds.

Figure 26:
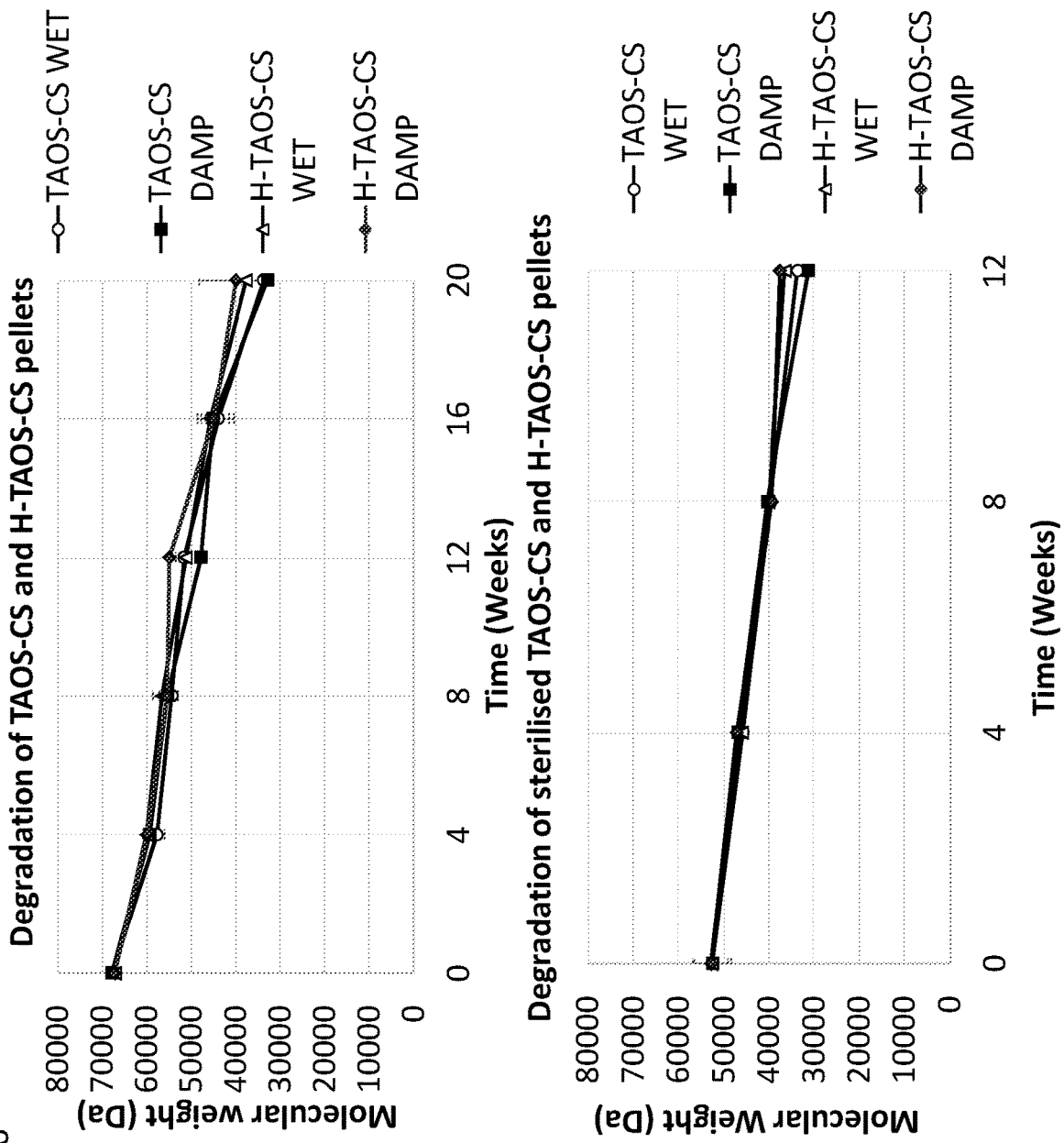

FIG. 26—Unsterile and e-beam (25 kGy) sterilised TAOS-CS and H-TAOS-CS pellets were investigated for degradation. TAOS-CS and H-TAOS-CS pellets were used to prepare scaffolds in open cell Sawbone™ in both wet (immersed in sterile PBS) and damp (sealed in box surrounded by PBS soaked tissue) conditions. For each test condition, 200 mg of pellets (n=2) were used. Pellets degradation was evaluated by gel permeation chromatography (GPC) to assess the variation of PLGA molecular weight overtime.

DETAILED DESCRIPTION

Definitions

The term "scaffold material" is intended to refer to a composition that is capable of forming a scaffold, i.e. a pre-scaffold material. For example the scaffold material may comprise a composition that is capable of setting into a scaffold. The scaffold material itself may or may not have a structure of a scaffold until the scaffold material has formed the scaffold according to the methods herein. Reference to "a composition that is capable of forming a scaffold" may include the capability to form a scaffold with no further intervention/process steps and/or components. In an alternative embodiment, reference to "a composition that is capable of forming a scaffold" may include the capability to form a scaffold following further intervention/process steps according to the invention herein and/or following addition of components according to the invention herein.

The term "scaffold" (may be interchanged with the term "matrix") is understood to mean a solid mass of material having a 3-dimensional structure, which may for example be suitable to support cells. In embodiments of the invention, the scaffold may be porous, having interconnected pores or gaps.

The term "room temperature" is intended to refer to a temperature of from about 15° C. to about 25° C., such as from about 20° C. to about 25° C.

The term "setting" herein is intended to refer to the act of solidifying, or otherwise fixing, the scaffold material into a solid scaffold. The setting may be actively promoted, for example by a change in conditions, such as temperature and/or pressure. In one embodiment, setting is achieved by sintering. In one embodiment, setting is achieved by addition of a setting agent and/or condition. In another embodiment, the setting of the scaffold material into a solid scaffold may be a passive step, for example the hollow pellets of the scaffold material may spontaneously interlink upon contact. This may be immediate interlinking upon contact, or for example over a period of time. In one embodiment, the setting may be facilitated by leaching of plasticiser from the hollow particles. Setting may be facilitated by administration/implantation to a body or tissue.

The term "sintering" herein is intended to refer to a process of compacting and forming a solid mass of material by heat and/or pressure without melting it to the point of liquefaction. For example, sintering can happen naturally in mineral deposits.

The term "solidifying" or "solidify" herein is intended to refer to the change of state from a flowable state (for example, that may take the shape of a receptacle) to a non-flowable state where the pellets and/or particles of the scaffold material are interconnected and set in position relative to each other. For the purposes of the present invention a putty or gel material may be considered a solidified material. The term "flowable" may include liquid or solid particles, pellets or powder that are not interconnected and are capable of flowing.

A "plasticiser" is a substance typically incorporated into a polymer to increase its flexibility, softness, distensibility or workability. Plasticizers can weaken the bonds holding the polymer molecules together and can have an effect on thermal and/or mechanical properties. The plasticiser may be a pharmaceutically acceptable plasticiser. The plasticiser may be a polymer solvent, such as ethanol, for example a solvent of the polymers described herein.

The terms "inter-link" or "interlinking" are intended to refer to the pellets becoming physically connected and held together (i.e. interacting and sticking together). Inter-linking may be achieved by covalent, non-covalent, electrostatic, ionic, adhesive, cohesive or entanglement interactions between the hollow polymer pellets or components of the hollow polymer pellets. The pellets may be crosslinked.

According to a first aspect of the present invention, there is provided a scaffold material composition for forming a solid tissue scaffold, the composition comprising a plurality of hollow polymer pellets, each pellet comprising an open hollow extending through the pellet, and
wherein the plurality of hollow polymer pellets are capable of interlinking and setting into a solid scaffold.

The hollow polymer pellets may comprise an open hollow. For example, a hollow in a structure that is open at at least one end or side, i.e. not a hollow that is completely enclosed within the structure of the pellet. For example, the hollow polymer pellets may have a tubular structure, with the hollow extending therethrough. The hollow tube may be open at one end or more preferably at both ends of the pellet structure. The invention also envisages a hollow in the form of a channel running through a pellet structure, whereby the channel may be open substantially along its length, i.e. as an alternative to a hollow tube structure having a generally O-shaped hollow cross section the hollow polymer pellets may comprise a C-shaped or U-shaped cross-section such that the hollow channel is open substantially along it length. In one embodiment, the hollow polymer pellets are tubular in structure and open at both ends. The hollow polymer pellets may comprise substantially parallel walls (for example in the sense that opposite walls of a tube are generally parallel to each other). The hollow polymer pellets may not comprise or consist of hollow microspheres (e.g. substantially spherical particles with a substantially hollow core).

The hollow polymer pellets may be tubular. In one embodiment, the hollow polymer pellets are tubular with a substantially circular cross-section. Alternatively, the hollow polymer pellets may be any suitably shaped cross-section, such as circular, triangular, square, semi-circular, pentagonal, hexagonal, heptagonal, octagonal, or the like. In one embodiment wherein the hollow polymer pellets are tubular, the outer surface of the hollow polymer pellets may be substantially circular in cross-section and the inner surface of the hollow polymer pellets may be substantially circular in cross-section. In another embodiment, the cross-sectional shape of the outer surface may be different to the cross-sectional shape of the inner surface. For example, the outer surface may be circular in cross-section, and the inner surface may be square in cross-section, or vice versa. In an example where the hollow polymer pellets are formed by extrusion, the cross-sectional shape of the inner and outer surfaces of the tube-like structure may be determined by the shape of the extrusion die.

The hollow polymer pellets may have a length that is equal to or greater than their diameter. In one embodiment, the length is greater than the diameter. The length of the hollow polymer pellets may be uniform in the composition of hollow polymer pellets or a population of hollow polymer pellets in a composition may be irregular in length relative to each other.

The hollow polymer pellets may have a size in their longest dimension of between about 300 and about 700 µm. In another embodiment, the hollow polymer pellets may have a size in their longest dimension of between about 300 and about 600 µm. In another embodiment, the hollow polymer pellets may have a size in their longest dimension of between about 300 and about 550 µm. In another embodiment, the hollow polymer pellets may have a size in their longest dimension of between about 300 and about 500 µm. In another embodiment, the hollow polymer pellets may have a size in their longest dimension of between about 400 and about 600 µm. In another embodiment, the hollow polymer pellets may have a size in their longest dimension of between about 400 and about 550 µm. In another embodiment, the hollow polymer pellets may have a size in their longest dimension of between about 400 and about 500 µm. In another embodiment, the hollow polymer pellets may have a size in their longest dimension of between about 450 and about 500 µm. In another embodiment, the hollow polymer pellets may have a size in their longest dimension of about 500 µm.

In another embodiment, the hollow polymer pellets may have a size in their longest dimension of between about 50 and about 700 µm. In another embodiment, the hollow polymer pellets may have a size in their longest dimension of between about 50 and about 500 µm. In another embodiment, the hollow polymer pellets may have a size in their longest dimension of between about 50 and about 300 µm. In another embodiment, the hollow polymer pellets may have a size in their longest dimension of between about 50 and about 200 µm. In another embodiment, the hollow polymer pellets may have a size in their longest dimension of between about 50 and about 100 µm.

The external diameter of the hollow polymer pellets (i.e. the distance between opposing outer surfaces (e.g. external/outer diameter of a tube) may be between about 200 and about 600 µm. In another embodiment, the external diameter of the hollow polymer pellets (i.e. the distance between opposing outer surfaces (e.g. external/outer diameter of a tube) may be between about 50 and about 600 µm. In another embodiment, the external diameter of the hollow polymer pellets (i.e. the distance between opposing outer surfaces (e.g. external/outer diameter of a tube) may be between about 50 and about 500 µm. In another embodiment, the external diameter of the hollow polymer pellets (i.e. the distance between opposing outer surfaces (e.g. external/outer diameter of a tube) may be between about 50 and about 400 µm. In another embodiment, the external diameter of the hollow polymer pellets (i.e. the distance between opposing outer surfaces (e.g. external/outer diameter of a tube) may be between about 50 and about 300 µm. In another embodiment, the external diameter of the hollow polymer pellets (i.e. the distance between opposing outer surfaces (e.g. external/outer diameter of a tube) may be between about 50 and about 200 µm.

The internal diameter of the hollow polymer pellets (i.e. the distance between opposing inner surfaces (e.g. internal diameter of a tube) may be between about 100 and about 300 µm. In another embodiment, the internal diameter of the hollow polymer pellets (i.e. the distance between opposing inner surfaces (e.g. internal diameter of a tube) may be between about 10 and about 300 µm. In another embodiment, the internal diameter of the hollow polymer pellets (i.e. the distance between opposing inner surfaces (e.g. internal diameter of a tube) may be between about 20 and about 300 µm. In another embodiment, the internal diameter of the hollow polymer pellets (i.e. the distance between opposing inner surfaces (e.g. internal diameter of a tube) may be between about 10 and about 200 µm. In another embodiment, the internal diameter of the hollow polymer pellets (i.e. the distance between opposing inner surfaces (e.g. internal diameter of a tube) may be between about 20 and about 200 µm. In another embodiment, the internal diameter of the hollow polymer pellets (i.e. the distance between opposing inner surfaces (e.g. internal diameter of a tube) may be between about 10 and about 100 µm. In another embodiment, the internal diameter of the hollow polymer pellets (i.e. the distance between opposing inner surfaces (e.g. internal diameter of a tube) may be between about 20 and about 100 µm. In another embodiment, the internal diameter of the hollow polymer pellets (i.e. the distance between opposing inner surfaces (e.g. internal diameter of a tube) may be between about 20 and about 50 µm. In another embodiment, the internal diameter of the hollow polymer pellets may be about 200 µm. In another embodiment, the internal diameter of the hollow polymer pellets (i.e. the distance between opposing inner surfaces (e.g. internal diameter of a tube) may be at least about 20 µm. In another embodiment, the internal diameter of the hollow polymer pellets (i.e. the distance between opposing inner surfaces (e.g. internal diameter of a tube) may be at least about 40 µm. In another embodiment, the internal diameter of the hollow polymer pellets (i.e. the distance between opposing inner surfaces (e.g. internal diameter of a tube) may be at least about 50 µm. In another embodiment, the internal diameter of the hollow polymer pellets (i.e. the distance between opposing inner surfaces (e.g. internal diameter of a tube) may be at least about 800 µm. In another embodiment, the internal diameter of the hollow polymer pellets (i.e. the distance between opposing inner surfaces (e.g. internal diameter of a tube) may be at least about 100 µm. In another embodiment, the internal diameter of the hollow polymer pellets (i.e. the distance between opposing inner surfaces (e.g. internal diameter of a tube) may be at least about 150 µm. In another embodiment, the internal diameter of the hollow polymer pellets (i.e. the distance between opposing inner surfaces (e.g. internal diameter of a tube) may be at least about 200 µm. Such hollow/lumen sizes allow for advantageous cell infiltration into the hollow polymer pellets.

The thickness of the walls of the hollow polymer pellets may be between about 100 and 200 µm. In another embodiment, the thickness of the walls of the hollow polymer pellets may be between about 10 µm and 200 µm. In another embodiment, the thickness of the walls of the hollow polymer pellets may be between about 10 and 100 µm. In another embodiment, the thickness of the walls of the hollow polymer pellets may be between about 10 and 80 µm. In another embodiment, the thickness of the walls of the hollow polymer pellets may be between about 10 and 50 µm. In another embodiment, the thickness of the walls of the hollow polymer pellets may be between about 10 and 40 µm. In another embodiment, the thickness of the walls of the hollow polymer pellets may be between about 10 and 30 µm. In another embodiment, the thickness of the walls of the hollow polymer pellets may be between about 20 and 100 µm. In another embodiment, the thickness of the walls of the hollow polymer pellets may be between about 20 and 80 µm. In another embodiment, the thickness of the walls of the hollow polymer pellets may be between about 20 and 50 µm. In another embodiment, the thickness of the walls of the hollow polymer pellets may be between about 20 and 30 µm.

In one embodiment, the hollow polymer pellets may have an external diameter of 50-200 µm, an internal diameter of 20-170 µm, and optionally a wall thickness of at least 30 µm. In one embodiment, the hollow polymer pellets may have an external diameter of 50-200 µm, an internal diameter of 20-190 µm, and optionally a wall thickness of 10 µm. In one embodiment, the hollow polymer pellets may have an external diameter of 50-200 µm, an internal diameter of 20-170 µm, and optionally a wall thickness of 30 µm. In one embodiment, the hollow polymer pellets may have an external diameter of 50-500 µm, an internal diameter of 20-370 µm, and optionally a wall thickness of at least 30 µm.

In one embodiment, the hollow polymer pellets of the desired size may be unable to pass through a sieve or filter with a pore size of about 400 µm, but will pass through a sieve or filter with a pore size of about 500 µm. In another embodiment, the hollow polymer pellets of the desired size may be unable to pass through a sieve or filter with a pore size of about 400 µm, but will pass through a sieve or filter with a pore size of about 600 µm. In another embodiment, the hollow polymer pellets of the desired size may be unable to pass through a sieve or filter with a pore size of about 400 µm, but will pass through a sieve or filter with a pore size of about 800 µm. In one embodiment, the hollow polymer pellets of the desired size may be unable to pass through a sieve or filter with a pore size of about 300 µm, but will pass through a sieve or filter with a pore size of about 500 µm. In another embodiment, the hollow polymer pellets of the desired size may be unable to pass through a sieve or filter with a pore size of about 300 µm, but will pass through a sieve or filter with a pore size of about 600 µm. In another embodiment, the hollow polymer pellets of the desired size may be unable to pass through a sieve or filter with a pore size of about 300 µm, but will pass through a sieve or filter with a pore size of about 800 µm.

In one embodiment, the hollow (or otherwise "lumen") of the hollow polymer pellets may be at least 10% of the volume of the hollow polymer pellets. In another embodiment, the hollow of the hollow polymer pellets may be at least 20% of the volume of the hollow polymer pellets. In another embodiment, the hollow of the hollow polymer pellets may be at least 30% of the volume of the hollow polymer pellets. In another embodiment, the hollow of the hollow polymer pellets may be at least 40% of the volume of the hollow polymer pellets. In another embodiment, the hollow of the hollow polymer pellets may be at least 50% of the volume of the hollow polymer pellets. Such hollow/lumen volumes allow for advantageous cell infiltration into the hollow polymer pellets.

The size, length, diameter, volume or thickness of the hollow polymer pellets, or features thereof, may refer to the average size of a population of hollow polymer pellets. In one embodiment, the size, length, diameter, volume or thickness of the hollow polymer pellets, or features thereof, may refer to the largest size, length, diameter, volume or thickness of the hollow polymer pellet. The size of the hollow polymer pellets may be advantageously chosen by the skilled person for the intended application or type of scaffold required. For example, the use of larger sized hollow polymer pellets may be for increased porosity, where the gaps between the hollow polymer pellets may be larger relative to the use of smaller hollow polymer pellets. Such size control can provide control over the agent release rate, whereby a faster release rate may be provided by the choice of larger hollow polymer pellets. For example when extruding the hollow polymer pellet material, the draw-off rate can be changed pull the hollow polymer pellets into thinner diameters. Additionally, morphology can be influenced by a change in temperature and thus cooling time.

The hollow polymer pellets may be solid (with the exception of the hollow itself), that is the material of the hollow polymer pellet may be solid without a porous structure. Alternatively, the hollow polymer pellets may be comprised of porous material, such that the walls of the hollow polymer pellet structure are porous.

The hollow polymer pellets may comprise or consist of one or more polymer. The polymer(s) may be synthetic polymer(s). The hollow polymer pellets may comprise one or more polymer selected from the group comprising poly (α-hydroxyacids) including poly (D,L-lactide-co-glycolide) (PLGA), poly D,L-lactic acid (PDLLA), polyethyleneimine (PEI), polylactic or polyglcolic acids, poly-lactide polyglycolide copolymers, and poly-lactide poly-glycolide polyethylene glycol copolymers, polyethylene glycol (PEG), polyesters, poly (ε-caprolactone), poly (3-hydroxy-butyrate), poly (s-caproic acid), poly (p-dioxanone), poly (propylene fumarate), poly (ortho esters), polyol/diketene acetals addition polymers, polyanhydrides, poly (sebacic anhydride) (PSA), poly (carboxybiscarboxyphenoxyphosphazene) (PCPP), poly [bis (p-carboxyphenoxy) methane]

(PCPM), copolymers of SA, CPP and CPM (as described in Tamat and Langer in Journal of Biomaterials Science Polymer Edition, 3, 315-353. 1992 and by Domb in Chapter 8 of The Handbook of Biodegradable Polymers, Editors Domb A J and Wiseman R M, Harwood Academic Publishers), poly (amino acids), poly (pseudo amino acids), polyphosphazenes, derivatives of poly [(dichloro) phosphazene], poly [(organo) phosphazenes], polyphosphates, polyethylene glycol polypropylene block co-polymers for example that sold under the trade mark Pluronics™, natural or synthetic polymers such as silk, elastin, chitin, chitosan, fibrin, fibrinogen, polysaccharides (including pectins), alginates, collagen, peptides, polypeptides or proteins, copolymers prepared from the monomers of any of these polymers, random blends of these polymers, any suitable polymer and mixtures or combinations thereof.

The hollow polymer pellets may comprise polymer selected from the group comprising poly(α-hydroxyacids) such as poly lactic acid (PLA), polyglycolic acid (PGA), poly(D,L-lactide-co-glycolide)(PLGA), poly D, L-lactic acid (PDLLA), poly-lactide poly-glycolide copolymers, and combinations thereof. In one embodiment, the hollow polymer pellets comprise or consist of PLGA. In one embodiment, the hollow polymer pellets comprise only one polymer, such as PLGA.

The hollow polymer pellets may comprise polymer which is a blend of a poly(α-hydroxyacid) with poly(ethylene glycol) (PEG), such as a blend of a polymer or copolymer based on glycolic acid and/or lactic acid with PEG. The hollow polymer pellets may comprise PLGA/PEG. The hollow polymer pellets may comprise PEG, for example as a plasticiser. In another embodiment, the hollow polymer pellets may not comprise PEG. In another embodiment, the hollow polymer pellets may be substantially free of PEG, for example, the hollow polymer pellets may comprise less than 2% w/w PEG. In another embodiment, the hollow polymer pellets may comprise less than 1.5% w/w PEG. In another embodiment, the hollow polymer pellets may comprise less than 1% w/w PEG. In another embodiment, the hollow polymer pellets may comprise less than 0.5% w/w PEG. In another embodiment, the hollow polymer pellets may comprise less than 0.2% w/w PEG.

In one embodiment, the hollow polymer pellets comprises PLGA 95:5. Alternatively, the hollow polymer pellets may comprise PLGA 50:50. Alternatively, the hollow polymer pellets may comprise PLGA 85:15. Alternatively, the hollow polymer pellets may comprise any PLGA between PLGA 85:15 and PLGA 95:5. Alternatively, the hollow polymer pellets may comprise PLGA 65:35. Alternatively, the hollow polymer pellets may comprise PLGA 72:25. PLGA having monomer ratios between the above PLGA embodiments may also be considered.

In embodiments wherein PEG is provided as a plasticiser in the hollow polymer pellets, the PEG may be up to 10% of the hollow polymer pellet content. Alternatively, the PEG may be up to 8% of the hollow polymer pellet content. Alternatively, the PEG may be up to 6% of the hollow polymer pellet content. Alternatively, the PEG may be up to 3% of the hollow polymer pellet content. Alternatively, the PEG may be up to 2% of the hollow polymer pellet content. Alternatively, the PEG may be up to 1% of the hollow polymer pellet content. Alternatively, the PEG may be between 1 and 10% of the hollow polymer pellet content. Alternatively, the PEG may be between 5 and 8% of the hollow polymer pellet content. Alternatively, the PEG may be between 6 and 7% of the hollow polymer pellet content. Alternatively, the PEG may be between 2 and 6% of the hollow polymer pellet content. Alternatively, the PEG may be between 3 and 4% of the hollow polymer pellet content. Alternatively, the PEG may be about 6.5% of the hollow polymer pellet content.

In embodiments wherein PEG is provided as a plasticiser in the hollow polymer pellets, the PEG may have a molecular weight of 1000 Da or less. The PEG may have a molecular weight of between 400 Da and 1000 Da. Alternatively the PEG is 800 Da or less. Alternatively the PEG is 600 Da or less. In one embodiment, the PEG is PEG400. In one embodiment, the hollow polymer pellets comprise liquid PEG400, optionally wherein the PEG400 is provided at an amount of 1-40% w/w. In one embodiment, the hollow polymer pellets comprise liquid PEG400, optionally wherein the PEG400 is provided at an amount of 1-30% w/w. In one embodiment, the hollow polymer pellets comprise liquid PEG400, optionally wherein the PEG400 is provided at an amount of 1-20% w/w. In one embodiment, the hollow polymer pellets comprise liquid PEG400, optionally wherein the PEG400 is provided at an amount of 1-15% w/w.

The hollow polymer pellets may comprise a plasticiser, which may or may not be PEG. The plasticiser may comprise PLGA, such as low molecular weight PLGA, for example less than 10 KDa PLGA. Additionally or alternatively, the plasticiser may comprise the monomers of PLGA (i.e. DL-lactide and/or glycolide).

The hollow polymer pellets may comprise a plasticiser selected from any of glycerine, polyethylene glycols, polyethylene glycol monomer ether, propylene glycol, sorbitol sorbitan solution, acetyl tributyl citrate, acetyl triethyl citrate, castor oil, diacetyl monoglycerides, dibutyl sebacate, diethyl phthalate, triacetin, tributyl citrate, triethyl citrate, or combinations thereof, optionally wherein the plasticisers are provided in an amount of 1-10% w/w.

The hollow polymer pellets may comprise a plasticiser selected from any of glycerine, polyethylene glycols, polyethylene glycol monomer ether, propylene glycol, sorbitol sorbitan solution, or combinations thereof, optionally wherein the plasticisers are provided in an amount of 1-10% w/w. The hollow polymer pellets may comprise a plasticiser selected from any of acetyl tributyl citrate, acetyl triethyl citrate, castor oil, diacetyl monoglycerides, dibutyl sebacate, diethyl phthalate, triacetin, tributyl citrate, triethyl citrate, or combinations thereof, optionally wherein the plasticisers are provided in an amount of 1-10% w/w.

In other embodiments, the plasticiser may be provided in an amount of up to 40% w/w. In other embodiments, the plasticiser may be provided in an amount of up to 30% w/w. In another embodiment, the plasticiser may be provided in an amount of 1-40% w/w. In another embodiment, the plasticiser may be provided in an amount of 1-30% w/w. In another embodiment, the plasticiser may be provided in an amount of 1-20% w/w. In another embodiment, the plasticiser may be provided in an amount of 1-15% w/w. In another embodiment, the plasticiser may be provided in an amount of 2-40% w/w. In another embodiment, the plasticiser may be provided in an amount of 2-30% w/w. In another embodiment, the plasticiser may be provided in an amount of 2-20% w/w.

The hollow polymer pellets may be biocompatible and/or biodegradable. By controlling the polymers used in the hollow polymer pellets the rate of scaffold degradation may be controlled.

Scaffold Material

In one embodiment, the scaffold material comprises a carrier, for example the hollow polymer pellets suspended in a carrier as described herein.

The scaffold material may comprise one or more types of hollow polymer pellets made from one or more type of polymer. The scaffold material may further comprise one or more types of polymer particles made from one or more type of polymer, such as the polymers or polymer blends listed herein. The polymer particles may be made of the same material as the hollow polymer pellets.

Furthermore, the scaffold material may further comprise natural-polymer particles or non-polymer particles. The natural-polymer particles or non-polymer particles may be microparticles. The non-polymer particles may comprise or consist of ceramic. The ceramic may comprise or consist of calcium sulphate (CS) or β-tricalcium phosphate (β-TCP). In another embodiment, the natural-polymer particles or non-polymer particles may comprise crystallised sugar molecules, such as crystallised particles of mannitol. Other sugar particles may be provided, such as glucose. In one embodiment, the natural-polymer particles or non-polymer particles may comprise anti-oxidant. In one embodiment, the natural-polymer particles or non-polymer particles may comprise silica substituted ceramics. In one embodiment, the natural-polymer particles or non-polymer particles may comprise α-tricalcium phosphate. In one embodiment, the natural-polymer particles or non-polymer particles may comprise hydroxyapatite. In one embodiment, the natural-polymer particles or non-polymer particles may comprise calcium phosphate. Combinations of different natural-polymer particles or non-polymer particles may be considered.

The natural-polymer particles or non-polymer particles may be substantially similar or equal in size (according to an average particle size in a population) relative to the hollow polymer pellets. In another embodiment, the natural-polymer particles or non-polymer particles may be smaller in size (according to an average particle size in a population) relative to the hollow polymer pellets. For example, in one embodiment, the natural-polymer particles or non-polymer particles may be in powder form. A powder form may comprise particles of less than about 250 microns according to an average particle size in a population. In another embodiment, a powder form may comprise particles of less than about 150 microns according to an average particle size in a population. In another embodiment, a powder form may comprise particles of between about 20 and 250 microns according to an average particle size in a population.

In one embodiment, the natural-polymer or non-polymer particles are encapsulated within the hollow polymer pellets. In one embodiment, the natural-polymer or non-polymer particles are in powder form and encapsulated within the hollow polymer pellets. The skilled person will understand that the natural-polymer or non-polymer particles may be of any suitable size for encapsulation within the hollow polymer pellets. The encapsulation may be provided by the formation of the hollow polymer pellets in the presence of the natural-polymer or non-polymer particle, such as ceramic. For example, the encapsulation may occur through co-extrusion of the polymer for forming the hollow polymer pellets and the natural-polymer or non-polymer particles, such as ceramic. For example, the encapsulation may occur through co-extrusion of the polymer for forming the hollow polymer pellets and the natural-polymer or non-polymer particles, such as ceramic. The non-polymer particles may be provided within the hollow polymer pellets according to the methods of the invention herein.

The scaffold material may comprise between 1% and 55% natural-polymer or non-polymer particles, such as ceramic. In another embodiment, the scaffold material may comprise between 1% and 50% natural-polymer or non-polymer particles, such as ceramic. In another embodiment, the scaffold material may comprise between 10% and 50% natural-polymer or non-polymer particles, such as ceramic. In another embodiment, the scaffold material may comprise between 20% and 50% natural-polymer or non-polymer particles, such as ceramic. In another embodiment, the scaffold material may comprise between 30% and 50% natural-polymer or non-polymer particles, such as ceramic. In another embodiment, the scaffold material may comprise between 40% and 50% natural-polymer or non-polymer particles, such as ceramic.

In an embodiment wherein the natural-polymer or non-polymer particles are encapsulated within the hollow polymer pellets the hollow polymer pellets may comprise between 1% and 55% (w/w) of natural-polymer or non-polymer particles, such as ceramic. Alternatively, in an embodiment wherein the natural-polymer or non-polymer particles are encapsulated within the hollow polymer pellets the hollow polymer pellets may comprise between 20% and 55% (w/w) of natural-polymer or non-polymer particles, such as ceramic. Alternatively, in an embodiment wherein the natural-polymer or non-polymer particles are encapsulated within the hollow polymer pellets the hollow polymer pellets may comprise between 20% and 50% (w/w) of natural-polymer or non-polymer particles, such as ceramic. Alternatively, in an embodiment wherein the natural-polymer or non-polymer particles are encapsulated within the hollow polymer pellets the hollow polymer pellets may comprise between 30% and 50% (w/w) of natural-polymer or non-polymer particles, such as ceramic. Alternatively, in an embodiment wherein the natural-polymer or non-polymer particles are encapsulated within the hollow polymer pellets the hollow polymer pellets may comprise between 40% and 50% (w/w) of natural-polymer or non-polymer particles, such as ceramic.

In an embodiment wherein natural-polymer or non-polymer particles, such as ceramic, are provided in the scaffold material, the scaffold material may comprise less than 40% w/v plasticiser in the carrier. In another embodiment wherein natural-polymer or non-polymer particles, such as ceramic, are provided in the scaffold material, the scaffold material may comprise less than 39% w/v plasticiser in the carrier. In another embodiment wherein natural-polymer or non-polymer particle, such as ceramic, are provided in the scaffold material, the scaffold material may comprise less than 35% w/v plasticiser in the carrier. In another embodiment wherein natural-polymer or non-polymer particle, such as ceramic, are provided in the scaffold material, the scaffold material may comprise less than 30% w/v plasticiser in the carrier. Alternatively, the plasticiser content may be less than 20%, 15%, 10% or 5% w/v of the carrier. In an embodiment wherein natural-polymer or non-polymer particles, such as ceramic, are provided in the scaffold material, the scaffold material may comprise about 1% w/v plasticiser in the carrier.

Where more than one type of hollow polymer pellet is used each hollow polymer pellet type may have a different solidifying or setting property. For example, the hollow polymer pellets may be made from similar polymers but may have different gelling pHs or different melting temperatures or glass transition points.

In one embodiment, in order for the hollow polymer pellets to form a scaffold the temperature around the hollow polymer pellets, for example in the human or non-human animal where the composition is administered, is approximately equal to, or greater than, the glass transition temperature of the hollow polymer pellets. At such temperatures the hollow polymer pellets may inter-link to one or more other hollow polymer pellets to form a scaffold. By inter-link it is meant that adjacent hollow polymer pellets become joined together. For example, the hollow polymer pellets may inter-link due to entanglement of the polymer chains at the surface of one hollow polymer pellet with polymer chains at the surface of another hollow polymer pellet. There may be adhesion, cohesion or fusion between adjacent hollow polymer pellets.

The scaffold material may comprise hollow polymer pellets which are formed of a polymer or a polymer blend that has a glass transition temperature (Tg) either close to or just above body temperature (such as from about 30° C. to 45° C., e.g. from about 35° C. to 40° C., for example from about 37° C. to 40° C.). Accordingly, at room temperature the hollow polymer pellets are below their Tg and behave as discrete hollow polymer pellets, but in the body the hollow polymer pellets soften and interact/stick to their neighbours. Preferably scaffold formation begins within 15 minutes of the raise in temperature from room to body temperature.

The hollow polymer pellets may be formed from a polymer which has a Tg from about 35° C. to 40° C., for example from about 37° C. to 40° C., wherein the polymer is a poly(α-hydroxyacid) (such as PLA, PGA, PLGA, or PDLLA or a combination thereof), or a blend thereof with poly(ethylene glycol) (PEG). At body temperature these hollow polymer pellets may interact to from a scaffold. The scaffold material may comprise only poly(α-hydroxyacid)/PEG hollow polymer pellets or other particle/pellet types may be included.

The hollow polymer pellets may be formed from a blend of poly(D,L-lactide-co-glycolide)(PLGA) and poly(ethylene glycol) (PEG) which has a Tg at or above body temperature. At body temperature these hollow polymer pellets can interact to from a scaffold, and during this process PEG may be lost from the surface of the hollow polymer pellets which will have the effect of raising the Tg and hardening the scaffold structure. The scaffold material may comprise only PLGA/PEG hollow polymer pellets or other particle/pellet types may be included. In another embodiment, the scaffold material may comprise only PLGA hollow polymer pellets. In another embodiment, the scaffold material, such as the polymer hollow polymer pellets, may be substantially free of plasticiser, such as PEG.

Advantageously, providing hollow polymer pellets which are substantially free of plasticiser, such as PEG, provides a leaner manufacturing process and improves the room temperature stability of the hollow polymer pellets. For example, due to the low glass transition temperatures of typical hollow polymer pellets, such as PLGA/PEG400 blends, they need to be stored in a fridge or freezer. In contrast hollow polymer pellets which are substantially free of plasticiser would be capable of storage at room temperature. Such plasticiser free hollow polymer pellets may still be capable of setting into a scaffold with use of plasticisers in a carrier as described herein.

The scaffold material may comprise a mixture of temperature sensitive hollow polymer pellets and non-temperature sensitive hollow polymer pellets or particles. Preferably non temperature sensitive particles are hollow polymer pellets/particles with a glass transition temperature which is above the temperature at which the composition is intended to be used. In a composition comprising a mixture of temperature sensitive hollow polymer pellets and non-temperature sensitive hollow polymer pellets/particles the ratio of temperature sensitive hollow polymer pellets to non-temperature sensitive hollow polymer pellets/particles may be about 3:1, or lower, for example, 4:3. The temperature sensitive hollow polymer pellets may be capable of inter-linking to each other when the temperature of the composition is raised to or above the glass transition a temperature of these hollow polymer pellets. By controlling the ratio of temperature sensitive hollow polymer pellets to non-temperature sensitive hollow polymer pellets/particles it may be possible to manipulate the porosity of the resulting scaffold.

Reference to temperature sensitivity may refer to temperature sensitivity at temperatures of less than 200° C. In another embodiment, reference to temperature sensitivity may refer to temperature sensitivity at temperatures of less than 180° C. In another embodiment, reference to temperature sensitivity may refer to temperature sensitivity at temperatures of less than 150° C. In another embodiment, reference to temperature sensitivity may refer to temperature sensitivity at temperatures of less than 120° C. In another embodiment, reference to temperature sensitivity may refer to temperature sensitivity at temperatures of less than 100° C. In another embodiment, reference to temperature sensitivity may refer to temperature sensitivity at temperatures of less than 80° C. In another embodiment, reference to temperature sensitivity may refer to temperature sensitivity at temperatures of less than 60° C. In another embodiment, reference to temperature sensitivity may refer to temperature sensitivity at temperatures of less than 50° C. In another embodiment, reference to temperature sensitivity may refer to temperature sensitivity at temperatures of less than 45° C. In another embodiment, reference to temperature sensitivity may refer to temperature sensitivity at temperatures of less than 40° C.

In one embodiment, ceramic particles may additionally be present in the scaffold material. This will typically be a temperature insensitive particle type. Alternatively or additionally, hollow polymer pellets in the scaffold material may themselves contain a ceramic component. This will typically be a temperature insensitive particle type. The inclusion of ceramic material either as separate particles or within the hollow polymer pellets may enhance osteoconductivity and/or add osteoinductivity.

The hollow polymer pellets may be provided dry, for example prior to mixing with any carrier. The hollow polymer pellets may be at least partially dispersible in the carrier. The hollow polymer pellets may not be soluble in the carrier at a temperature of 37° C. or less.

The scaffold material may be for use in a method of treatment of the human or animal body by surgery or therapy or in a diagnostic method practised on the human or animal body. The scaffold material may be for pharmaceutical use or may be for use in cosmetic surgery.

In one embodiment, the scaffold of hollow polymer pellets is porous. The pores may be formed by the hollow structure of each hollow polymer pellet, and additionally by voids within the hollow polymer pellets and/or by gaps between the hollow polymer pellets. In one embodiment, the pores are formed by the hollow structure of each hollow polymer pellet, voids within the polymer microparticles, and by gaps between the polymer microparticles. Pores may be formed by the gaps which are left between hollow polymer pellets used to form the scaffold.

The scaffold may have a pore volume (i.e. porosity) of at least about 30%. In another embodiment, the scaffold may have a pore volume (i.e. porosity) of at least about 35%. In another embodiment, the scaffold may have a pore volume (i.e. porosity) of at least about 40%. In another embodiment, the scaffold may have a pore volume (i.e. porosity) of at least about 50%. In another embodiment, the scaffold may have a pore volume (i.e. porosity) of at least about 60%. In another embodiment, the scaffold may have a pore volume (i.e. porosity) of at least about 65%. In another embodiment, the scaffold may have a pore volume (i.e. porosity) of at least about 70%. In another embodiment, the scaffold may have a pore volume (i.e. porosity) of at least about 55% whilst also maintain a compressive strength of at least 0.5 MPa or at least 0.8 Mpa. In another embodiment, the scaffold may have a pore volume (i.e. porosity) of at least about 55% whilst also maintain a compressive strength of at least 1 MPa. In another embodiment, the scaffold may have a pore volume (i.e. porosity) of at least about 60% whilst also maintain a compressive strength of at least 0.5 MPa or at least 0.8 Mpa. In another embodiment, the scaffold may have a pore volume (i.e. porosity) of at least about 60% whilst also maintain a compressive strength of at least 1 MPa. In another embodiment, the scaffold may have a pore volume (i.e. porosity) of at least about 65% whilst also maintain a compressive strength of at least 0.5 MPa or at least 0.8 Mpa. In another embodiment, the scaffold may have a pore volume (i.e. porosity) of at least about 65% whilst also maintain a compressive strength of at least 1 MPa.

The scaffold may have a Young's modulus of at least about 4 Mpa. In another embodiment, the scaffold may have a Young's modulus of at least about 5 Mpa. In another embodiment, the scaffold may have a Young's modulus of at least about 6 Mpa. In another embodiment, the scaffold may have a Young's modulus of at least about 7 Mpa.

Young's modulus and/or maximum stress may be measured from the stress vs strain traces obtained by an Exponent Stable Micro Systems TA.XT+ texture analyser at about 37° C.

In another embodiment, the scaffold may have a pore volume (i.e. porosity) of at least about 60% whilst also maintain a compressive strength of at least 1 MPa and a Young's modulus of at least 5 Mpa. In another embodiment, the scaffold may have a pore volume (i.e. porosity) of at least about 60% whilst also maintain a compressive strength of at least 1 MPa and a Young's modulus of at least 6 Mpa. In another embodiment, the scaffold may have a pore volume (i.e. porosity) of at least about 70% whilst also maintain a compressive strength of at least 1 MPa and a Young's modulus of at least 5 Mpa. In another embodiment, the scaffold may have a pore volume (i.e. porosity) of at least about 70% whilst also maintain a compressive strength of at least 1 MPa and a Young's modulus of at least 6 Mpa.

Advantageously, the use of hollow polymer pellets to form a scaffold structure provides a high porosity scaffold whilst also maintaining good compressive strength and/or Young's modulus.

The pores may have an average diameter of about 100 microns. The scaffold may have pores in the nanometre to millimetre range. The scaffold may have pores of about 20 to about 50 microns, alternatively between about 50 and 120 microns. In one embodiment, the scaffold has pores with an average size of 100 microns. The scaffold may have at least about 30%, about 40%, about 50% or more pore volume. In one embodiment, the porosity of the scaffold may be between 30% and 70%. In another embodiment, the porosity of the scaffold may be between 40% and 65%. In another embodiment, the porosity of the scaffold may be between 40% and 60%. In another embodiment, the porosity of the scaffold may be between 50% and 60%. The scaffold may have a pore volume of at least 90 mm$^3$ per 300 mm$^3$ of scaffold. In another embodiment, the scaffold may have a pore volume of at least 120 mm$^3$ per 300 mm$^3$ of scaffold. In another embodiment, the scaffold may have a pore volume of at least 150 mm$^3$ per 300 mm$^3$ of scaffold.

As the skilled man would appreciate, pore volume and pore size can be determined using microcomputer tomography (microCT) and/or scanning electron microscopy (SEM). For example, SEM can be carried out using a Philips 535M SEM instrument.

As previously discussed, the high porosity scaffolds have more surface area that gives more space to the cells for growth. Further advantageously, if the hollow polymer pellets are combined with cells, their high surface area allows better cell loading when compared to the non-hollow polymer pellets. If the hollow polymer pellets are combined with cells, their holes protect the cells when shear forces occur. This can be particularly advantageous when mixing the cells and scaffold material where higher viability of the cells can be maintained. Therefore, the hollow polymer pellets provide a shielding effect for cells.

Additionally, the high surface area of the hollow polymer pellets gives another control mechanism for polymer degradation. A higher surface area provided by the hollow polymer pellet structure can result in a faster degradation profile. This can be useful for example in controlled release of active agent by degradation, for example release of surface-bound active or encapsulated active.

The hollow/lumen of the hollow polymer pellets can advantageously be used to influence the resultant pore size distribution of the entire scaffold. It provides a controlled and repeated dimension of pore size within an otherwise broad range of pellet sizes. This approach can be used to either increase the percentage of macropores within the scaffold (e.g. >100 microns or preferably over 250 microns) or microporosity (small lumens to increase percentage of <10 micron pores). Macropores are important for cell infiltration and tissue growth, and microporosity is important for mass transfer.

The provision of hollow polymer pellets can also help prevent the build-up of degradation products within the bulk of the polymer, which can be auto-catalytic or pro-inflammatory when released.

The hollow polymer pellet composition or suspension may be injectable. The injectable scaffold material may be capable of setting (solidifying/self-assembling) upon/or after injection into a subject to form a scaffold. In one embodiment, the scaffold material is intended to be administered by injection into the body of a human or non-human animal. If the scaffold material is injected then the need for invasive surgery to position the scaffold is removed. The scaffold material may be sufficiently viscous to allow administration of the composition to a human or non-human animal, preferably by injection.

By using a scaffold material which solidifies/sets to form a scaffold after administration, a scaffold can be formed which conforms to the shape of where it is placed, for example, the shape of a tissue cavity into which it is placed. This overcomes a problem with scaffolds fabricated prior to administration which must be fabricated to a specific shape ahead of administration, and cannot be inserted through a bottle-neck in a cavity and cannot expand to fill a cavity.

The scaffold material may be arranged to be administered at room temperature. Therefore, the scaffold material may be viscous at room temperature. Alternatively, the scaffold material may be heated to above room temperature, for example to body temperature (about 37° C.) or above, for administration. The scaffold material may be flowable or viscous at this temperature in order to aid its administration to a human or non-human animal.

The scaffold material may have a viscosity which allows it to be administered, using normal pressure (e.g. the pressure can be reasonably applied by the hand of an average person), from a syringe which has an orifice of about 4 mm or less. The size of the orifice will depend on the medical application, for example, for many bone applications a syringe with an orifice of between about 2 mm and about 4 mm will be used, however, for other applications smaller orifices may be preferred. The term "normal pressure" may be pressure that is applied by a human administering the composition to a patient using one hand.

The scaffold material may be of sufficient viscosity such that when it is administered it does not immediately dissipate, as water would, but instead takes the form of the site where it is administered. Some or all of the carrier and agent may dissipate from the scaffold over time. In one embodiment, the scaffold material is sufficiently viscous that when administered the injectable scaffold material remain substantially where it is injected, and does not immediately dissipate. In one embodiment, the scaffold forms, or is arranged to form, before there has been any substantial dissipation of the scaffold material. More than about 50%, 60% 70%, 80% or 90% by weight of the scaffold material provided, such as injected, into a particular site may remain at the site and form a scaffold at that site.

The plurality of hollow polymer pellets may be capable of interlinking and setting into a solid scaffold by sintering. The scaffold material may be capable of spontaneously solidifying when injected into the body due to an increase in temperature post administration (e.g. increase in the temperature from room temperature to body temperature). This increase in temperature may cause the scaffold material to interact to form a scaffold.

When the scaffold material solidifies to form a scaffold it may change from a suspension or a deformable viscous state to a solid state in which the scaffold formed is self-supporting and retains its shape. The solid scaffold formed may be brittle or more flexible depending on its intended application. The scaffold may be compressible without fracturing (for example a sponge consistency).

Solidification of the scaffold material (i.e. formation/setting of scaffold from the scaffold material) may be triggered by any appropriate means, for example, solidification may be triggered by a change in temperature, a change in pH, a change in mechanical force (compression), or the introduction of an interlinking, setting or gelling agent or catalyst.

In one embodiment, the solidification is triggered by plasticiser interaction with the hollow polymer pellets, such that they interlink to form the scaffold. In particular, the plasticiser may alter the surface chemistry of the hollow polymer pellets such that the surface Tg is decreased, thereby allowing the hollow polymer pellets to stick/interlink together.

In other words, the hollow polymer pellets may be discrete pellets that can be set/solidified into a scaffold by a change in temperature, a change in pH, a change in mechanical force (compression), or the introduction of an interlinking agent, setting agent or gelling agent or catalyst.

The scaffold material may be cross linked by a variety of methods including, for example, physical entanglement of polymer chains, UV cross linking of acrylate polymers, Michael addition reaction of thiolate or acrylate polymers, thiolate polymers cross linked via vinyl sulphones, cross linking via succinimates of vinyl sulphones, cross linking via hydrazines, thermally induced gelation, enzymatic cross-linking (for example, the addition of thrombin to fibrinogen), cross linking via the addition of salts or ions (especially Ca' ions), cross linking via isocyanates (for example, hexamethylene diisocyanate).

The scaffold material comprises discrete hollow polymer pellets, which are capable of interacting to form a scaffold. The interaction may cause the particles to inter-link, wherein the particles become physically connected and are held together. Inter-linking may be achieved by covalent, non-covalent, electrostatic, ionic, adhesive, cohesive or entanglement interactions between the hollow polymer pellets or components of the hollow polymer pellets.

A characteristic for the hollow polymer pellets, to ensure a scaffold can be formed, may be the glass transition temperature (Tg). By selecting hollow polymer pellets that have a Tg above room temperature (e.g. about 24° C.), at room temperature the hollow polymer pellets are below their Tg and behave as discrete pellets, but when exposed to a higher temperature (e.g. in the body) the hollow polymer pellets soften and interact/stick to their neighbours. In one embodiment, hollow polymer pellets are used that have a Tg from about 25° C. to 50° C., such as from about 27° C. to 50° C., e.g. from about 30° C. to 45° C., such as from 35° C. to 40° C., for example from about 37° C. to 40° C.

As the skilled man would appreciate, glass transition temperatures can be measured by differential scanning calorimetry (DSC) or rheology testing. In particular, glass transition temperature may be determined with DSC at a scan rate of 10° C./min in the first heating scan, wherein the glass transition is considered the mid-point of the change in enthalpy. A suitable instrument is a Perkin Elmer (Bucks, United Kingdom) DSC-7.

In other words, the formation of the scaffold is caused by exposing the hollow polymer pellets to a change in temperature, from a temperature that is below their Tg to a higher temperature. The higher temperature does not necessarily have to be equal to or above their Tg; any increase in temperature that is towards their Tg can trigger the required interaction between the hollow polymer pellets. In one embodiment, the formation of the scaffold is caused by exposing the hollow polymer pellets to a change in temperature, from a temperature that is below their Tg to a higher temperature, wherein the higher temperature is not more than 50° C. below their Tg, such as not more than 30° C. below their Tg or not more than 20° C. below their Tg or not more than 10° C. below their Tg.

In one embodiment, if the hollow polymer pellets are raised close to or above their Tg temperature on injection into the body, the hollow polymer pellets will inter-link to one or more other hollow polymer pellets to form a scaffold. By inter-link it is meant that adjacent hollow polymer pellets become joined together. For example, the hollow polymer pellets may inter-link due to entanglement of the polymer chains at the surface of one hollow polymer pellet with polymer chains at the surface of another hollow polymer pellet. There may be adhesion, cohesion or fusion between adjacent hollow polymer pellets.

When the hollow polymer pellets come together and inter-link, pores are formed in the resultant scaffold, as a consequence of the inevitable spaces between adjacent hollow polymer pellets. Such spaces/gaps between the hollow polymer pellets may not be filled with a hydrogel or other structural material. However, such spaces/gaps between the hollow polymer pellets may be filled with liquid carrier.

In one embodiment the scaffold material comprises discrete hollow polymer pellets which are capable of interacting to form a scaffold which have a Tg between about 35° C. and about 40° C., as well as other discrete hollow polymer pellets that have a Tg about 40° C. An agent for delivery may be incorporated into just one of the pellet types or both. Preferably the agent for delivery is incorporated in at least the discrete pellets that have a Tg above 40° C.

The scaffold may form without the generation of heat or loss of an organic solvent.

Formation of the scaffold from the scaffold material, once administered to a human or non-human animal, may take from about 20 seconds to about 24 hours, alternatively between about 1 minute and about 5 hours, alternatively between about 1 minute and about 1 hour, alternatively less than about 30 minutes, alternatively less than about 20 minutes. In one embodiment, the solidification occurs in between about 1 minute and about 20 minutes from administration.

The scaffold material may comprise from about 20% to about 80% hollow polymer pellets and from about 20% to about 80% carrier; from about 30% to about 70% hollow polymer pellets and from about 30% to about 70% carrier; e.g. the scaffold material may comprise from about 40% to about 60% hollow polymer pellets and from about 40% to about 60% carrier; the scaffold material may comprise about 50% hollow polymer pellets and about 50% carrier. The aforementioned percentages all refer to percentage by weight.

In one embodiment, the scaffold material can be used to form a scaffold that can resist a compressive load in excess of 0.5 MPa. In another embodiment, the scaffold material can be used to form a scaffold that can resist a compressive load in excess of 0.8 MPa. In another embodiment, the scaffold material can be used to form a scaffold that can resist a compressive load in excess of 0.9 MPa. In another embodiment, the scaffold material can be used to form a scaffold that can resist a compressive load in excess of 1 MPa. In another embodiment, the scaffold material can be used to form a scaffold that can resist a compressive load in excess of 1.5 MPa. In another embodiment, the scaffold material can be used to form a scaffold that can resist a compressive load in excess of 2 MPa. The scaffold compressive strength may be a property of the scaffold in situ, for example in the body. Additionally, the scaffold compressive strength may be a property of the scaffold measured in vitro following setting for at least 24 hours in a moist environment (for example 100% humidity) at about 37° C. In another embodiment, the scaffold may have a compressive strength of at least 0.5 MPa after setting for 2 h in a moist environment (for example 100% humidity) at about 37° C.

Other aspects and embodiments of the invention may not require a significant compressive strength, such as 1 MPa. For example, in an application where a thin layer of scaffold is desired (e.g. 2-10 mm thick layer), the level of the compressive strength of the scaffold may not be a relevant parameter. For example, in some applications a degree of flexibility of the scaffold may be desirable. Therefore, the present invention also encompasses substantially flexible scaffold material. Such flexible scaffold material may be pliable, such that it does not crack, splinter or break when bent or folded. In one embodiment, the scaffold has a putty consistency. In one embodiment, the scaffold may maintain its flexibility following setting of the scaffold. Alternatively, the scaffold may be hard (for example not compressible or malleable by an average adult hand). In an embodiment wherein a film of scaffold is formed, the scaffold may be sufficiently flexible in order to roll it into a tube without fracturing.

In one embodiment, the scaffold is formed ex situ (e.g. outside of the body/defect to be treated). In one embodiment, the scaffold material may be spread into a layer, i.e. a substantially thin layer prior to setting. The layer may be about 2-10 mm thick. The layer may be formed by spreading the scaffold material onto a surface prior to setting, for example by sintering. Spreading may comprise painting, rolling or injecting the scaffold material onto a surface to form a layer of scaffold material. The forming of a layer of scaffold may provide a flexible membrane of scaffold. In one embodiment, the layer of scaffold may be 10 mm or less in thickness. In another embodiment, the layer of scaffold may be 8 mm or less in thickness. In another embodiment, the layer of scaffold may be 6 mm or less in thickness. In another embodiment, the layer of scaffold may be 5 mm or less in thickness. In another embodiment, the layer of scaffold may be between 2 mm and 10 mm in thickness.

Additionally or alternatively, in methods wherein the scaffold material is spread into a layer, the scaffold material may comprise a carrier to hollow polymer pellet ratio of 1.2:1 or more. Additionally or alternatively, in methods wherein the scaffold material is spread into a layer, the scaffold material may comprise a carrier to hollow polymer pellet ratio of 1.5:1 or more. Additionally or alternatively, in methods wherein the scaffold material is spread into a layer, the scaffold material may comprise a carrier to hollow polymer pellet ratio of about 2:1. Additionally or alternatively, in methods wherein the scaffold material is spread into a layer, the scaffold material may comprise a carrier to hollow polymer pellet ratio of between about 1.2:1 and about 2:1.

According to another aspect of the present invention, there is provided a solid scaffold for tissue repair or replacement comprising a plurality of hollow polymer pellets, the hollow polymer pellets comprising a polymer pellet having an open hollow extending through the polymer pellet, wherein the hollow polymer pellets are inter-linked with each other.

In one embodiment, the hollow polymer pellets may be non-uniformly orientated relative to each other. For example, the hollow polymer pellets may be randomly orientated. The hollow polymer pellets may not be aligned relative to each other, for example in stacks to form honeycomb-like structures.

The scaffold may be formed of the scaffold material of the invention as herein described.

Method of Forming a Scaffold

According to another aspect of the present invention, there is provided a method of forming a scaffold for tissue repair or replacement, the method comprising:
  providing scaffold material comprising hollow polymer pellets, each pellet comprising an open hollow extending through the pellet; and
  setting the scaffold material such that it sets into a solid scaffold of hollow polymer pellets.

In one embodiment, the method of forming a scaffold material for tissue repair or replacement may comprise mixing the hollow polymer pellets with a liquid carrier prior to setting.

According to a first aspect of the present invention, there is provided a method of forming a scaffold material for controlled release of an agent in situ, the method comprising:

providing hollow polymer pellets;
providing an agent, wherein the agent is in a powder form;
mixing the hollow polymer pellets with the powder agent;
suspending the mixture in a liquid carrier to form a scaffold material that is a hollow polymer pellet suspension; and optionally
setting the scaffold material such that it sets into a solid scaffold of hollow polymer pellets, wherein the powder agent is encapsulated amongst the scaffold of hollow polymer pellets.

According to another aspect of the present invention, there is provided a method of forming a scaffold for controlled release of an agent in situ, the method comprising:
providing hollow polymer pellets;
providing an agent, wherein the agent is in a powder form;
mixing the hollow polymer pellets with the agent;
suspending the mixture in a liquid carrier to form a scaffold material that is a hollow polymer pellet suspension; and
setting the scaffold material such that it sets into a solid scaffold of hollow polymer pellets, wherein the powder agent is encapsulated amongst the scaffold of hollow polymer pellets.

Advantageously, the provision of the agent in a powder form still allows scaffold formation, yet also allows a favourable release profile of the agent in situ. For example, the agent can become available as the powder form of the agent (such as crystals) is solubilised in the carrier and/or body fluid of the patient being treated. Therefore, a burst release of agent can be provided following implantation/injection of the scaffold, followed by a longer sustained release (i.e. a $1^{st}$ order kinetics release profile).

Methods of forming the scaffold according to aspects of the invention herein may comprise the step of setting the scaffold by administrating/applying the scaffold material to a site for tissue repair or replacement. The site for a tissue repair or replacement may be a tissue in situ, in a body of a patient, or in a tissue in vitro/ex situ. The application may by methods described herein, such as implantation, injection, or moulding into the site for repair or replacement.

The Carrier

In one embodiment, the scaffold material may comprise a carrier. In one embodiment, the carrier is an aqueous carrier, such as water. The carrier may be an aqueous solution or suspension, such as saline, plasma, bone marrow aspirate, buffers, such as Hank's Buffered Salt Solution (HBSS), HEPES (4-(2-hydroxyethyl)-1-piperazineethanesulfonic acid), Ringers buffer, Krebs buffer, Dulbecco's PBS, or normal PBS; simulated body fluids, plasma platelet concentrate or tissue culture medium.

The carrier may, optionally, comprise one or more suspending agent. The suspending agent may be selected from carboxy methylcellulose (CMC), mannitol, polysorbate, poly propylene glycol, poly ethylene glycol, gelatine, albumin, alginate, hydroxyl propyl methyl cellulose (HPMC), hydroxyl ethyl methyl cellulose (HEMC), bentonite, tragacanth, dextrin, sesame oil, almond oil, sucrose, acacia gum and xanthan gum and combinations thereof. In one embodiment, the carrier comprises CMC.

The CMC may be provided in the carrier in an amount of 0.1% to 4% w/v. The CMC may be provided in the carrier in an amount of 0.1% to 3.5% w/v. The CMC may be provided in the carrier in an amount of 0.1% to 3% w/v. The CMC may be provided in the carrier in an amount of 0.1% to 2.5% w/v. The CMC may be provided in the carrier in an amount of 0.5% to 1% w/v.

The carrier may further comprise a polymer for enhancing the fluidity of the scaffold material. For example, the polymer may comprise poloxamer (Pluronic), such as poloxamer 407 (Pluronic F127). The polymer, such as poloxamer 407 (Pluronic F127), for enhancing the fluidity of the scaffold material may be provided in the carrier in an amount of about 1% w/v. The polymer, such as poloxamer 407 (Pluronic F127), for enhancing the fluidity of the scaffold material may be provided in the carrier in an amount of about 0.5 to 2% w/v.

The carrier may comprise one or more plasticiser. The plasticiser may be directly added to the carrier itself, for example, the plasticiser may not be provided in the carrier solely by diffusion from the hollow polymer pellets. In one embodiment, both the carrier and the hollow polymer pellets may comprise a plasticiser, such as PEG. In another embodiment, only the carrier and not the hollow polymer pellets may comprise a plasticiser, such as PEG. In another embodiment, only the hollow polymer pellets and not the carrier may comprise a plasticiser, such as PEG.

The plasticiser in the carrier may be selected from polyethylene glycol (PEG), polypropylene glycol, poly (lactic acid) or poly (glycolic acid) or a copolymer thereof, polycaprolactone, and low molecule weight oligomers of these polymers, or conventional plasticisers, such as, adipates, phosphates, phthalates, sabacates, azelates and citrates. The plasticiser may also be an alcohol such as ethanol or methanol. In one embodiment, the carrier may comprise ethanol. In one embodiment the plasticiser in the carrier does not comprise PEG. In another embodiment the plasticiser in the carrier comprises PEG.

In one embodiment, the plasticiser in the carrier may be selected from any one of TEC (triethyl citrate), ethanol, benzoic acid, and triacetin; or combinations thereof. In one embodiment, the plasticiser in the carrier may comprise or consist of TEC (triethyl citrate). In one embodiment, the plasticiser in the carrier may comprise or consist of triacetin.

In one embodiment, the carrier comprises a first plasticiser selected from any one of TEC (triethyl citrate), ethanol, benzoic acid, and triacetin; or combinations thereof; and a second plasticiser selected from any one of TEC (triethyl citrate), ethanol, benzoic acid, and triacetin; or combinations thereof, wherein the first and second plasticisers are different.

Advantageously, providing the plasticiser in the carrier selected from any one of TEC (triethyl citrate), ethanol, benzoic acid, and triacetin; or combinations thereof, and particularly two of such plasticisers, allows the hollow polymer pellets to be provided substantially plasticiser free, such as PEG free. As discussed above, this allows setting of the scaffold material into a solid scaffold in the absence of a plasticiser, such as PEG, in the hollow polymer pellets. Therefore, the hollow polymer pellets are easier and more economical to manufacture, and they can be stored at room temperature.

A first plasticizer may be provided in the carrier, wherein the first plasticiser is triethyl citrate, and second plasticiser may be provided in the carrier, wherein the second carrier comprises ethanol.

In an embodiment comprising two plasticisers, the first plasticiser may be provided in the carrier and the second plasticiser may be provided in the carrier and/or the hollow polymer pellets. In one embodiment comprising two plasticisers, the first plasticiser may be provided in the carrier and the second plasticiser may be PEG provided in the carrier and/or the hollow polymer pellets. In one embodiment comprising two plasticisers, the first plasticiser may be provided in the carrier and the second plasticiser may be PEG provided in the hollow polymer pellets.

In an embodiment comprising two plasticisers, the first plasticiser may be selected from any one of TEC (triethyl citrate), ethanol, benzoic acid, and triacetin; and the second plasticiser may be selected from any one of TEC (triethyl citrate), ethanol, benzoic acid, and triacetin, wherein the first and second plasticisers are different.

The carrier may also include other known pharmaceutical excipients in order to improve the stability of the agent.

The carrier may comprise between 0.5% and 40% w/v plasticiser. Alternatively, the carrier may comprise between 0.5% and 30% w/v plasticiser. In another embodiment, the carrier may comprise between 0.5% and 20% w/v plasticiser. Alternatively, the carrier may comprise between 0.5% and 15% w/v plasticiser. The carrier may comprise between 0.5% and 10% w/v plasticiser. Alternatively, the carrier may comprise between 0.5% and 8% w/v plasticiser. Alternatively, the carrier may comprise between 0.5% and 6% w/v plasticiser. Alternatively, the carrier may comprise between 0.5% and 5% w/v plasticiser. Alternatively, the carrier may comprise between 1% and 6% w/v plasticiser. Alternatively, the carrier may comprise between 2% and 6% w/v plasticiser. Alternatively, the carrier may comprise about 0.5%, 0.79%, 1%, 2%, 3%, 4%, 5% or 6% w/v plasticiser. In an embodiment wherein the plasticiser is TEC or TA, the TEC or TA may be provided in the carrier in an amount of between 0.5% and 10% w/v. Alternatively, in an embodiment wherein the plasticiser is TEC or TA, the TEC or TA may be provided in the carrier in an amount of between 0.5% and 8% w/v. Alternatively, in an embodiment wherein the plasticiser is TEC or TA, the TEC or TA may be provided in the carrier in an amount of between 0.5% and 6% w/v. Alternatively, in an embodiment wherein the plasticiser is TEC or TA, the TEC or TA may be provided in the carrier in an amount of between 0.5% and 5% w/v. Alternatively, in an embodiment wherein the plasticiser is TEC or TA, the TEC or TA may be provided in the carrier in an amount of between 1% and 6% w/v. Alternatively, in an embodiment wherein the plasticiser is TEC or TA, the TEC or TA may be provided in the carrier in an amount of between 2% and 6% w/v. Alternatively, in an embodiment wherein the plasticiser is TEC or TA, the carrier may comprise about 0.5%, 0.79%, 1%, 2%, 3%, 4%, 5% or 6% w/v TEC or TA.

In an embodiment wherein the plasticiser is benzoic acid, the benzoic acid may be provided in the carrier in an amount of between 0.1% and 3% w/v. In an embodiment wherein the plasticiser is ethanol, the ethanol may be provided in the carrier in an amount of between 0.1% and 20% w/v. In an embodiment wherein the plasticiser is NMP (N-Methyl-2-pyrrolidone), the NMP may be provided in the carrier in an amount of between 0.1% and 90% w/v, the NMP may be provided in an amount of between 1% and 90% w/v, or between 10% and 80% w/v, or in an amount of about 78% w/v. In an embodiment wherein the plasticiser is DMSO, the DMSO may be provided in the carrier in an amount of between 0.1% and 10% w/v. In an embodiment wherein the plasticiser is PEG, such as PEG400, the PEG may be provided in the carrier in an amount of between 0.1% and 30% w/v. In an embodiment wherein the plasticiser is glycerin, the glycerin may be provided in the carrier in an amount of between 0.1% and 25% w/v.

The carrier may comprise a plasticiser selected from Table 2 herein. The percentage of the plasticiser in the carrier may be according to the ranges provided herein or up to the highest amount for a pharmaceutical as provided in Table 2.

In one embodiment, one or more additional excipient or delivery enhancing agent may also be included in the scaffold material, such as in the carrier, e.g. surfactants and/or hydrogels, in order to further influence release rate.

The carrier may interact with the hollow polymer pellets. The carrier may interact with the hollow polymer pellets to prevent or slow the formation of a scaffold and to allow the hollow polymer pellets to be administered to a human or non-human animal before a scaffold forms. The carrier may prevent interaction between the hollow polymer pellets due to separation of the pellets by suspension in the carrier. It may be that the carrier completely prevents the formation of the scaffold prior to administration, or it may simply slow the formation, e.g. permitting the scaffold formation to begin but not complete formation prior to administration. In one embodiment the composition comprises sufficient carrier to prevent the formation of a scaffold even when the composition is at a temperature, which, in the absence of the carrier, would cause the hollow polymer pellets to form a scaffold. In one embodiment, the scaffold material comprises sufficient carrier to slow the formation of a scaffold such that when the scaffold material is at a temperature which, in the absence of the carrier, would cause the hollow polymer pellets to readily form a scaffold, a scaffold does not readily form, e.g. does not form over a timescale such as one hour to five hours.

The carrier may interact with the hollow polymer pellets and cause the surface of the hollow polymer pellets to swell, whilst remaining as discrete hollow polymer pellets, thus allowing administration by injection. However, once the composition has been administered and the carrier begins to dissipate the hollow polymer pellets may begin to de-swell. De-swelling may assist the joining together of hollow polymer pellets.

Interaction of the hollow polymer pellets with the carrier may cause the glass transition temperature of the hollow polymer pellets to change. For example, the interaction may cause the glass transition temperature to be lowered. Interaction of the hollow polymer pellets with the carrier may cause the glass transition temperature of the hollow polymer pellet's surface to change. For example, the interaction may cause the glass transition temperature of the surface of the hollow polymer pellets to be lowered.

The carrier may act as a lubricant to allow the hollow polymer pellets to be administered to a human or non-human animal, for example by injection. The carrier may provide lubrication when the scaffold material is dispensed from a syringe. The carrier may help to reduce or prevent shear damage to hollow polymer pellets dispensed from a syringe.

The ratio of carrier to hollow polymer pellets in the scaffold material may be at least 1:1. The ratio of carrier to hollow polymer pellets in the scaffold material may be at least 1.5:1. The ratio of carrier to hollow polymer pellets in the scaffold material may be at least 1.2:1. In one embodiment, the ratio of carrier to hollow polymer pellets in the scaffold material may be between 0.7:1 and 2:1.

The carrier may further comprise a buffer. For example plasticisers such as TEC and TA can be acidic and a buffer may be provided to reduce the acidity of such components. Any suitable buffer may be provided, for example PBS, Tris buffer, or sodium bicarbonate.

The Agent

With reference to a powder form of the agent or powdered agent, the powder may be dry powder. For example the dry powder may have substantially no water content. Alternatively the term dry may be a water activity of less than 0.5 Aw, or less than less than 0.3 Aw, or less than 0.1 Aw.

The powdered agent may be in crystalline, semi-crystalline or amorphous form. In one embodiment, the powdered agent may be in crystalline form.

In one embodiment, the powdered agent is encapsulated amongst the scaffold of hollow polymer pellets and additional agent may be encapsulated within the hollow polymer pellets. The additional agent may be in any form, for example a liquid form, such as a solution or suspension, a paste, a gel, or a powder form. The additional agent may be a different agent relative to the powder agent. Alternatively, the additional agent may be the same agent as the powder agent, but in a different form such as a solution or suspension, a gel, or a paste (i.e. the additional agent may not be in a powder form). Reference to the form of the agent, such as powder form, liquid, paste or gel form may refer to the condition of the agent at the point of addition to the mixture or blend (i.e. it is not intended to refer to the form of the agent following use, for example in situ after scaffold formation).

The additional agent may be provided in the hollow polymer pellets during the formation of the hollow polymer pellets, for example by adding to the polymer for extrusion into hollow polymer pellets.

In one embodiment, the agent is only provided as a powdered agent to be encapsulated amongst the scaffold of hollow polymer pellets. For example, no other agent, or form of agent, is provided, for example, in the hollow polymer pellets.

Other aspects and embodiments of the invention herein may be practised with the provision of an agent in the scaffold material for release of the agent, but the agent may not be required to be added in a powder form. Therefore, some aspects and embodiments of the invention may provide an agent in the scaffold material in a non-powder form. For example the agent may be solubilised in the carrier. Additionally or alternatively, the agent may be provided/encapsulated in the hollow polymer pellets. In another embodiment, the agent may be provided to the scaffold material as a separate liquid phase relative to the carrier.

The agent may be a therapeutically, prophylactically or diagnostically active substance. It may be any bioactive agent.

In another embodiment, the powdered agent may be a non-therapeutic agent, for example a protective agent or a second agent provided to augment or protect a first powdered agent that may be therapeutically, prophylactically or diagnostically active substance. In one embodiment a second powdered agent may be provided to enhance the stability of function of a first powdered agent. The powdered agent may comprise cyclodextrin.

In one embodiment the powdered agent may comprise carboxymethyl cellulose (CMC). The provision of powdered CMC may be provided to alter the scaffold setting properties.

The agent for delivery may be a drug, a cell, signalling molecule, such as a growth factor, or any other suitable agent. For example, the agent may comprise amino acids, peptides, proteins, sugars, antibodies, nucleic acid, antibiotics, antimycotics, growth factors, nutrients, enzymes, hormones, steroids, synthetic material, adhesion molecules, colourants/dyes (which may be used for identification), radioisotopes (which may be for X-ray detection and/or monitoring of degradation), and other suitable constituents, or combinations thereof.

Other agents which may be added include but are not limited to epidermal growth factor, platelet derived growth factor, basic fibroblast growth factor, vascular endothelial growth factor, insulin-like growth factor, nerve growth factor, hepatocyte growth factor, transforming growth factors and other bone morphogenic proteins, cytokines including interferons, interleukins, monocyte chemotactic protein-1 (MCP-1), oestrogen, testosterone, kinases, chemokinases, glucose or other sugars, amino acids, calcification factors, dopamine, amine-rich oligopeptides, such as heparin binding domains found in adhesion proteins such as fibronectin and laminin, other amines, tamoxifen, cis-platin, peptides and certain toxoids. Additionally, drugs (including statins and NSAIDs), hormones, enzymes, nutrients or other therapeutic agents or factors or mixtures thereof may be included.

The agent may comprise nucleic acid, such as DNA, RNA, or plasmid.

In some embodiments, the agent for delivery is a statin, e.g. simvastatin, atorvastatin, fluvastatin, pravastatin or rosuvastatin. The statin may be simvastatin. Embodiments in which the agent is a statin are particularly suitable for the treatment of orthopaedic indications, craniomaxillofacial surgery and dentistry.

In an embodiment wherein an agent is part of (i.e. encapsulated within) the hollow polymer pellets, the agent may be up to 50% of the content of the hollow polymer pellets. In another embodiment wherein an agent is part of (i.e. encapsulated within) the hollow polymer pellets, the agent may be up to 40% of the content of the hollow polymer pellets. In another embodiment wherein an agent is part of (i.e. encapsulated within) the hollow polymer pellets, the agent may be up to 30% of the content of the hollow polymer pellets. In another embodiment wherein an agent is part of (i.e. encapsulated within) the hollow polymer pellets, the agent may be up to 20% of the content of the hollow polymer pellets. In another embodiment wherein an agent is part of (i.e. encapsulated within) the hollow polymer pellets, the agent may be up to 10% of the content of the hollow polymer pellets. In another embodiment wherein an agent is part of (i.e. encapsulated within) the hollow polymer pellets, the agent may be between 10% and 50% of the content of the hollow polymer pellets. In another embodiment wherein an agent is part of (i.e. encapsulated within) the hollow polymer pellets, the agent may be between 1% and 50% of the content of the hollow polymer pellets. In another embodiment wherein an agent is part of (i.e. encapsulated within) the hollow polymer pellets, the agent may be between 0.1% and 50% of the content of the hollow polymer pellets. In another embodiment wherein an agent is part of (i.e. encapsulated within) the hollow polymer pellets, the agent may be between 0.5% and 50% of the content of the hollow polymer pellets. In another embodiment wherein an agent is part of (i.e. encapsulated within) the hollow polymer pellets, the agent may be between 0.1% and 1% of the content of the hollow polymer pellets. In another embodiment wherein an agent is part of (i.e. encapsulated within) the hollow polymer pellets, the agent may be between 0.5% and 10% of the content of the hollow polymer pellets. In another embodiment wherein an agent is part of (i.e. encapsulated within) the hollow polymer pellets, the agent may be between 0.1% and 20% of the content of the hollow polymer pellets. The percentage may be w/w.

In an embodiment wherein an agent is provided in the carrier, the agent may be up to 75% of the content of the carrier. In another embodiment wherein an agent is provided in the carrier, the agent may be up to 60% of the content of the carrier. In another embodiment wherein an agent is provided in the carrier, the agent may be up to 50% of the content of the carrier. In another embodiment wherein an agent is provided in the carrier, the agent may be up to 40% of the content of the carrier. In another embodiment wherein an agent is provided in the carrier, the agent may be up to 30% of the content of the carrier. In another embodiment wherein an agent is provided in the carrier, the agent may be up to 20% of the content of the carrier. In another embodiment wherein an agent is provided in the carrier, the agent may be up to 10% of the content of the carrier. In another embodiment wherein an agent is provided in the carrier, the agent may be between 10% and 75% of the content of the carrier, or between 20% and 50% of the content of the carrier. The percentage may be w/v.

In an embodiment wherein an agent is in a powder form and mixed with the hollow polymer pellets prior to setting, the agent may be up to 75% of the content of the scaffold material. In another embodiment wherein an agent is in a powder form and mixed with the hollow polymer pellets prior to setting, the agent may be up to 60% of the content of the scaffold material. In another embodiment wherein an agent is in a powder form and mixed with the hollow polymer pellets prior to setting, the agent may be up to 50% of the content of the scaffold material. In another embodiment wherein an agent is in a powder form and mixed with the hollow polymer pellets prior to setting, the agent may be up to 40% of the content of the scaffold material. In another embodiment wherein an agent is in a powder form and mixed with the hollow polymer pellets prior to setting, the agent may be up to 30% of the content of the scaffold material. In another embodiment wherein an agent is in a powder form and mixed with the hollow polymer pellets prior to setting, the agent may be up to 20% of the content of the scaffold material. In another embodiment wherein an agent is in a powder form and mixed with the hollow polymer pellets prior to setting, the agent may be between 10% and 75% of the content of the scaffold material, or between 20% and 50% of the content of the scaffold material, alternatively between 20% and 30% of the content of the scaffold material.

The agent release may be controlled, that is, not all of the agent may be released in one large dose. The scaffold produced may permit the kinetics of agent release from the carrier to be controlled. The rate of release may be controlled by controlling the size and/or number of the pores in the scaffold and/or the rate of degradation of the scaffold. Other factors that can be controlled are the concentration of any suspending agent included in the carrier, the viscosity or physiochemical properties of the composition, and the choice of carrier.

The agent may be released by one or more of: diffusion of the agent through the pores; degradation of the scaffold leading to increased porosity and improved outflow of fluid carrying the agent; and physical release of agent from the polymer microparticles. It is within the abilities of the skilled person to appreciate that the size and/or number of the pores in the scaffold and/or the rate of degradation of the scaffold can readily be selected by appropriate choice of starting material so as to achieve the desired rate of release.

Diffusion of the agent away from the scaffold can occurs due to diffusion driven by a concentration gradient and the natural flow of body fluids through and away from the scaffold.

The agent may be released in an amount effective to have a desired local or systemic physiological or pharmacologically effect.

The scaffold may allow for agent release to be sustained for some time, for example at least about 2 hours, at least about 4 hours, at least about 6 hours, at least about 10 hours, at least about 12 hours, or at least about 24 hours. In one embodiment, the sustained release may be over at least 48 hours. In another embodiment, the sustained release may be over at least a week. In another embodiment, the sustained release may be over at least a 10 days.

Delivery of an agent means that the agent may be released from the scaffold into the environment around the scaffold, for example surrounding tissues.

The formed scaffold may allow a substantially zero or first order release rate of the agent from the scaffold. A zero order release rate is a constant release of the agent over a defined time. A first order release rate may also be considered a "burst release".

In one embodiment, the initial day 1 burst release is less than about 25-33% of total loading (such as less than about 20% or more such as less than about 10%, alternatively, less than about 5%). This initial burst may then be followed by 1-2% release per day for about 14 days (which may equate to about 0.5-2 mcg/day). Release of drug may continue for at least 14 days. Release of drug may continue for at least 20 days, 30 days, 40 day or 50 days. In some embodiments, release continues for about 14 to 56 days. In some embodiments release continues for more than 56 days.

In other embodiments, release kinetics can be modified by the use of mixed molecular weight PLGA polymers, which can effectively increase either the initial or longer-term release and help to avoid any therapeutic lag phase (European Journal of Pharmaceutics and Biopharmaceutics Volume 50, Issue 2, September 2000, Pages 263-270).

In other embodiments other release modifiers may be used to adjust release kinetics. For example, adjustments to the viscosity of a carboxymethycellulose-containing liquid phase residing within the scaffold pores may be made.

It is possible to use any animal cell with the scaffold material of the invention. Examples of cells which may be used include bone, osteoprogenitor cells, cartilage, muscle, liver, kidney, skin, endothelial, gut, intestinal, cardiovascular, cardiomycotes, chondrocyte, pulmonary, placental, amnionic, chorionic, foetal or stem cells. Where stem cells are used, preferably non-embryonic stem cells are used. The cells may be included for delivery to the site of scaffold formation, or they may be included and intended to be retained in the scaffold, for example, to encourage colonisation of the scaffold.

In one embodiment, viable cells are provided in the scaffold material, for example, prior to formation/setting of the scaffold. For example, viable cells may be added to the scaffold material, or otherwise the hollow polymer pellets, prior to setting. In another embodiment, viable cells are provided in the scaffold material after formation/setting of the scaffold.

In one embodiment, the surface of the hollow polymer pellets may be treated prior to introducing cells in order to enhance cell attachment. Surface treatments may comprise coating techniques to coat the surfaces of the hollow polymer pellets with an agent capable of enhancing or facilitating cell attachment. Additionally or alternatively, surface treatments may comprise physical or chemical modifications to the surface of the hollow polymer pellets. In surface coating, the hollow polymer pellets can be coated with materials that change their biological interactions, by altering surface charge, hydrophilicity and/or receptor-binding moieties. Such examples include, but are not limited to, chemical plasmas, peptides or carbohydrates, extracellular matrix components such as fibronectin or vitronectin or fragments thereof, poly-L-ornithine, polylysine and/or polyallylamines. In one embodiment, in surface physical/chemical modification, the hollow polymer pellet surfaces can modified by treating them with alkaline solutions such as NaOH solutions. In one embodiment, in surface physical/chemical modification, the hollow polymer pellet surfaces can be made rougher by treating them with alcohols, acids or bases. In another embodiment, in surface physical/chemical modification, the hollow polymer pellet surfaces can be made more hydrophilic and rougher by treating them with hydro-alcoholic alkaline solutions.

Advantageously, the hollow/lumen of the hollow polymer pellets significantly increases the surface area for cell attachment. Therefore, a higher dose/density of cells is achievable per unit volume relative to non-hollow pellet scaffolds, or other scaffold types. Cells in the hollow are better protected from shear stress and other mechanical forces as the scaffold material is mixed, injected or implanted.

Therefore, according to another aspect of the present invention, there is provided a method of forming a scaffold comprising cells for tissue repair or replacement, the method comprising
  incubating hollow polymer pellet composition according to the invention herein in a bioreactor with cells;
  allowing the cells to attach to the hollow polymer pellets to form cell-loaded hollow polymer pellets; and
  harvesting the cell-loaded hollow polymer pellets; and
  optionally setting the cell-loaded hollow polymer pellets into a solid scaffold.

Setting the cell-loaded hollow polymer pellets into a solid scaffold may be in situ in a body or tissue. The cell-loaded hollow polymer pellets may be injected or implanted into a tissue or body for treatment prior to setting the cell-loaded hollow polymer pellets into a solid scaffold.

In one embodiment, the setting of the scaffold material to form the scaffold is in situ. For example, the setting may take place post-administration, for example within a bone defect. Alternatively, setting may be provided ex situ, for example to provide a scaffold outside of the body. In one embodiment, the setting of the scaffold material to form the scaffold is at about 37° C. In one embodiment, the setting of the scaffold material to form the scaffold is at about 35° C. or less. The setting of the scaffold material to form the scaffold may be in a humid environment, for example 100% humidity, alternatively at least 90% humidity. The setting of the scaffold material to form the scaffold may be whilst submerged in a solution.

Other Aspects

According to another aspect of the present invention, there is provided a method of forming a scaffold material, the method comprising:
  providing hollow polymer pellets;
  suspending the hollow polymer pellets in a liquid carrier to form a scaffold material, which is a hollow polymer pellet suspension, wherein the liquid carrier comprises a plasticiser; and
  optionally setting the hollow polymer pellet suspension such that it sets into a solid scaffold of hollow polymer pellets.

Advantageously the methods of the invention herein allow the skilled person to select appropriate scaffold properties or setting properties, for example when a plasticiser, such us TEC, is used in the liquid carrier it is possible to sinter hollow polymer pellets made by PLGA/ceramic blends within 15 minutes to form a scaffold. Further advantageously, very low concentrations of plasticiser may be used according to the methods of the invention. By choosing the concentration of plasticiser, such as TEC, it is possible to control the setting properties of the scaffold material.

In one embodiment, the concentration of TEC or TA in the carrier may be 0.79% to 6% w/v. In one embodiment, the concentration of TEC or TA in the carrier may be about 0.79% w/v. In one embodiment, the concentration of TEC or TA in the carrier may be 1% or less than 1% w/v. In one embodiment, the concentration of TEC or TA in the carrier may be less than 6% w/v. In one embodiment, the concentration of TEC or TA in the carrier may be less than 5% w/v. In one embodiment, the concentration of TEC or TA in the carrier may be between 2 and 5% w/v. In one embodiment, the concentration of TEC or TA in the carrier may be about 2.5% or 3% w/v. In one embodiment, the concentration of TEC or TA in the carrier may be about 4% or 5% w/v.

In one embodiment, the concentration of benzoic acid in the carrier may be 0.79% to 6% w/v. In one embodiment, the concentration of benzoic acid in the carrier may be about 0.79% w/v. In one embodiment, the concentration of benzoic acid in the carrier may be 1% or less than 1% w/v. In one embodiment, the concentration of benzoic acid in the carrier may be less than 6% w/v. In one embodiment, the concentration of benzoic acid in the carrier may be less than 5% w/v. In one embodiment, the concentration of benzoic acid in the carrier may be between 2 and 5% w/v. In one embodiment, the concentration of benzoic acid in the carrier may be about 2.5% or 3% w/v. In one embodiment, the concentration of benzoic acid in the carrier may be about 4% or 5% w/v.

In one embodiment, the plasticiser in the carrier may be a first plasticiser and a second plasticiser is provided in the carrier and/or hollow polymer pellets, wherein the first and second plasticisers are different. The second carrier may be selected from any one of PEG, TEC (triethyl citrate), ethanol, benzoic acid, and triacetin, wherein the first and second plasticisers are different In one embodiment, the hollow polymer pellets may not comprise PEG. The hollow polymer pellets may be substantially PEG free. In one embodiment, the hollow polymer pellets may comprise less than 0.5% PEG w/w, or less than 0.2% w/w PEG, or less than 0.1% w/w PEG.

In one embodiment, the hollow polymer pellets may comprise 42-48% PLGA95:5, 2-8% PEG400 and 44-56% ceramic (to a total of 100% of components). In another embodiment, the hollow polymer pellets may comprise 46.25% PLGA95:5, 3.75% PEG400 and 50% ceramic.

According to another aspect of the invention, there is provided a method of forming a scaffold material, the method comprising:
  providing hollow polymer pellets;
  suspending the hollow polymer pellets in a liquid carrier to form a scaffold material, which is a hollow polymer pellet suspension, wherein the scaffold material comprises a first plasticiser in the hollow polymer pellets and/or the liquid carrier, and a second plasticiser in the liquid carrier,
  wherein the first plasticiser is selected from any one of TEC (triethyl citrate), ethanol, benzoic acid, triacetin, NMP, DMSO and PEG; and the second plasticiser is selected from any one of PEG, DMSO, NMP, TEC (triethyl citrate), ethanol, benzoic acid, and triacetin (TA), wherein the first and second plasticisers are different; and
  optionally setting the hollow polymer pellet suspension such that it sets into a solid scaffold of hollow polymer pellets.

In one embodiment, the first plasticizer is triethyl citrate, and the second plasticiser is ethanol. In another embodiment, the first plasticizer is triacetin, and the second plasticiser is ethanol. In one embodiment, the first plasticizer is triethyl citrate or triacetin, and the second plasticiser is PEG in the hollow polymer pellets.

In one embodiment, the first plasticiser comprises TEC (triethyl citrate) and the second plasticiser is selected from any one of PEG, DMSO, NMP, ethanol, benzoic acid, and triacetin (TA). In another embodiment, the first plasticiser comprises ethanol and the second plasticiser is selected from any one of PEG, DMSO, NMP, TEC (triethyl citrate), benzoic acid, and triacetin (TA). In another embodiment, the first plasticiser comprises benzoic acid and the second plasticiser is selected from any one of PEG, DMSO, NMP, TEC (triethyl citrate), ethanol, and triacetin (TA). In another embodiment, the first plasticiser comprises triacetin and the second plasticiser is selected from any one of PEG, DMSO, NMP, TEC (triethyl citrate), ethanol, and benzoic acid. In another embodiment, the first plasticiser comprises NMP and the second plasticiser is selected from any one of PEG, DMSO, TEC (triethyl citrate), ethanol, benzoic acid, and triacetin (TA). In another embodiment, the first plasticiser comprises DMSO and the second plasticiser is selected from any one of PEG, NMP, TEC (triethyl citrate), ethanol, benzoic acid, and triacetin (TA). In another embodiment, the first plasticiser comprises PEG and the second plasticiser is selected from any one of DMSO, NMP, TEC (triethyl citrate), ethanol, benzoic acid, and triacetin (TA).

In one embodiment, the second plasticiser comprises TEC (triethyl citrate) and the first plasticiser is selected from any one of PEG, DMSO, NMP, ethanol, benzoic acid, and triacetin (TA). In another embodiment, the second plasticiser comprises ethanol and the first plasticiser is selected from any one of PEG, DMSO, NMP, TEC (triethyl citrate), benzoic acid, and triacetin (TA). In another embodiment, the second plasticiser comprises benzoic acid and the first plasticiser is selected from any one of PEG, DMSO, NMP, TEC (triethyl citrate), ethanol, and triacetin (TA). In another embodiment, the second plasticiser comprises triacetin and the first plasticiser is selected from any one of PEG, DMSO, NMP, TEC (triethyl citrate), ethanol, and benzoic acid. In another embodiment, the second plasticiser comprises NMP and the first plasticiser is selected from any one of PEG, DMSO, TEC (triethyl citrate), ethanol, benzoic acid, and triacetin (TA). In another embodiment, the second plasticiser comprises DMSO and the first plasticiser is selected from any one of PEG, NMP, TEC (triethyl citrate), ethanol, benzoic acid, and triacetin (TA). In another embodiment, the second plasticiser comprises PEG and the first plasticiser is selected from any one of DMSO, NMP, TEC (triethyl citrate), ethanol, benzoic acid, and triacetin (TA).

In an embodiment wherein a first and second plasticiser is provided, the hollow polymer pellets may not comprise PEG. In an embodiment wherein a first and second plasticiser is provided, the hollow polymer pellets may be substantially PEG free. In another embodiment wherein a first and second plasticiser is provided, the hollow polymer pellets may comprise less than 0.5% w/w PEG, or less than 0.2% w/w PEG, or less than 0.1% w/w PEG.

Providing the two or more plasticisers according to the invention allows greater setting control of the scaffold material into a solid scaffold. For example the ratio of carrier to hollow polymer pellets in the scaffold material may be increased without also inadvertently prolonging the scaffold setting time. Therefore, the present invention allows high carrier to hollow polymer pellet ratio. In one embodiment, the carrier to hollow polymer pellet ratio is at least 0.7:1 v/w. In another embodiment, the carrier to hollow polymer pellet ratio is at least 1:1 v/w. In another embodiment, the carrier to hollow polymer pellet ratio is at least 1.2:1 v/w. In another embodiment, the carrier to hollow polymer pellet ratio is at least 1.5:1 v/w. In another embodiment, the carrier to hollow polymer pellet ratio is at least 1.8:1 v/w. In another embodiment, the carrier to hollow polymer pellet ratio is at least 2:1 v/w. In another embodiment, the carrier to hollow polymer pellet ratio is between about 1.2:1 v/w and about 2:1 v/w.

Advantageously, the high carrier to hollow polymer pellet ratio of the invention can allow lower viscosity scaffold material to be provided without prolonging the setting times. The higher carrier to hollow polymer pellet ratio achievable in the present invention allows the scaffold material to be more fluidic or malleable prior to setting. Advantageously, the scaffold material can be easier to inject prior to setting due to a lower viscosity of the scaffold material. Furthermore, the scaffold material may be more formable to a shape, such as a bone defect to be repaired. A higher carrier to hollow polymer pellet ratio also aids the forming of thin layers or membranes of the scaffold material for applications where a thin membrane/layer scaffold is required. Therefore, the low viscosity scaffold material may be spread into a layer prior to setting into a scaffold. A thin layer may comprise 2-10 mm.

According to another aspect of the present invention, there is provided a method of forming a scaffold material comprising hollow polymer pellets, the method comprising:
  extruding a polymer through an extruder, wherein the extruder comprises a die to form a hollow in the polymer extrudate;
  cutting the polymer extrudate into pellets to form hollow polymer pellets.

The method of forming a scaffold material may further comprise suspending the hollow polymer pellets in a liquid carrier to form a hollow polymer pellet suspension. The method of forming a scaffold material may further comprise forming a scaffold by setting the hollow polymer pellets, or suspension thereof, such that it sets into a solid scaffold of hollow polymer pellets.

Cutting may be carried out by a pelletiser, such as a strand pelletiser.

In one embodiment, extruding the polymer may be at a temperature at or around its Tm or higher. In an embodiment comprising PLGA in the hollow polymer pellet material, the process may be performed at between about 70 and 120° C. In an alternative embodiment where a thinner/more flexible hollow polymer pellet is desired, the extrusion may be at a temperature of between 100 and 120° C.

Extruding the polymer may be at a screw speed of between about 1 and 10 rpm. In an embodiment where a thinner/more flexible hollow polymer pellet is desired, the extrusion may be at a screw speed of between about 8 and 10 rpm.

In an embodiment comprising PLGA in the hollow polymer pellet material, the process may be performed at between about 70 and 120° C. at a screw speed of between about 1 and 10 rpm. In an embodiment comprising PLGA in the hollow polymer pellet material, the process may be performed at between about 70 and 120° C. at a screw speed of between about 8 and 10 rpm. In an alternative embodiment where a thinner/more flexible hollow polymer pellet is desired, the extrusion may be at a temperature of between 100 and 120° C. at a screw speed of between about 8 and 10 rpm. In an alternative embodiment where a thinner/more flexible hollow polymer pellet is desired, the extrusion may be at a temperature of between 100 and 120° C. at a screw speed of between about 1 and 10 rpm.

In another embodiment, extruding the polymer may be at a pelletiser winder speed of between 10 and 40 m/min. In an embodiment where a thinner/more flexible hollow polymer pellet is desired, the extrusion may be at a winder speed of between 30 and 40 rpm.

In another embodiment, extruding the polymer may be at a pelletiser winder speed of between 10 and 40 m/min at a temperature of between 100 and 120° C. In another embodiment, extruding the polymer may be at a pelletiser winder speed of between 10 and 40 m/min at a temperature of between 70 and 120° C. In an embodiment where a thinner/more flexible hollow polymer pellet is desired, the extrusion may be at a winder speed of between 30 and 40 rpm at a temperature of between 100 and 120° C. In another embodiment where a thinner/more flexible hollow polymer pellet is desired, the extrusion may be at a winder speed of between 30 and 40 rpm at a temperature of between 70 and 120° C.

According to another aspect of the present invention, there is provided a method of forming a scaffold material comprising a natural-polymer or non-polymer particle content, the method comprising:

blending a polymer with natural-polymer or non-polymer particles;

forming hollow polymer pellets from the blend, wherein the hollow polymer pellets have the natural-polymer or non-polymer particles encapsulated therein; and optionally suspending the hollow polymer pellets in a liquid carrier to form a hollow polymer pellet suspension; and further optionally setting the hollow polymer pellet suspension such that it sets into a solid scaffold of hollow polymer pellets.

Encapsulation of the natural-polymer or non-polymer particles in the polymer of the hollow polymer pellets is understood to include the polymer being dispersed amongst and surrounding the natural-polymer or non-polymer particles (e.g. not just a polymer surface coating on the natural-polymer or non-polymer particles). For example, the hollow polymer pellets may comprise natural-polymer or non-polymer particles entirely encased within the polymer and/or natural-polymer or non-polymer particles exposed at the surface of the hollow polymer pellets. For example, the hollow polymer pellets may be discreet particles having a plurality of natural-polymer particles or non-polymer particles encapsulated therein.

In one embodiment non-polymer particles, such as ceramic particles, are provided.

In one embodiment, blending the polymer with natural-polymer or non-polymer particles may comprise the step of dry mixing the polymer with natural-polymer or non-polymer particles. The dry mixture of the polymer and natural-polymer or non-polymer particles may be hot-melt extruded and the extrudate may be pelleted to form hollow polymer pellets having natural-polymer or non-polymer particles encapsulated therein. In another embodiment, the dry mixture of the polymer and natural-polymer or non-polymer particles may be hot-melt extruded and the extrudate may be pelleted. The dry mixture of the polymer and natural-polymer or non-polymer particles may be hot-melt extruded in a twin screw extruder for sufficient mixing. The pelleted extrudate then may be further extruded in a single screw extruder with a dye to form hollow polymer pellets having natural-polymer or non-polymer particles encapsulated therein.

The dry mixture of the polymer and natural-polymer particles may be blended together by physically mixing them.

The scaffold material may comprise between 1% and 55% natural-polymer or non-polymer particles, such as ceramic. In another embodiment, the scaffold material may comprise between 1% and 50% natural-polymer or non-polymer particles, such as ceramic. In another embodiment, the scaffold material may comprise between 1% and 55% natural-polymer or non-polymer particles, such as ceramic. In another embodiment, the scaffold material may comprise between 10% and 50% natural-polymer or non-polymer particles, such as ceramic. In another embodiment, the scaffold material may comprise between 20% and 50% natural-polymer or non-polymer particles, such as ceramic. In another embodiment, the scaffold material may comprise between 30% and 50% natural-polymer or non-polymer particles, such as ceramic. In another embodiment, the scaffold material may comprise between 40% and 50% natural-polymer or non-polymer particles, such as ceramic. The percentage may be w/w.

In one embodiment, the hollow polymer pellets may comprise between 1% and 55% (w/w) of natural-polymer or non-polymer particles, such as ceramic. Alternatively, the hollow polymer pellets may comprise between 20% and 55% (w/w) of natural-polymer or non-polymer particles, such as ceramic. Alternatively, the hollow polymer pellets may comprise between 20% and 50% (w/w) of natural-polymer or non-polymer particles, such as ceramic. Alternatively, the hollow polymer pellets may comprise between 30% and 50% (w/w) of natural-polymer or non-polymer particles, such as ceramic. Alternatively, the hollow polymer pellets may comprise between 40% and 50% (w/w) of natural-polymer or non-polymer particles, such as ceramic.

The scaffold material comprising natural-polymer or non-polymer particles, such as ceramic, may comprise less than 40% w/v plasticiser in the carrier. In another embodiment, the scaffold material comprising natural-polymer or non-polymer particles, such as ceramic, may comprise less than 38% w/v plasticiser in the carrier. In another embodiment, the scaffold material comprising natural-polymer or non-polymer particles, such as ceramic, may comprise less than 35% w/v plasticiser in the carrier. In another embodiment, the scaffold material comprising natural-polymer or non-polymer particles, such as ceramic, may comprise less than 30% w/v plasticiser in the carrier. Alternatively, the plasticiser content may be less than 20%, 15%, 10% or 5% w/v in the carrier. The scaffold material comprising natural-polymer or non-polymer particles, such as ceramic, may comprise about 1% w/v plasticiser in the carrier.

The natural-polymer particles or non-polymer particles may be microparticles. The non-polymer particles may comprise or consist of ceramic. The ceramic may comprise or consist of calcium sulphate (CS) or β-tricalcium phosphate (β-TCP). In another embodiment, the natural-polymer particles or non-polymer particles may comprise crystallised sugar molecules, such as crystallised particles of mannitol. Other sugar particles may be provided, such as glucose. In one embodiment, the natural-polymer particles or non-polymer particles may comprise anti-oxidant.

The plasticiser may comprise PEG. The mixture for hot-melt extrusion may comprise PEG.

Both natural-polymer particles and non-polymer particles may be provided for encapsulation with the polymer into the hollow polymer pellets.

The polymer for blending with the natural-polymer or non-polymer particles may comprise at least 30% of the mixture. In another embodiment, the polymer for blending with the natural-polymer or non-polymer particles may comprise at least 40% of the mixture. In another embodiment, the polymer for blending with the natural-polymer or non-polymer particles may comprise at least 45% of the mixture. In another embodiment, the polymer for blending with the natural-polymer or non-polymer particles may comprise at least 48% or 49% of the mixture. In another embodiment, the polymer for blending with the natural-polymer or non-polymer particles may comprise at least 50% of the mixture. In another embodiment, the polymer for blending with the natural-polymer or non-polymer particles may comprise at least 60%, 70% or 80% of the mixture. In another embodiment, the polymer for blending with the natural-polymer or non-polymer particle may comprise at least 90% of the mixture.

In one embodiment, the hollow polymer pellets may comprise between about 10% and about 50% of natural-polymer or non-polymer particles; between about 40% and 85% polymer; and between about 1% and about 10% plasticiser, wherein the total amounts do not exceed 100%.

Method/System of Modifying Scaffold Forming Properties

Advantageously, the use of plasticiser in the carrier at a range of concentrations can provide control over the scaffold setting properties of a scaffold material according to the invention, such that a preferred setting temperature or a preferred setting time can be achieved.

According to another aspect of the present invention, there is provided a method of forming a scaffold material which is capable of setting in less than 5 minutes, wherein the scaffold material is provided in accordance with any of the methods of the invention herein, and wherein the plasticiser is provided in the carrier in a range of between about 4% w/v and about 6% w/v.

According to another aspect of the present invention, there is provided a method of forming a scaffold material having a scaffold setting time of between about 5 and about 15 minutes, wherein the scaffold material is provided in accordance with any of the methods of the invention herein, and wherein the plasticiser is provided in the carrier in a range of between about 2.5% w/v and about 3.5% w/v.

According to another aspect of the present invention, there is provided a method of forming a scaffold material having a scaffold setting time of greater than 60 minutes, wherein the scaffold material is provided in accordance with any of the methods of the invention herein, and wherein the plasticiser is TA or TEC and is provided in the carrier in the range of between about 0.5% w/v and about 1% w/v.

According to another aspect of the present invention, there is provided a method of forming a scaffold material having a scaffold setting temperature of less than 35 degrees C., wherein the scaffold material is provided in accordance with any of the methods of the invention herein, and wherein the plasticiser is TA or TEC and is provided in the carrier in a range of between about 3% w/v and about 5% w/v; or
  alternatively two plasticisers are provided, with at least one plasticiser in the carrier and the total plasticiser content may not exceed 4% or 5% w/v, wherein one plasticiser is TA or TEC, optionally, wherein the TA or TEC are provided up to 2% w/v of the carrier.

According to another aspect of the present invention, there is provided a method of forming a scaffold material having a scaffold setting temperature of greater than 35 degrees C., for example about 37 degrees C., wherein the scaffold material is provided in accordance with any of the methods of the invention herein, and wherein the plasticiser is TA or TEC and is provided in a range of between about 0.5% w/v and about 1% w/v.

According to another aspect of the invention, there is provided a system for selecting hollow polymer pellet scaffold formation properties comprising:
  (a) selecting a desired scaffold setting temperature and carrying out a method of forming a scaffold material according to the invention herein, which is arranged to provide the appropriate scaffold setting temperature; or
  (b) selecting a desired scaffold setting time and carrying out a method of forming a scaffold material according to the invention herein, which is arranged to provide the appropriate scaffold setting time; or
  (c) selecting a desired scaffold material Young's modulus prior to setting of the scaffold, and carrying out a method of forming a scaffold material according to the invention herein, which is arranged to provide the appropriate scaffold material Young's modulus.

According to another aspect of the present invention, there is provided a method of forming a scaffold material suitable for forming a scaffold having a $1^{st}$ order agent release kinetic, wherein the scaffold material is provided in accordance with methods of the invention herein, and wherein the agent is provided as a powder prior to blending with polymer to form the hollow polymer pellets of the scaffold material.

Composition—Scaffold Material Pre-Scaffold Formation

According to a yet further aspect, the invention provides a scaffold material produced by any method of the invention.

According to another aspect of the invention, there is provided scaffold material for forming a scaffold for controlled release of an agent, wherein the scaffold material comprises:
  hollow polymer pellets;
  an agent, wherein the agent is in a powder form and is encapsulated amongst and between the hollow polymer pellets; and
  a liquid carrier suspending the hollow polymer pellets.

According to another aspect of the invention, there is provided scaffold material for forming a scaffold, wherein the scaffold material comprises:
  hollow polymer pellets;
  natural-polymer particles and/or non-polymer particles (such as ceramic), wherein the natural-polymer particles and/or non-polymer particles are encapsulated within the hollow polymer pellets; and optionally
  a liquid carrier suspending the hollow polymer pellets.

In one embodiment, the scaffold or scaffold material may be suitable for bone repair.

According to another aspect of the invention, there is provided scaffold material for forming a scaffold, wherein the scaffold material comprises:
  hollow polymer pellets;
  a liquid carrier suspending the hollow polymer pellets, wherein the liquid carrier comprises a plasticiser; and optionally wherein a second plasticiser is provided in the carrier and/or the hollow polymer pellets.

Scaffold (Post-Formation)

According to a yet further aspect, the invention provides a scaffold produced by any method of the invention.

According to another aspect of the invention, there is provided a scaffold for controlled release of an agent, wherein the scaffold comprises:
  inter-linked hollow polymer pellets; and
  an agent, wherein the agent is in a powder form and is encapsulated amongst and between the hollow polymer pellets.

According to another aspect of the invention, there is provided a scaffold for bone repair, wherein the scaffold comprises:
inter-linked hollow polymer pellets; and
natural-polymer particles and/or non-polymer particles (such as ceramic), wherein the natural-polymer particles and/or non-polymer particles are encapsulated within the hollow polymer pellets.

In a further aspect, the invention provides a method of delivering an agent to a subject comprising providing a scaffold material, wherein the agent is located within hollow polymer pellets within the scaffold material; administering the scaffold material to a subject; allowing the scaffold material to solidify/self-assemble in the subject to form a scaffold; and allowing the agent contained within the scaffold material to be released into the subject at the site of administration.

The method may be practised on tissue in vivo or in vitro.

The agent (encapsulated within hollow polymer pellets) may optionally be added to the scaffold material immediately prior to administration to the subject.

In one embodiment, in step d) the agent release is sustained over a period at least 12 hours.

The scaffold material or scaffold may be for use in a method of treatment or prevention of a condition selected from: neurodegeneration disorders (e.g. post stroke, Huntington's, Alzheimer's disease, Parkinson's disease), bone-related disorders (including osteoarthritis, spinal disk atrophy, bone cavities requiring filling, bone fractures requiring regeneration or repair), burns, cancers, liver disorders (including hepatic atrophy), kidney disorders (including atrophy of the kidney), disorders of the bladder, ureter or urethra (including damaged ureter or damaged bladder requiring reconstruction, prolapse of the bladder or the uterus), diabetes mellitus, infertility requiring IVF treatment, muscle wasting disorders (including muscular dystrophy), cardiac disorders (e.g. damaged cardiac tissue post myocardial infarction, congestive heart disease), eye disorders (e.g. damaged or diseased cornea), damaged vasculature requiring regeneration or repair, ulcers, and damaged tissue requiring regeneration or reconstruction (including damaged organ requiring regeneration or reconstruction, and damaged nerves requiring regeneration or reconstruction).

In some embodiments the treatment is dental bone repair, such as dental ridge restoration. In other embodiments the treatment is the repair of non-union fractures. In other embodiments the treatment is spinal fusion.

Dental bone graft substitutes are primarily used in implant procedures requiring additional bone support. Bone regeneration is enhanced with advanced products, allowing dental bone grafting procedures to be performed on patients who would otherwise not be able to receive such treatment. In approximately 40% of all dental implant cases, there is not enough bone to ensure proper implant integration, and bone graft substitutes are required. Tooth extraction can result in deterioration of alveolar bone, resulting in a chronic progressive condition termed residual ridge resorption (RRR). Standard bone grafting options result in secondary lesions, immunologic rejection and poor long-term outcomes. Osteoinductive factors released from a non-immunogenic delivery system could provide an answer.

Grafting techniques are making it possible to expand the candidate pool for implants to include a sizable population of edentulous patients who were poor candidates for dental implantation due to severe bone resorption.

Treatments that positively influence bone healing following fracture, and subsequently shorten the time necessary for bone union are of great interest. Surgical intervention in non-unions is required to re-expose living tissue and to insert an osteoinductive graft material. Using autograft or allograft material, this treatment is successful in 70-80% of cases and costs an estimated $14,000 per patient. There is therefore much interest in more effective graft materials.

Spinal fusion is used to surgically treat vertebral abnormalities such as spinal curvatures (scoliosis or kyphosis), slipped discs (following discectomy), or fractures. The procedure uses graft materials (with or without pedicle screws, plates or cages) or other devices to fuse vertebrae together. Many patients complain of donor site pain from the autograft harvest for up to 2 years postoperatively. These complications have driven the search for and subsequent use of alternatives. The invention provides such alternatives in the form of the systems, compositions and methods described herein.

The scaffold or scaffold material formed by any method and/or composition of the invention may be used to treat damaged tissue. In particular, the scaffold or scaffold material may be used to encourage or allow cells to re-grow in a damaged tissue. The invention may therefore be used in the treatment of tissue damage, including in the regeneration or reconstruction of damaged tissue.

The scaffold material of the invention may be used to produce scaffolds for use in the treatment of a disease or medical condition, such as, but not limited to, Alzheimer's disease, Parkinson's disease, osteoarthritis, burns, spinal disk atrophy, cancers, hepatic atrophy and other liver disorders, bone cavity filling, regeneration or repair of bone fractures, diabetes mellitus, ureter or bladder reconstruction, prolapse of the bladder or the uterus, IVF treatment, muscle wasting disorders, atrophy of the kidney, organ reconstruction and cosmetic surgery.

According to another aspect of the present invention there is provided a method of treatment comprising the administration of a scaffold or scaffold material according the invention.

According to a yet further aspect, the invention provides a method of treating a subject, such as a mammalian organism, to obtain a desired local physiological or pharmacological effect comprising administering a scaffold material according to the invention to a site in the subject (e.g. the organism) in need of such treatment. Preferably the method allows the agent to be delivered from the scaffold to the area surrounding the site of scaffold formation.

According to a further aspect, the invention provides the use of a scaffold material according to the invention as an injectable scaffold material in tissue regeneration and/or in the treatment of tissue damage.

The product of the invention may be used for the treatment or prevention of a condition selected from: neurodegeneration disorders (e.g. post stroke, Huntington's, Alzheimer's disease, Parkinson's disease), bone-related disorders (including osteoarthritis, spinal disk atrophy, bone cavities requiring filling, bone fractures requiring regeneration or repair), burns, cancers, liver disorders (including hepatic atrophy), kidney disorders (including atrophy of the kidney), disorders of the bladder, ureter or urethra (including damaged ureter or damaged bladder requiring reconstruction, prolapse of the bladder or the uterus), diabetes mellitus, infertility requiring IVF treatment, muscle wasting disorders (including muscular dystrophy), cardiac disorders (e.g. damaged cardiac tissue post myocardial infarction, congestive heart disease), eye disorders (e.g. damaged or diseased cornea), damaged vasculature requiring regeneration or repair, ulcers, and damaged tissue requiring regeneration or reconstruction (including damaged organ requiring regeneration or reconstruction, and damaged nerves requiring regeneration or reconstruction).

According to another aspect, the invention provides a kit for use in delivering an agent to a target comprising:
  hollow polymer pellets;
  powdered agent; and
  a carrier solution; and optionally
  instructions to mix the hollow polymer pellets, powdered agent and carrier.

The hollow polymer pellets and powdered agent may be pre-mixed. In another embodiment, the hollow polymer pellets, carrier and powdered agent may be pre-mixed. In another embodiment, the carrier and powdered agent may be pre-mixed.

According to another aspect, the invention provides a kit for use in forming a scaffold comprising:
  hollow polymer pellets;
  natural-polymer particles and/or non-polymer particles; and
  a carrier solution; and optionally
  instructions to mix the hollow polymer pellets, natural-polymer particles and/or non-polymer particles and carrier.

The hollow polymer pellets and powdered agent may be pre-mixed. In another embodiment, the natural-polymer particles and/or non-polymer particles, hollow polymer pellets and powdered agent may be pre-mixed. In another embodiment, the natural-polymer particles and/or non-polymer particles, hollow polymer pellets, carrier and powdered agent may be pre-mixed.

According to another aspect, the invention provides a kit for use to form a scaffold comprising:
  hollow polymer pellets; and
  a carrier solution comprising a plasticiser; and optionally the hollow polymer pellets and/or the carrier comprise a second plasticiser; and further optionally
  instructions to mix the hollow polymer pellets and carrier.

The plasticiser may be provided separately for mixing with the carrier.

The kit may include a syringe for use in injecting the scaffold material. The kit may further include cells and/or active agents for mixing with the scaffold material. The kit may be stored either refrigerated or at room temperature.

The skilled man will appreciate that the optional features of the first aspect, or any aspect or embodiment, of the invention can be applied to all aspects of the invention.

Embodiments of the invention will now be described, by way of example only, with reference to the following examples.

Example 1—Polymer Pellet Scaffolds

This document discusses research into the development of smart pastes, able to set at different times and at different temperatures, to be used alone or in combination with drugs, growth factors, genes or cells. In this example, these pastes were made by two main components, PLGA or PLGA/ceramic pellets and a liquid carrier.

Whilst the examples of Example 1 are provided in relation to non-hollow polymer pellets, the skilled person will understand that the same principles will apply in terms of scaffold setting and formation properties and conditions (with exception of the advantages identified in Example 2 and the invention herein for using a hollow polymer pellet).

Calcium sulphate (CS) and β-Tricalcium Phosphate (β-TCP) are the ceramic investigated. They have previously been shown to induce bone formation in vivo and act to reduce the overall cost of goods of a potential end product. It was therefore investigated if ceramics could be included for this indication and how they would affect the properties of the final product.

Provided is a method to control the setting of said pastes by using liquid carriers with two different plasticizers (TEC and EtOH) and different concentrations of them. They have been tested with pellets of different composition and size.

When a plasticiser, such us TEC, is used in the liquid carrier, the use of PEG can be avoided. In this way, PLGA pellets and not only PLGA/PEG pellets could be used. Additionally, when a plasticiser, such us TEC, is used in the liquid carrier it is possible to sinter pellets made by PLGA/ceramic blends. Furthermore, by choosing the concentration of TEC it is possible to control the setting properties of the TAOS material.

Example—Paste Setting Control Over Time and Temperature

Pastes were prepared by mixing pellets with a liquid carrier and their setting was assessed using an 'in house' cohesion test. Briefly, following paste sintering, aluminium foils containing the pastes were placed onto a sieve mesh and immersed to a depth of around 1 cm of water for 1 minute (FIG. 1). Afterwards, they were carefully removed from the sieve. The samples were freeze-dried and weighed so that mass loss could be estimated.

FIG. 2-5 show the mass loss from different pastes sintered for 15 min at room temperature or 37° C. FIG. 6 shows the mass loss of pastes sintered at different time points (from 10 to 60 min.) at 37° C.

Materials
Liquid Carriers:
  0.5% w/v CMC, 1% w/v Pluronic F127 in 0.9% w/v Sodium Chloride.
  1% w/v TEC, 0.5% w/v CMC, 1% w/v Pluronic F127 in 0.9% w/v Sodium Chloride.
  2.5% w/v TEC, 0.5% w/v CMC, 1% w/v Pluronic F127 in 0.9% w/v Sodium Chloride.
  5% w/v TEC, 0.5% w/v CMC, 1% w/v Pluronic F127 in 0.9% w/v Sodium Chloride.
  5% w/v EtOH, 0.5% w/v CMC, 1% w/v Pluronic F127 in 0.9% w/v Sodium Chloride.
  10% w/v EtOH, 0.5% w/v CMC, 1% w/v Pluronic F127 in 0.9% w/v Sodium Chloride.
Pellets:
  PLGA 50:50 (50-100 μm pellets).
  75.6% w/w PLGA50:50, 5.2% w/w PEG400, 20% w/w SIM (300-400 μm HME pellets).
  46.75% w/w PLGA 95:5, 3.25% w/w PEG400, 50% w/w CS (300-400 μm HME pellets).
  46.75% w/w PLGA 95:5, 3.25% w/w PEG400, 50% w/w β-TCP (300-400 μm HME pellets).
Method
  A 355 μm sieve (Endecotts, B5410/1986) was placed on to its dedicated collection tray.
  2×100 mg of pellets were manually mixed in an aluminium foil (4×4 cm circa) with 70 μl of each liquid carrier.
  The obtained pastes were left to sinter in a sealed plastic bag with humidity >90% for different times.
  Following sintering at RT or 37° C. in a humidified environment (>90% RH), the aluminium foils containing the pastes were placed onto the sieve mesh.

A constant, gentle, circa 7 ml/sec flow of water (Millipore, Direct-Q® 3 UV) was applied to the sieve mesh, until the samples became immersed in circa 1 cm of water.

Following immersion, samples were allowed to remain immersed in the head of water for circa 1 minute.

After the 1 minute, the sieve was removed from the sieve tray and the aluminium foils containing the samples were carefully removed from the sieve.

The samples with the aluminium foil were freeze-dried and weighed so that mass loss could be estimated.

The sieve tray (which was still filled with water) was visually inspected for the presence of pellets that may have been lost from the samples during.

FIG. 2 shows that using a liquid carrier containing a plasticizer, it is possible to use PLGA pellets that are not blended with the plasticizer PEG400. This is important because removing the plasticizer from the blend will give a leaner manufacturing process and improve the room temperature stability of the pellets. In fact, because of the low glass transition temperatures of PLGA/PEG400 blends, they need to be stored in fridge or freezer.

FIG. 2-5 demonstrates that increasing the TEC concentration in the liquid carrier produces pastes with fast setting properties. Except for the 50% w/w TCP pellets (FIG. 4), the liquid carrier containing 1% w/v TEC gave pastes able to set at 37° C. and not at room temperature. Instead, with the liquid carrier containing 5% w/v TEC, pastes were obtained which were very fast setting and had a putty-like consistency.

FIG. 6 shows how the paste cohesion is affected by time and that the presence of ethanol in the liquid carrier is not important for paste setting.

Paste Mechanical Property Control Over Time and Temperature (Strength)

Mechanical properties of the paste-formed scaffolds were assessed. Scaffold strength of 6×12 mm cylindrical scaffolds (FIG. 7) was assessed after 15 min, 2 and 24 h sintering, using a 'Stable Microsystems' texture analyser following the Locate Therapeutics testing protocol. PLGA or PLGA/CS pellets were investigated.

Materials
Liquid Carriers:
3% w/v TEC, 0.5% w/v CMC, 1% w/v Pluronic F127 in 0.9% w/v Sodium Chloride.
Pellets:
PLGA 50:50 (50-200 µm pellets).
50% w/w PLGA50:50, 50% w/w CS (50-200 µm pellets).
Method 6×12 mm cylindrical scaffolds were produced by syringe mixing PLGA or PLGA/CS (50-200 µm) pellets with 3% w/v TEC carrier at a 1.5:1 ratio, injecting to a PTFE mould and sintering at either 32° C. or 37° C. for 15 minutes and 2 hours or 24 hours either immersed in PBS (wet) or sealed in a >90% humid atmosphere at 37° C. (FIG. 7). Mechanical testing was carried out according to ISO standard by using a texture analyser.

The obtained results demonstrate that scaffolds were formed after 15 min sintering using both PLGA and PLGA/CS pellets. Nevertheless, the addition of CS resulted in weaker scaffolds (FIG. 8 and FIG. 10).

When PLGA5050 was used, 15 min sintering at 32° C. or 37° C. has no effect on scaffold strength. Instead, 2 h sintering gave strongest scaffolds at 32° C. (FIG. 8).

Comparison between damp and wet sintering (FIG. 9-10) demonstrates that the strongest scaffolds are those sintered in wet conditions.

Paste Mechanical Property Control Over Time and Temperature (Flow Ability)

Materials
Liquid Carriers:
2% w/v TEC, 0.5% w/v CMC, 1% w/v Pluronic F127 in 0.9% w/v Sodium Chloride.
3% w/v TEC, 0.5% w/v CMC, 1% w/v Pluronic F127 in 0.9% w/v Sodium Chloride.
4% w/v TEC, 0.5% w/v CMC, 1% w/v Pluronic F127 in 0.9% w/v Sodium Chloride.
10% w/v EtOH, 0.5% w/v CMC, 1% w/v Pluronic F127 in 0.9% w/v Sodium Chloride.
Pellets:
PLGA 50:50 (50-200 µm pellets).
50% w/w PLGA50:50, 50% w/w CS (50-200 µm pellets).
Method Viscosity was determined by ejecting 4004 mixed putty onto an acetate sheet set to an angle of 45°. Putty was ejected directly from the syringe at a steady rate, and allowed to flow down the slope for 60 seconds before a second mark was made to indicate how far the putty had run. The distance was then calculated and average values obtained.

The results show that by reducing the amount of carrier to polymer ratio before mixing, a much thicker paste can be generated, regardless of the carrier components. By increasing plasticizer concentration it is possible to create a more viscous initial material, but only to a limit dependent on the material, after which further increases in plasticiser make little difference (FIG. 12). Further results demonstrate that the addition of calcium sulphate has a great impact on the flowability of mixed and ejected material (FIG. 13).

This technology can be exploited in the medical healthcare area. Applications include an injectable delivery system for use in cellular therapies which encourages the formation of 3D tissue structures to give enhanced functionality e.g. dental, bone defects, bone fractures, spine fusion and cartilage. The market for orthopaedic materials is vast, and growing in line with the aging population. As such, novel, cost effective therapy products are vital in maintaining healthcare standards and keeping costs to reasonable levels.

1. Terminology

β-TCP: β-tricalcium phosphate, CMC: Carboxymethyl cellulose, CS: Calcium suplphate, EtOH: Ethanol, F127: Pluronic® F127, HME: Hot Melt Extrusion, PEG: Polyethene glycol, PLGA: Poly(lactic-co-glycolic acid), TEC: TriEthyl Citrate

REFERENCES

1—M. Artico, L. Ferrante, F. S. Pastore et al., "Bone autografting of the calvaria and craniofacial skeleton: historical background, surgical results in a series of 15 patients, and review of the literature," Surgical Neurology, vol. 60, no. 1, pp. 71-79, 2003.

2—Y. T. Konttinen, D. Zhao, A. Beklen et al., "The microenvironment around total hip replacement prostheses," Clinical Orthopaedics and Related Research, no. 430, pp. 28-38, 2005.

3—L. G. Mercuri and A. Giobbie-Hurder, "Long-term outcomes after total alloplastic temporomandibular joint reconstruction following exposure to failed materials," Journal of Oral and Maxillofacial Surgery, vol. 62, no. 9, pp. 1088-1096, 2004.

4—A. M. Pou, "Update on new biomaterials and their use in reconstructive surgery," Current Opinion in Otolaryngology and Head and Neck Surgery, vol. 11, no. 4, pp. 240-244, 2003.

5—R. Langer and J. P. Vacanti, "Tissue engineering," Science, vol. 260, no. 5110, pp. 920-926, 1993.

Example Scaffold Properties

| Batch No. | Batch Name | Maximum stress (MPa) | | | | Young's modulus (MPa) | | | | |
|---|---|---|---|---|---|---|---|---|---|---|
| | | EtOH | | TEC | | EtOH | | TEC | | |
| | | 2 h | 24 h | 2 h | 24 h | 2 h | 24 h | 2 h | 24 h | |
| 1 | P90110 | 0.15 | 3.63 | 1.14 | 4.27 | 3.4 | 36.4 | 9.2 | 41.7 | |
| 2 | P80120 | 0.07 | 3.26 | 1.07 | 3.82 | 2.7 | 16.5 | 8.6 | 25.6 | |
| 3 | P70130 | 0.07 | 2.89 | 0.84 | 4.15 | 3.4 | 39.4 | 6.4 | 42.9 | |
| 4 | P60140 | 0.07 | 2.69 | 0.73 | 2.54 | 4.8 | 22.4 | 5.1 | 20.0 | 37° C. |
| 5 | P50150 | 0.10 | 1.48 | 0.55 | 2.20 | 2.0 | 29.2 | 3.2 | 25.0 | |
| 4 | P60140 | 0.81 | 3.73 | 2.01 | 4.21 | 7.5 | 40.9 | 5.1 | 26.0 | |
| | | | | | | | | | | 41.5° C. |
| 5 | P50150 | 0.75 | 2.51 | 1.39 | 3.68 | 17.3 | 29.4 | 1.4 | 27.1 | |

Maximum stress and Young's modulus after 2 or 24 h sintering at 37° C. or 41.5° C. of non-hollow polymer pellets. In 'batch name' column, P and T refer to PLGA/PEG and β-TCP respectively. EtOH and TEC were used as plasticisers in the liquid carrier at the concentration of 5% w/v and 2.5% w/v respectively.

Example—TAOS™ Pellets Production by HME Process

Summary

This example describes a general protocol to produce TAOS™ pellets by using the hot melt extrusion technique.

TAOS™ is a PLGA-based material that can be blended with biodegradable and biocompatible material such as ceramics (i.e. Calcium sulphate, tricalcium phosphate) and polymers (i.e. PEGs, Pluronics, etc). TAOS™ can deliver active ingredients and biologicals.

Each blend is composed at least by two components where one component is PLGA. The methodology described in this document consist of 3 main steps:

Dry pre-mixing of the materials
Hot melt extrusion of the pre-mixed material
Pelletisation of the extrudate Using this protocol pellets of 300-400 microns are obtained. When smallest particles are required, the further step of cryomilling is required.

Materials
PLGA 50:50 4.5A, Evonik, Lot No. LP1042
PLGA 85:15 4A, Evonik, Lot No. LP717
PLGA 95:5 6E, Evonik, Lot No. LP1075
Pluronic F127, Sigma, Lot no 121K0070
PEG 400, Clariant, Lot No. DEG4242071
Simvastatin, Teva, Lot No. 86600300414
Calcium Sulphate (CS), Sigma-Aldrich, Lot No. MKBR2597V
β-TCP, Plasma-Biotal, Lot No. XRD7065

Method

Dry Pre-Mixing

Mixing is performed by hand in triple bagged samples of at least 30 g, breaking up larger particles as they are identified and remixing into the blend. Once finding agglomerates to break down became hard, the blend is passed through an 850 microns screen with particles separated out in this process broken down and recombined with the main material feedstock. The recombined feedstock is then thoroughly mixed ready for hot melt extrusion. In this manner, consistent feeding of each material is achieved using a twin screw mini-feeder into the hot melt extruder.

Agglomerates occur when PEG400 or other sticky liquid materials are used in combination with PLGA.

PLGA, simvastatin and Pluronic F127 should be less than 500 microns prior to use.

The β-TCP and the CS should be between 20 and 52 microns.

Hot Melt Extrusion

The pre-mixed material is then introduced into the HME feeding zone through a twin screw mini-feeder. Varying the feed rates of the material to the extruder, from 1.1 to 2.3 g/min$^{-1}$, it is possible to change the extrudate diameter from 300-350 microns to 800-900 microns.

Standard HME barrel temperatures are shown below. The extruder screw speed is set at 50 rpm.

Barrel Temperature Profiles:

| Die (° C.) | Zone7 (° C.) | Zone6 (° C.) | Zone5 (° C.) | Zone4 (° C.) | Zone3 (° C.) | Zone2 (° C.) | Powder inlet (° C.) |
|---|---|---|---|---|---|---|---|
| 90 | 90 | 90 | 90 | 90 | 90 | 50 | 25 |

Pelletisation

The extrudate coming from the HME die zone is then cut into pellets using a pelletiser with the setting 9L1. With this setting pellets of 300-400 microns are obtained.

The pelletiser is composed by 2 main components:
1 cutting wheel
2 concentric wheels that push the extrudate to the cutting wheel.

The cutting wheel can rotate at different speed (control dial from 1 to 9). Instead, the 2 concentric wheels can push the extrudate at four different speeds (control dial from 1 to 4). In the combination 9L1, 9 refers to the cutting wheel while 1 refers to the concentric wheels.

Prepared Batches

Using the described methodology following HME batches were produced:

TAOS-TCP
84.15% w/w PLGA95:5, 5.85% PEG400, 10% w/w β-TCP
74.8% w/w PLGA95:5, 5.2% PEG400, 20% w/w β-TCP
65.45% w/w PLGA95:5, 4.55% PEG400, 30% w/w β-TCP
56.1% w/w PLGA95:5, 3.9% PEG400, 40% w/w β-TCP
46.75% w/w PLGA95:5, 3.25% PEG400, 50% w/w β-TCP

TAOS-TCP/TAOS-CS/TAOS-Pluronic

Batch LOC01—46.75% w/w PLGA95:5, 3.25% PEG400, 50% w/w β-TCP

Batch LOC02—46.75% w/w PLGA95:5, 3.25% PEG400, 50% w/w CS

Batch LOC03—84.15% w/w PLGA50:50, 5.85% PEG400, 10% w/w Pluronic F127

Batch LOC04—65.45% w/w PLGA50:50, 4.55% PEG400, 10% w/w Pluronic F127, 20% w/w Simvastatin TAOS-SIM

| Batch Output | Polymer | PEG 400 (w.r.t. PLGA) | Simvastatin | Feed Rate | Pelletiser Rate |
|---|---|---|---|---|---|
| 200 g | PLGA 95:5 | 6.5% | 0% | 1.1 g/min | 9L1 |
| 200 g | PLGA 50:50 | 6.5% | 20% | 1.1 g/min | 9L1 |
| 200 g | PLGA 50:50 | 6.5% | 0% | 1.1 g/min | 9L1 |
| 200 g | PLGA 85:15 | 6.5% | 0% | 1.1 g/min | 9L1 |
| 100 g | PLGA 95:5 | 6.5% | 20% | 1.1 g/min | 9L1 |
| 100 g | PLGA 85:15 | 6.5% | 20% | 1.1 g/min | 9L1 |

Example 2—Hollow Polymer Pellets

Manufacture

1. Introduction

The aim of the work was to produce hollow micro pellets of PLGA based tube.

Hollow polymer pellets can generally be produced in a 3 step process.

1st step: preparation of standard pellets (300 um diameter, 500 um length) by twin screw extrusion of dry raw materials, followed by pelletisation. (See 'Example—TAOS' pellets production by HME process' above)

2nd step: preparation of hollow tubes by single screw extrusion of the standard pellets prepared in step 1.

3rd step: pelletisation of the hollow tubes prepared in step 2 to get hollow pellets (450-500 um diameter, 500 um length).

2. Experimental

Two batches (approx. 200 g) of material were pre-compounded and provided. Based on a PLGA matrix, one grade (PLGA-PEG) contained 6.5% w/w polyethylene glycol 400; the second grade (PLGA-CS-PEG) also contained 50% w/w loading of calcium sulphate filler.

PLGA-PEG Batch:
PLGA95:5=93.5% w/w
PEG400=6.5% w/w
PLGA-CS-PEG Batch:
PLGA95:5=46.75% w/w
PEG400=3.25% w/w
CS=50% w/w A single screw extruder (Dr Collin Teachline16) with a screw diameter of 16 mm was used, equipped with a tube die with an outer diameter of 2.0 mm and an inner (pin) diameter of 1.0 mm. Extruded tube was drawn down (stretched) to a target outer tube diameter of 400 μm using a Rondol caterpillar haul-off unit. Due to the water sensitive nature of the polymer, a water free cooling system was used whereby the extruded tube was allowed to cool in air whilst supported by a PTFE guide channel. Extruded tube was wound onto a spool using an automated winder. Pelletisation was performed using a Thermo Scientific pharma grade pelletiser, set at maximum cutter speed.

Initial set-up of the extrusion, haul-off and pelletisation process was performed using a non-medical grade of PLGA, which was available in larger quantities within the IRC laboratories. This allowed temperature profile, extruder speed and haul-off speed to be established before using the smaller material medical grade samples. The unfilled, non-medical grade was found to extrude well and a tube of around 500 μm was produced. This was cut into micro pellets of the target dimensions.

3. PLGA-CS-PEG Extrusion

Single screw extruder set temperatures used for PLGA-CS-PEG are detailed in Table 1.

TABLE 1

| Extrusion set temperatures (° C.) | |
|---|---|
| Barrel Zone 1 | 25 |
| Barrel Zone 2 | 90 |
| Barrel Zone 3 | 100 |
| Barrel Zone 4 | 100 |
| Die Adaptor | 100 |
| Die | 100 |

The compound extruded well and produced a tube which was readily drawn down to the required diameter by the haul-off unit caterpillar. After an initial period of set-up and stabilisation the process was allowed to run in order to collect a sufficient quantity of extruded tube. The extruder screw speed was set at 36 rpm and the haul-off speed was set to 18 m/min. Extruded tube was subsequently pelletised at maximum cutter rotation speed. SEM images of the cut tubes are shown in FIG. 14.

The cut extruded tube was placed in a heat-sealed foil bag under a nitrogen and later analysed.

4. PLGA-PEG Extrusion

PLGA-PEG was fed into the single screw extruder at the same set process conditions for creation of PLGA-CS-PEG pellets.

5. Summary Comments

The extrusion process was used to successfully produce tube at the target dimensions without water cooling. The material was found to be well suited to extrusion at these conditions and the process could be run in a stable manner. Extruded tube was cut to the target pellet size using a commercial pelletiser typically used for pharmaceutical compounding. A full purge, strip and clean of the extruder and die is recommended between different batches of material.

Characterisation of Hollow Polymer Pellets

Standard TAOS-CS Pellets (TAOS-CS) vs. Hollow TAOS-CS Pellets (H-TAOS-CS)

Scope

Work to date demonstrated that when calcium sulphate (CS) was included within the TAOS™ systems, a better bone regeneration was achieved. The data showing this improvement were obtained in a New Zealand White condyle rabbit model study and the TAOS-CS blend used had 50% w/w CS. This blend was produced by HME twin screw extrusion followed by pelletisation. The dimension of the obtained pellets was of 300 um diameter and 400 um length. In the condyle study these pellets were mixed with a liquid carrier to create a paste that was then implanted in the rabbit condyle.

It is well known that bone regeneration it is influenced by the porosity of the implants. Porosity greater than 60% and pores bigger than 50 um allow the cells to well proliferate and differentiate within the implant enhancing thus the regenerative process.

In order to improve the implant porosity the use of hollow pellets were investigated. The aim was to have pellets with similar attributes of the standard pellets (no-hollow) but with increased porosity.

The purpose of this study was then the comparison of the physical attributes of pastes/scaffolds made by standard TAOS-CS pellets (300×400 um circa) or by hollow TAOS-CS pellets (400×550 um circa). The physical attributes of porosity, strength, glass transition temperature and cohesion were evaluated and described.

Materials
TAOS™-CS pellets (standard and hollow)
  PLGA 95:5 DLG 6E 75 KDa
  PEG 400
  Calcium Sulphate Batch No. MKBR2597V (Sigma-Aldrich)
Standard TAOS Liquid Carrier
  Saline: 0.9% w/v sodium chloride in distilled water
  Pluronics F127
  Carboxymethylcellulose 12M31P
Plasticiser
  Triacetin Terminology CMC: Carboxymethyl cellulose, CS: Calcium sulphate, DMA: Dynamic mechanical analysis, F127: Pluronic® F127, HME: Hot Melt Extrusion, TAOS: Targeted Orchestrated Signalling, TAOS-CS: standard pellets of TAOS+Calcium sulphate, H-TAOS-CS: hollow pellets of TAOS+Calcium sulphate, PEG: Polyethene glycol, PLGA: Poly(lactic-co-glycolic acid), TA: triacetin Method Test Sample Paste Preparation For paste preparation, 100 mg circa of TAOS-CS or H-TAOS-CS pellets were weighed out in a piece of aluminium foil (4×4 cm circa) and mixed manually into a mound, using a small spatula, with 70 μl TAOS™ liquid carrier (standard or standard+2.5% w/v TA). After mixing, the pastes were transferred at 37° C. and left to sinter for 15 min in a PBS humidified sealed bag (>90% RH).

TAOS™ Paste Cohesiveness/Early Scaffold Integrity Evaluation

For the evaluation of TAOS™-ceramic paste cohesiveness/early scaffold integrity the methodology was as follows:

A 355 μm sieve (Endecotts, BS410/1986) was placed on to its dedicated collection tray.

Following 15 min sintering at 37° C. in a humidified environment (>90% RH), the aluminium foils containing the early scaffolds were placed onto the sieve mesh.

A constant, gentle, circa 7 ml/sec flow of water (Millipore, Direct-Q® 3 UV) was applied to the sieve mesh, until the samples became immersed in circa 1 cm of water.

Following immersion, samples were allowed to remain immersed in the head of water for circa 1 minute.

After the 1 minute, the sieve was removed from the sieve tray and the aluminium foils containing the samples were carefully removed from the sieve.

The samples with the aluminium foil were freeze-dried and weighed so that weight loss could be estimated.

The sieve tray (which was still filled with water) was visually inspected for the presence of particles that may have been lost from the samples during.

Scaffolds Preparation

For scaffold preparation, 200 mg of the TAOS-CS or H-TAOS-CS pellets were weighed out in a weigh boat and mixed manually, using a small spatula, with 140 μl of TAOS' liquid carrier (standard or standard+2.5% w/v TA). After mixing, the pastes were transferred into 6×12 mm PTFE moulds and depending on the experiment, left to sinter at 37° C. for 2 or 24 hours in a PBS humidified sealed bag (humidity >90%). Scaffolds for porosity were dry sintered (no liquid carrier), freeze-dried and weighed after the sintering process.

Porosity Assessment

Scaffold porosity was determined by the 'density method'. The mass of each freeze-dried scaffold was measured along with the volume ($V=\pi r^2 h$). Density was calculated using the following equation:

Density=Mass/Volume

Subsequently, assuming that the densities of PLGA, CS are respectively 1.3, 2.96 g/cm$^3$, porosity was calculated.

Molecular Weight Assessment

The impact of twin and single screw extrusion processes on PLGA95:5 molecular weight was assessed. Twin and single screw extruder were used for manufacturing standard polymer pellets (TAOS-CS) and hollow polymer pellets (H-TAOS-CS), respectively.

To assess the PLGA95:5 molecular weight, standard and hollow polymer pellets were dissolved in acetonitrile:water (1:1) solution first. This solution was then filtered to remove insoluble calcium sulfate. Molecular weight of filtered solutions were analysed under HPLC by using GPC column.

Scaffold Strength Test

Scaffold strength was checked after 2 and 24 h of sintering, using a 'Stable Microsystems' texture analyser. Maximum stress and Young's modulus data were obtained.

Glass Transition Temperature Evaluation

Glass transition temperature (Tg) of the TAOS-CS or H-TAOS-CS pellets was checked using a 'Anton-Paar' rheometer. 400 mg circa of dry pellet blends were placed into the 25 mm rheometer parallel plate and subjected to an oscillatory test at 1 Hz and 0.1% strain with a temperature ramp from 80 to 10° C. Dynamic mechanical analysis (DMA) was used for Tg calculation. DMA measured the viscoelastic moduli, storage and loss modulus and tan delta (peak phase angle) of materials.

Results

TAOS™ Paste Cohesiveness/Early Scaffold Integrity Evaluation

Following the 1 min immersion in water, the aluminium foils containing the samples were carefully removed from the sieve, freeze-dried and the weight loss was estimated (FIG. 20).

This loss was estimated by calculating the weight loss of the dried pastes. Considerable losses did not occur when the pastes were sintered with the liquid carrier containing 2.5% w/v TA. However, substantial mass losses were observed when the pastes were sintered standard liquid carrier. It was shown that pellets shape didn't play a role in scaffold cohesion.

Porosity Assessment

After 24 h of sintering, the dimensions and the densities of freeze-dried scaffolds were measured to calculate the scaffold porosity (FIG. 19). Scaffolds made by hollow pellets shown a porosity increase of about 11-12%.

Molecular Weight Assessment

GPC results demonstrated that both extrusion processes had a minor impact on PLGA 95:5 molecular weight. TAOS-CS and H-TAOS-CS had similar molecular weight when compared with the starting PLGA95:5 molecular weight. Only 5.5 KDa molecular weight drop occurred after the twin and the single screw extrusion processes (FIG. 17).

Strength

From the stress vs strain traces obtained by the texture analyser the Maximum strength and the Young's elastic modulus were calculated. Young's elastic modulus was determined from the gradient of the stress/strain slope prior to fracture. A summary of the data is shown in FIG. 21.

Inspection of the data showed differences in the scaffolds prepared with TAOS-CS or H-TAOS-CS. In general the use of TAOS-CS produced strongest scaffolds especially when 2.5% w/v TA liquid carrier was used. In general, it can be shown that the increased porosity of the scaffolds made with H-TAOS-CS gave less strength to the scaffolds.

Glass Transition Temperature (Tg)

The data obtained from the rheometer software were transferred to Microsoft Excel file (one for each polymer type) and scatter graphs were drawn to show the phase shift angle versus temperature (FIG. 22) and the loss and storage moduli versus temperature (FIG. 23). From the graphs, the temperature at peak phase angle and at peak loss modulus were recorded as an indication of Tg (Table 1). No substantial difference in Tg were recorded for the types of pellets.

TABLE 1

Peak phase angle and at peak loss modulus

| TAOS™-ceramic | Peak loss modulus (° C.) | Peak phase angle (° C.) |
| --- | --- | --- |
| TAOS-CS | 40 | 44 |
| H-TAOS-CS | 41 | 43 |

Example of MSCs Viability after 30 Min

200 μl of a MSCs suspension of 40 million cells/ml were added to 400 mg scaffolds made of TAOS-CS or H-TAOS-CS. The scaffolds and the MSCs were incubated at 37° C. for 30 min. After incubation the MSCs were detached from the scaffolds using trypsin and quantified by haemocytometer analysis. The dead cells were quantified by a trypan blue exclusion assay.

~100% cell viability was achieved. In the H-TAOS-CS scaffolds the MSCs situated inside the pellet hollows did not detach, demonstrating the shielding properties of the H-TAOS-CS.

Example Plasticiser Choice

Table 2 provides examples of water-soluble plasticisers that may be used in the present invention. In embodiments comprising a plasticiser in a carrier according to the present invention, the plasticiser may be selected from Table 2, or used in combinations thereof. The percentage of the plasticiser in the carrier may be up to the specified highest concentration used in a pharmaceutical according to Table 2.

TABLE 2

Water soluble plasticisers

| Plasticiser ($H_2O$ soluble) | Highest concentration used in Pharmaceutical (% w/v) | Source | Solubility in water (% w/v) at 25° C. |
| --- | --- | --- | --- |
| EtOH | 10 | Excipient handbook | Miscible |
| DMSO | 10 | Excipient handbook | Miscible |
| NMP | 78 | Easygraft ™ | Miscible |
| PEG400 | 30 | Excipient handbook | Miscible |
| Glycerol | 88 | Optium ® DBM gel (88%) | Miscible |
| Triethyl Citrate | NA | — | 6.9 |
| Triacetin | NA | — | 5.8 |

The invention claimed is:

1. A scaffold material composition for forming a solid tissue scaffold, the composition comprising a plurality of hollow polymer pellets, each hollow polymer pellet comprising an open lumen extending through the pellet, wherein the lumen volume is at least 10% of each hollow polymer pellet,
   wherein the hollow polymer pellets have a tubular structure, with the lumen extending therethrough, or wherein the hollow polymer pellets have a tubular structure and the lumen is in the form of a channel running through the pellet structure, whereby the channel is open substantially along its length,
   wherein the hollow pellets are 50-700 microns in length,
   wherein the plurality of hollow polymer pellets are capable of interlinking and setting into a solid scaffold, and
   wherein the scaffold material has a porosity of at least about 55%.

2. The scaffold material composition according to claim 1, wherein the hollow polymer pellets comprise one or more polymer selected from the group comprising poly (D,L-lactide-co-glycolide)(PLGA), poly D,L-lactic acid (PDLLA), polyethyleneimine (PEI), polylactic or polyglcolic acids, poly-lactide poly-glycolide copolymers, and poly-lactide, poly-glycolide, polyethylene glycol copolymers, polyethylene glycol (PEG), polyesters, poly (ε-caprolactone), poly (3-hydroxy-butyrate), poly (s-caproic acid), poly (p-dioxanone), poly (propylene fumarate), poly (ortho esters), polyol/diketene acetals addition polymers, polyanhydrides, poly (sebacic anhydride) (PSA), poly (carboxybis-carboxyphenoxyphosphazene) (PCPP), poly [bis (p-carboxyphenoxy) methane] (PCPM), copolymers of SA, CPP and CPM, poly (amino acids), poly (pseudo amino acids), polyphosphazenes, derivatives of poly [(dichloro) phosphazene], poly [(organo) phosphazenes], polyphosphates, polyethylene glycol polypropylene block co-polymers, natural or synthetic polymers, silk, elastin, chitin, chitosan, fibrin, fibrinogen, polysaccharides, peptides, polypeptides, proteins, copolymers prepared from the monomers of any of these polymers, random blends of any of these polymers, and mixtures or combinations thereof.

3. The scaffold material composition according to claim 1, wherein the hollow polymer pellets comprise a plasticiser.

4. The scaffold material composition according to claim 1, wherein the scaffold material composition comprises a liquid carrier.

5. The scaffold material composition according to claim 4, wherein the liquid carrier comprises a plasticiser; or the hollow polymer pellets and the liquid carrier comprise a plasticiser.

6. The scaffold material composition according to claim 5, wherein the plasticiser in the hollow polymer pellets is different from the plasticiser in the liquid carrier.

7. The scaffold material composition according to claim 1, wherein the hollow polymer pellets comprise:
synthetic polymer blended with natural-polymer particles; non-polymer particles; or
synthetic polymer blended with natural-polymer particles and non-polymer particles.

8. The scaffold material composition according to claim 1, wherein the hollow polymer pellets comprise or further comprise ceramic.

9. The scaffold material composition according to claim 1, wherein the scaffold material comprises an active agent.

10. The scaffold material composition according to claim 9, wherein the active agent comprises a bone morphogenic protein.

11. The scaffold material composition according to claim 10, wherein:
the active agent is encapsulated within the material of the hollow polymer pellets;
the active agent is provided amongst the hollow polymer pellets in a liquid carrier; or
the active agent is encapsulated within the material of the hollow polymer pellets and provided amongst the hollow polymer pellets in a liquid carrier.

12. The scaffold material composition according to claim 1, further comprising cells.

13. A solid scaffold for tissue repair or replacement comprising a plurality of hollow polymer pellets, the hollow polymer pellets comprising a polymer pellet having an open lumen extending through the polymer pellet wherein the lumen has a diameter of between 10 μm and 300 μm, and the lumen volume is at least 10% of each hollow polymer pellet,
wherein the hollow polymer pellets have a tubular structure, with the lumen extending therethrough, or wherein the hollow polymer pellets have a tubular structure and the lumen is in the form of a channel running through the pellet structure, whereby the channel is open substantially along its length,
wherein the hollow polymer pellets are inter-linked with each other,
wherein the hollow pellets are 50-700 microns in length, and
wherein the solid scaffold has a porosity of at least about 55%.

14. The solid scaffold according to claim 13, wherein the hollow polymer pellets are non-uniformly orientated relative to each other.

15. The solid scaffold according to claim 13, further comprising an active agent, wherein
the active agent is encapsulated within the material of the hollow polymer pellets;
the active agent is provided amongst the hollow polymer pellets in a liquid carrier; or
the active agent is encapsulated within the material of the hollow polymer pellets and provided amongst the hollow polymer pellets in a liquid carrier.

16. The solid scaffold according to claim 15, wherein the active agent comprises bone morphogenic protein.

17. The solid scaffold according to claim 13, further comprising cells.

18. The solid scaffold according to claim 13, wherein the hollow polymer pellets comprise a plasticiser.

19. The solid scaffold according to claim 13, further comprising a liquid carrier.

20. The solid scaffold according to claim 19, wherein the liquid carrier comprises a plasticiser; or wherein the liquid carrier and the hollow polymer pellets comprise a plasticiser.

21. The solid scaffold according to claim 20, wherein the plasticiser in the hollow polymer pellets is different to the plasticiser in the liquid carrier.

22. The solid scaffold according to claim 13, wherein the hollow polymer pellets comprise one or more polymer selected from the group comprising poly (D,L-lactide-co-glycolide)(PLGA), poly D,L-lactic acid (PDLLA), polyethyleneimine (PEI), polylactic or polyglcolic acids, polylactide poly-glycolide copolymers, and poly-lactide, polyglycolide, polyethylene glycol copolymers, polyethylene glycol (PEG), polyesters, poly (ε-caprolactone), poly (3-hydroxy-butyrate), poly (s-caproic acid), poly (p-dioxanone), poly (propylene fumarate), poly (ortho esters), polyol/diketene acetals addition polymers, polyanhydrides, poly (sebacic anhydride) (PSA), poly (carboxybiscarboxyphenoxyphosphazene) (PCPP), poly [bis (p-carboxyphenoxy) methane] (PCPM), copolymers of SA, CPP and CPM, poly (amino acids), poly (pseudo amino acids), polyphosphazenes, derivatives of poly [(dichloro) phosphazene], poly [(organo) phosphazenes], polyphosphates, polyethylene glycol polypropylene block co-polymers, natural or synthetic polymers, silk, elastin, chitin, chitosan, fibrin, fibrinogen, polysaccharides, peptides, polypeptides, proteins, copolymers prepared from the monomers of any of these polymers, random blends of any of these polymers, and mixtures or combinations thereof.

23. The solid scaffold according to claim 13, wherein the hollow polymer pellets comprise:
synthetic polymer blended with natural-polymer particles; non-polymer particles; or
synthetic polymer blended with natural-polymer particles and non-polymer particles.

24. The solid scaffold according to claim 13, wherein the hollow polymer pellets comprise ceramic.

25. A kit for use in forming a scaffold and delivery of an agent, the kit comprising hollow polymer pellets, wherein the hollow polymer pellets:
comprise an open lumen extending through the pellet, and wherein the lumen volume is at least 10% of each hollow polymer pellet,
have a tubular structure, with the lumen extending therethrough, or have a tubular structure and the lumen is in the form of a channel running through the pellet structure, whereby the channel is open substantially along its length,
are 50-700 microns in length, and
are capable of interlinking and setting into a scaffold,
wherein the scaffold material has a porosity of at least about 55%;
an active agent; and
a liquid carrier solution; and optionally
instructions to mix the hollow polymer pellets, the active agent and the liquid carrier to form a scaffold.

26. The kit according to claim 25, wherein the active agent is in powder form.

27. The kit according to claim 25, wherein the hollow polymer pellets comprise one or more polymer selected from the group comprising poly (α-hydroxyacids), including poly (D,L-lactide-co-glycolide)(PLGA), poly D, L-lactic acid (PDLLA), polyethyleneimine (PEI), polylactic or polyglcolic acids, poly-lactide poly-glycolide copolymers, and poly-lactide, poly-glycolide, polyethylene glycol copolymers, polyethylene glycol (PEG), polyesters, poly (ε-caprolactone), poly (3-hydroxy-butyrate), poly (s-caproic acid), poly (p-dioxanone), poly (propylene fumarate), poly (ortho esters), polyol/diketene acetals addition polymers, polyanhydrides, poly (sebacic anhydride) (PSA), poly (carboxybiscarboxyphenoxyphosphazene) (PCPP), poly [bis (p-carboxyphenoxy) methane] (PCPM), copolymers of SA, CPP and CPM, poly (amino acids), poly (pseudo amino acids), polyphosphazenes, derivatives of poly [(dichloro) phosphazene], poly [(organo) phosphazenes], polyphosphates, polyethylene glycol polypropylene block co-polymers, natural or synthetic polymers, silk, elastin, chitin, chitosan, fibrin, fibrinogen, polysaccharides, including pectins, alginates, collagen, peptides, polypeptides or proteins, copolymers prepared from the monomers of any of these polymers, random blends of these polymers, any suitable polymer and mixtures or combinations thereof.

28. The kit according to claim 25, wherein the hollow polymer pellets comprise a plasticiser.

29. The kit according to claim 25, wherein the liquid carrier comprises a plasticiser; or the hollow polymer pellets and the liquid carrier comprise a plasticiser.

30. The kit according to claim 29, wherein the plasticiser in the hollow polymer pellets is different to the plasticiser in the liquid carrier.

31. The kit according to claim 25, wherein the hollow polymer pellets comprise:
  synthetic polymer blended with natural-polymer particles;
  non-polymer particles; or
  synthetic polymer blended with natural-polymer particles and non-polymer particles.

32. The kit according to claim 25, wherein the hollow polymer pellets comprise ceramic.

33. The kit according to claim 25, wherein the active agent comprises bone morphogenic protein.

34. The kit according to claim 25, wherein:
  the active agent is encapsulated within the material of the hollow polymer pellets;
  the active agent is provided in the liquid carrier; or
  the active agent is encapsulated within the material of the hollow polymer pellets and provided in the liquid carrier.

35. The kit according to claim 25, further comprising cells.

* * * * *

UNITED STATES PATENT AND TRADEMARK OFFICE
CERTIFICATE OF CORRECTION

| | | |
|---|---|---|
| PATENT NO. | : 11,904,070 B2 | Page 1 of 1 |
| APPLICATION NO. | : 16/485882 | |
| DATED | : February 20, 2024 | |
| INVENTOR(S) | : Antonio Leonardi et al. | |

It is certified that error appears in the above-identified patent and that said Letters Patent is hereby corrected as shown below:

On the Title Page

At (71) Applicant, change "Locate Therapeutics Limited" to --Locate Bio Limited--

At (73) Assignee, change "Locate Therapeutics Limited" to --Locate Bio Limited--

Signed and Sealed this
Fourteenth Day of May, 2024

*Katherine Kelly Vidal*
Katherine Kelly Vidal
*Director of the United States Patent and Trademark Office*